(12) United States Patent
Ammendola et al.

(10) Patent No.: US 7,335,779 B2
(45) Date of Patent: Feb. 26, 2008

(54) MODULATION OF PATHOGENICITY

(75) Inventors: Aldo Ammendola, München (DE);
Katharina Aulinger-Fuchs, Neuried (DE); Astrid Gotschlich, München (DE); Bernd Kramer, Aachen (DE); Martin Lang, Gräfelfing (DE); Wael Saeb, Planegg-Martinsried (DE); Udo Sinks, München (DE); Andreas Wuzik, Untermeitingen (DE)

(73) Assignee: Quonova, LLC, Melbourne, FL (US)

( * ) Notice: Subject to any disclaimer, the term of this patent is extended or adjusted under 35 U.S.C. 154(b) by 457 days.

(21) Appl. No.: 10/429,875

(22) Filed: May 6, 2003

(65) Prior Publication Data

US 2004/0063765 A1 Apr. 1, 2004

Related U.S. Application Data

(63) Continuation-in-part of application No. 10/094,301, filed on Mar. 8, 2002, now abandoned.

(51) Int. Cl.
C07D 231/00 (2006.01)
C07D 233/00 (2006.01)
C07D 233/02 (2006.01)

(52) U.S. Cl. ................ 548/371.4; 548/300.1
(58) Field of Classification Search .......... 548/374.1; 514/300.1
See application file for complete search history.

(56) References Cited

U.S. PATENT DOCUMENTS

| | | | |
|---|---|---|---|
| 4,069,252 A | 1/1978 | Findeisen | |
| 4,146,454 A | 3/1979 | Haber | |
| 4,166,123 A * | 8/1979 | Harrison et al. | 514/407 |
| 4,301,235 A * | 11/1981 | Ichijima et al. | 430/387 |
| 4,436,479 A | 3/1984 | Belloli | |
| 4,799,951 A * | 1/1989 | Stetter et al. | 504/253 |
| 5,155,011 A | 10/1992 | Zertani | |
| 5,190,928 A | 3/1993 | Schurter | |
| 5,256,634 A * | 10/1993 | Schallnor et al. | 504/282 |
| 5,395,730 A | 3/1995 | Podszun | |
| 5,523,311 A | 6/1996 | Schurter | |
| 5,585,473 A | 12/1996 | Bendiak | |
| 5,612,359 A | 3/1997 | Murugesan | |
| 5,846,990 A | 12/1998 | Murugesan | |
| 5,990,109 A | 11/1999 | Chen | |
| 6,100,288 A * | 8/2000 | Wemthaler et al. | 514/404 |
| 6,159,980 A | 12/2000 | Arvanitis | |
| 6,172,222 B1 * | 1/2001 | Gilbert et al. | 544/53 |
| 6,300,352 B1 | 10/2001 | Cheshire | |
| 6,395,282 B1 | 5/2002 | Kende et al. | |
| 6,399,773 B1 | 6/2002 | Liu | |
| 6,476,042 B1 | 11/2002 | Harrison | |
| 6,511,997 B1 * | 1/2003 | Minami et al. | 514/341 |
| 6,555,540 B1 | 4/2003 | Mylari | |
| 6,815,528 B2 | 11/2004 | Wang | |
| 6,858,627 B2 | 2/2005 | Bekkali | |
| 6,894,111 B2 | 5/2005 | Wang | |
| 2004/0019117 A1 | 1/2004 | Protopopova | |
| 2004/0033986 A1 | 2/2004 | Protopopova | |
| 2006/0073667 A1 | 4/2006 | Li | |

FOREIGN PATENT DOCUMENTS

| | | |
|---|---|---|
| EP | 0 525 686 | 2/1993 |
| EP | 0 540 472 | 5/1993 |
| EP | 0 638 545 | 2/1995 |
| EP | 0 982 292 | 3/2000 |
| FR | 1 439 334 | 4/1966 |
| GB | 2 331 299 | 5/1999 |
| JP | 3-232849 | 10/1991 |
| WO | WO 95/24403 | 9/1995 |
| WO | 96/29392 | 9/1996 |
| WO | 98/57618 | 12/1998 |
| WO | 98/58075 | 12/1998 |

(Continued)

OTHER PUBLICATIONS

Hentzer, M., et al. Microbiology 2002, 148, 87-102.*

(Continued)

Primary Examiner—Sreeni Padmanabhan
Assistant Examiner—Umamaheswari Ramachandran
(74) Attorney, Agent, or Firm—Womble Carlyle Sandridge & Rice, PLLC

(57) ABSTRACT

The present invention relates to the use of compounds of the general Formula (I):

$$A^1 - \left[ \begin{array}{c} R \\ | \\ N \end{array} \right]_p - Y^1 - N - \left[ \begin{array}{c} R^2 \\ | \\ N \end{array} - Y^2 \right]_n - A^2$$

wherein in Formula (I),
R is H, alkyl, cycloalkyl, aryl or heteroaryl;
$R^1$ is H, alkyl, cycloalkyl, aryl or heteroaryl;
$R^2$ is H, alkyl, cycloalkyl, aryl or heteroaryl;
$A^1$ and $A^2$ each independently represent an optionally substituted $C_1$-$C_{20}$-alkyl group which may contain one or more group(s) Z, or a monocyclic or polycyclic optionally substituted aromatic or non-aromatic ring system which may contain one or more group(s) X, and in case of a polycyclic ring system, said system contains at least one aromatic ring;
Z is selected from the group consisting of S, O, N, $NR^4$, CO, $CO_2$, CS, SO or $SO_2$
X is selected from the group consisting of S, O, N, $NR^4$, SO or $SO_2$.

4 Claims, 5 Drawing Sheets

FOREIGN PATENT DOCUMENTS

| WO | WO 98/57618 | 12/1998 |
|---|---|---|
| WO | 99/27786 | 6/1999 |
| WO | WO 99/27786 | 6/1999 |
| WO | 99/53915 | 10/1999 |
| WO | 99/55368 | 11/1999 |
| WO | 01/26650 | 4/2001 |
| WO | 01/51456 | 7/2001 |
| WO | 02/088298 | 11/2002 |
| WO | 03/004017 | 1/2003 |
| WO | WO/2003/015778 | 2/2003 |
| WO | 03/022828 | 3/2003 |
| WO | 03/026641 | 4/2003 |
| WO | WO 03/039529 | 5/2003 |
| WO | WO 03/039549 | 5/2003 |

OTHER PUBLICATIONS

Eichenberger et al. Helvitica Chimica Acta 1965, 48, 524-527.*
Burch, H. J. Med. Chem. 1967, 11, 79-83.*
Patent Abstracts of Japan, JP 59-210440, Nov. 29, 1984.
C. S. Pak, et al., Synthesis, vol. 12, XP-001154580, pp. 1213-1214, "Aminolysis of 5-Acyl-2,2-Dimethyl-1,3-Dioxane-4,6-Diones (Acyl Meldrum's Acids) as a Versatile Method for the Synthesis of β-OXO Carboxamides", Dec. 1992.
K. M. Smith, et al., Chemistry & Biology, vol. 10, No. 1, XP-002254860, pp. 81-89, "Induction and Inhibition of Pseudomonas Aeruginosa Quorum Sensing by Synthetic Autoinducer Analogs", Jan. 2003.
Chhabra, S. R., et al., "Synthetic Analogues of the Bacterial Signal (Quorum Sensing) Molecule N-(3-Oxododecanoyl)-L-homoserine Lactone as Immune Modulators," J. Med. Chem. 2003, 46, 97-104.
Clark, D. J.; Maaløe, O., "DNA Replication and the Division Cycle in Escherichia coli," J. Mol. Biol. (1967) 23, 99-112.
Costerton, J. W., et al., "Microbial Biofilms," Annu. Rev. Microbiol. 1995, 49, 71-745.
Costerton, J. W., et al., "Bacterial Biofilms: A Common Cause of Persistent Infections," Science 1999, 284, 1318-1322.
Davies, D. G., et al., "The Involvement of Cell-to-Cell Signals in the Development of a Bacterial Biofilm," Science, 1998, 280, 295-298.
DE Kievit, T. R. and Iglewski, B. H., "Bacterial Quorum Sensing in Pathogenic Relationships," Infection and Immunity, 2000, 68(9), 4839-4849.
Dong, Y.-H., et al., "Quenching quorum-sensing-dependent bacterial infection by an N-acyl homoserine lactonase," Nature, 2001, 411, 813-817.
Eberl, L. "N-Acyl Homserinelactone-mediated Gene Regulation in Gram-negative Bacteria," System. Appl. Microbiol., 1999, 22-493-506.
Stickler, D. J., et al., "Biofilms on Indwelling Urethral Catheters Produce Quorum-Sensing Signal Molecules in Situ and In Vitro," Appl. Environ. Microbiol., 1998, 64(9), 3486-3490.
Swift, S., et al., "Quorum Sensing in Aeromonas hydrophila and Aeromonas salmonicida: Identification of the LuxRI Homologs AhyRI and AsaRI and Their Cognate N-Acythomoserine Lactone Signal Molecules," J. Bacteriology, 1997, 179(17), 5271-5281.
Zhu, J., et al. "Analogs of the Autoinducer 3-Oxooctanoyl-Homoserine Lactone Strongly Inhibit Activity of the TraR Protein of Agrobacterium tumefaciens," J. Bacteriology, 1998, 180(20), 5398-5405.
Smith, K. M., et al., "Library Screening for Synthetic Agonists and Antagonists of a Pseudomonas aeruginosa Autoinducer," Chemistry & Biology, 2003, 10, 563-571.
Lewis, K. "Riddle of Biofilm Resistance," Antimicrobial Agents and Chemotherapy, 2001, 45(4), 999-1007.
McClean, K. H., et al., "Quorum sensing and Chromobacterium violaceum: exploitation of violacein production and inhibition for the detection of N-acylhomoserine lactones," Microbiology, 1997, 143, 3703-3711.

O'Toole, G. A. and Kolter, R., "Initiation of biofilm formation in Pseudomonas fluorescens WCS365 proceeds via multiple, convergent signalling pathways: a genetic analysis," Molecular Microbiology, 1998, 28(3), 449-461.
Pesci, E. C., et al., "Regulation of las and rhl Quorum Sensing in Pseudomonas aeruginosa," J. Bacteriology, 1997, 179(10), 3127-3132.
Pratt, L. A. and Kolter, R., "Genetic analysis of Escherichia coli biofilm formation: roles of flagella, motility, chemotaxis and type I pili," Molecular Microbiology, 1998, 30(2), 285-293.
Römling, U., et al., "Epidemiology of Chronic Pseudomonas aeruginosa Infections in Cystic Fibrosis," J. Infectious Diseases, 1994, 170, 1616-1621.
Schaefer, A. L., et al., "Quorum Sensing in Vibrio fischeri: Probing Autoinducer-LuxR Interactions with Autoinducer Analogs," J. Bacteriology, 1996, 178(10), 2897-2901.
Clay Fuqua, et al., "Census and Consensus in Bacterial Ecosystems: The LuxR-LuxI Family of Quorum-Sensing Transcriptional Regulators," Annu. Rev. Microbiol. 1996, vol. 50, pp. 727-751.
Brigit Huber, et al., "The cep quorum-sensing system of Burkholderia cepacia H111 controls biofilm formation and swarming motility," Microbiology, 2001, vol. 147, pp. 2517-2528.
J. R. W. Govan, et al., "Burkholderia cepacia: medical, taxonomic and ecological issues," J. Med. Microbiol., vol. 45, 1996, pp. 395-407.
Morten Hentzer, et al., "Inhibition of quorum sensing in Pseudomonas aeruginosa biofilm bacteria by a halogenated furanone compound," Micorbiology, 2002, vol. 148, pp. 87-102.
Kristina M. Smith, et al., "Library Screening for Synthetic Agonists and Antagonists of a Pseudomonas aeruginosa Autoinducer," Chemistry & Biology, vol. 10, Jun. 2003, pp. 563-571.
W. Claiborne Fuqua, et al., "Quorum Sensing in Bacteria: the LuxR-LuxI Family oc Cell Density-Responsive Transcriptional Regulators," Journal of Bacteriology, Jan. 1994, pp. 269-275.
Chwang Siek Pak, et al., "Aminolysis of 5-Acyl-2,2-dimethyl-1,3-dioxane-4,6-diones (Acyl Meldrum's Acids) as a Versatile Method for the Synthesis of β-Oxo Carboxamides," Synthesis, Dec. 1992, pp. 1213-1214.
Y. Oikawa, et al., "Methyl Phenylacetylacetate From Phenylacetyl Chloride and Meldrum's Acid," Organic Syntheses, vol. 7, pp. 359-360.
Yuji Oikawa, et al., Meldrum's Acid in Organic Synthesis. 2. A General and Versatile Synthesis of β-Keto Esters, J. Org. Chem., vol. 43, No. 10, 1978, pp. 2087-2088.
Masaaki Nakahata, et al., "The Preparation of Optically Pure 3-Hydroxyalkanoic Acid. The Enantioface-differentiating Hydrogenation of the C=O Double Bond with Modified Ranney Nickel. XXXVII.," Bull. Chem. Soc. Jpn., vol. 55, No. 7, 1982, pp. 2186-2189.
Keizo Matsuo, et al., "Structure-Activity Relationships in Tetramic Acids and Their Copper (II) Complexes[1])," Chem., Pharm, Bull., vol. 28, 1980, pp. 2494-2502.
Lydia Monti, et al., "Sulla preparazione della α-ossi-γ-metil-chinoline.", Questa Gazzetta, vol. 66, 1936, pp. 723-731.
Mouloud Dekhane, et al., "A Novel Convenient Route to the Naturally Occurring 3-Oxoacyl-L-Homoserinelactones and Related Bacterial Autoinducers.", Tetrahedron Letters, vol. 37, No. 11, 1996, pp. 1883-1884.
Corinne E. Augelli-Szafran, et al., "Inhibitors of Acyl-CoA:Cholesterol Acyltransferase. 5. Identification and Structure-Activity Relationships of Novel β-Ketoamides as Hypocholesterolemic," J. Med. Chem., 1993, vol. 36, pp. 2943-2949.
Michael Rowley, et al., "3-Acyl-4-hydroxyquinolin-2(1H)-ones. Systemically Active Anticonvulsants Acts by Antagonism at the Glycine Site of the N-Methyl-D-Aspartate Receptor Comp," J. Med. Chem., vol. 36, 1993, pp. 3386-3396.
Masayuki Sato, et al., "Synthesis of β-Ketocarboxamide Derivatives Using 2,2-Dimethyl-2H,4H-1,3-dioxin-4-ones," Chem. Pharm. Bull., vol. 32, 1984, pp. 3848-3856.
Chris J. Brennan, et al., "Synthetic studies towards the group A streptogramin antibiotics. Synthesis of the C9-C23 fragment," Tetrahedron Letters, vol. 42, 2001, pp. 5195-5197.

Robert A Singer, et al., "Catalytic, Enantioselective Dienolate Additions to Aldehydes: Preparation of Optically Active Acetoacetate Aldol Adducts," J. Am. Chem. Soc., Vol. 117, 1995, pp. 12360-12361.

K. A. Zirvi, et al., "Synthesis and Neuropharmacology of Butyrytureas," Formaco Ed. Sci., vol. 37, 1982, pp. 335-342.

Whei Oh Lin, et al., "Phenylenedioxydiacetamide End Group Effect," Montashelte für Chemie, vol. 112, 1981, pp. 871-873.

Whei Oh Lin, et al., "Neutral Diamide Ionophores Phenylenedioxydiacetamides," Montashette für Chemie, vol. 113, 1982, pp. 101-109.

Albert Padwa, et al., "Rhodium(II)-Catalyzed Equilibration of Push-Pull Carbonyl and Ammonium Ylides. A Computationally Based Understanding of the-Reaction Pathway," J. Am. Chem. Soc., 2000, vol. 122, pp. 8155-8167.

J. L. Belletire, et al., "Exploratory Synthetic Methodology Involving the Acytureas," Synthetic Communication, 19(20), 1989, pp. 3543-3551.

Astric Gotschlich, et al., "Synthesis of Multiple N-Acythomoserine Lactones is Wide-spred Among the Members of the Burkholderia cepacia Complex," System Appl. Microbiol., vol. 24, 2001, pp. 1-14.

D. Joseph Clark, et al., "DNA Replication and the Division Cycle in *Escherichia coli*," J. Mol. Biol. Vol. 23, 1967, pp. 99-112.

J. R. W., Govan, et al., "Microbial Pathogenesis in Cystic Fibrosis: Mucoid *Pseudomonas aeruginosa* and *Burkholderia cepacia*," Microbiological Reviews, Sep. 1996, pp. 539-574.

* cited by examiner

MODULATION OF PATHOGENICITY

FIELD THE INVENTION

The present invention relates to the use of compounds such as amide, carbazide and hydrazide derivatives as selective inhibitors of bacterial pathogens. In particular the invention refers to a family of compounds that block the quorum sensing system of Gram-negative bacteria, a process for their manufacture, pharmaceutical compositions containing them and to their use for the treatment and prevention of microbial damages and diseases, in particular for diseases where there is an advantage in inhibiting quorum sensing regulated phenotypes of pathogens.

BACKGROUND OF THE INVENTION

Many microorganisms, including bacteria, fungi, protozoa and algae cause severe damages or diseases in different areas such as industry, agriculture, environment and medicine. Especially bacteria as human pathogens cause tremendous costs in public health systems worldwide. The continuing emergence of multiple-drug-resistant bacterial strains has necessitated finding new compounds that can be used in antibacterial treatment. There are two broad strategies for the control of bacterial infection: either to kill the organism or to attenuate its virulence such that it fails to adapt to the host environment. The latter approach has, however, lacked specific targets for rational drug design. The discovery that Gram-negative bacteria employ a signal transduction pathway comprising a small molecule to globally regulate the production of virulence determinants offers such a novel target.

A wide variety of Gram-negative bacteria produce N-acyl-L-homoserine lactone (AHL or HSL, FIG. 1) derivatives as signal molecules in intercellular communication. These molecules, also referred to as "pheromones" or "quoromones", comprise a homoserine lactone moiety linked to an acyl side chain. Bacteria use this signaling system to monitor their population cell density in a process referred to as "quorum sensing". In each cell of a population an HSL synthase from usually the LuxI family of proteins produce a low basal level of diffusible HSLs. The HSL concentration increases with bacterial population density until a threshold concentration is reached which results in expression of various HSL-dependent genes through an HSL-receptor protein belonging generally to the LuxR family of transcriptional regulators. This HSL-receptor protein complex serves not only as positive transcription regulator of quorum sensing regulated genes but also as positive regulator for the HSL synthesis itself. Therefore, the entire system is amplified via a process of autoinduction.

This system was first discovered in the bioluminescent marine bacteria *Vibrio harveyi* and *V. fischeri* where it is used to control bioluminescence expression. In recent years it has become apparent that many Gram-negative bacteria employ one or more quorum sensing systems comprising HSL derivatives with different acyl side chains to regulate in a cell-density dependent manner a wide variety of physiological processes such as swarming motility, biofilm formation, pathogenicity, conjugation, bioluminescence or production of pigments and antibiotics (Table 1, for reviews and further references see, e.g.: Fuqua et al, *Ann. Rev. Microbiol.* 50:727-51, 1996; Fuqua & Greenberg, *Curr. Opinion Microbiol.* 1:183-89, 1998; Eberl, *Syst. Appl. Microbiol.* 22:493-506, 1999; De Kievit & Iglewski, *Infect. Immun.* 68:4839-49, 2000).

TABLE 1

Summary of HSL-based quorum sensing systems

| Bacterium | Regulatory Proteins | Major HSL | HSL-regulated phenotype |
| --- | --- | --- | --- |
| *Aeromonas hydrophila* | AhyR, AhyI | C4-HSL | Extracellular protease, bioflim formation |
| *Aeromonos salmonicida* | AsaR, AsaI | C4-HSL | Extracellular protease |
| *Agrobacterium tumefaciens* | TraR, TraI | 3-oxo-C8-HSL | Conjugal transfer |
| *Burkholderia cepacia* | CepR, CepI | C8-HSL | Protease, lipase, ornibactin synthesis, biofilm formation, swarming motility |
| *Chromobacterium violaceum* | CviR, CviI | C6-HSL | Antibiotics, violacein, exoenzymes, cyanide |
| *Enterobacter agglomerans* | EagR, EagI | 3-oxo-C6-HSL | Unknown |
| *Erwinia carotovora* | CarR, (CarI) ExpR, ExpI | 3-oxo-C6-HSL | Carbapenem antibiotics, exoenzyme production |
| *Erwinia chrysanthemi* | ExpR. ExpI (EchR, EchI) | 3-oxo-C6-HSL | Pectinase expression |
| *Escherichia coli* | SdiA | Unknown | Cell division, virulence factor production |
| *Nitrosomonas europaea* | Unknown | 3-oxo-C6-HSL | Emergence from lag phase |
| *Obesumbacterium proteus* | OprR, OprI | 3-oxo-C6-HSL | Unknown |
| *Pantoea stewartii* | EsaR, EsaI | 3-oxo-C6-HSL | Exopolysaccharide production, virulence factor production |
| *Pseudomonas aeruginosa* | LasR, LasI | 3-oxo-C12-HSL | Extracellular virulence factors, Xcp, biofilm formation, RpoS, RhlR |
| *Pseudomonas aeruginosa* | RhlR, RhlI | C4-HSL | Extracellular virulence factors, cyanide, lectins, pyocyanin, rhamnolipid, type 4 pili, twitching motility |

TABLE 1-continued

Summary of HSL-based quorum sensing systems

| Bacterium | Regulatory Proteins | Major HSL | HSL-regulated phenotype |
|---|---|---|---|
| *Pseudomonas aureofaciens* | PhzR, PhzI | C6-HSL | Phenazine antibiotics |
| *Pseudomonas fluorcscens* | HdtS | 3-hydroxy-7-cis-C14-HSL | Unknown |
| *Ralstonia solanacearum* | SolR, SolI | C8-HSL | Unknown |
| *Rhizobium etli* | RaiR, RaiI | 7 HSLs | Root nodulation |
| *Rhizobium leguminosarum* | RhiR | 3-hydroxy-7-cis-C14-HSL | Nodulation, bacteriocin, stationary phase survival |
| *Rhizobium leguminosarum* | RhiR, RhiI | C6-HSL, C8-HSL | rhizome interactions |
| *Rhodobacter sphaeroides* | CerR, CerI | 7-cis-C14-HSL | Clumping factor |
| *Serratia liquefaciens* | SwrR, SwrI | C4-HSL | Swarming motility, protease, serrawettin W2, lipase |
| *Vibrio anguillarum* | VanR, VanI | 3-oxo-C10-HSL | Unknown |
| *Vibrio anguillarum* | VanM, VanN | C6-HSL, 3-hydroxy-C6-HSL | Unknown |
| *Vibrio fischeri* | LuxR, LuxI | 3-oxo-C6-HSL | Bioluminescence |
| *Vibrio harveyi* | LuxM, LuxN | 3-hydroxy-C4-HSL | Bioluminescence, PHB synthesis |
| *Xenorhabdus nematophilus* | Unknown | 3-hydroxy-C4-HSL | Virulence |
| *Yersinia enterocolitica* | YenR, YenI | C6-HSL, 3-oxo-C6-HSL | Unknown |
| *Yersinia pestis* | YpeR, YpeI | Unknown | Unknown |
| *Yersinia pseudotuberculosis* | YpsR, YpsI | 3-oxo-C6-HSL | Motility, clumping |
| *Yersinia pseudotuberculosis* | YtbR, YtbI | C8-HSL | Unknown |
| *Yersinia ruckeri* | YukR, YukI | Unknown | Unknown |

With regard to bacteria that utilize HSL-based quorum sensing as part of their lifestyle, *Pseudomonas aeruginosa* is perhaps the best understood in terms of the role quorum sensing plays in pathogenicity. In this human opportunistic pathogen, which causes nosocomial infections in immunocompromized patients and has an extremely high potential to develop resistance mechanisms against traditional antibiotic treatment, production of many virulence factors including expression of alkaline protease, endoproteinase, LasA protease, LasB elastase, anthranilate synthase, hemolysins, lectin, cytochrome c oxidase, catalase, Mn- and Fe-dependent superoxide dismutases, exotoxin A, exoenzyme S, chitinase, chitin binding protein, phenazine, hydrogen cyanide, pyocyanin, pyoverdine, phospholipase C, rhamnolipids, sigma factor S, components of the protein secretion apparatus, efflux transporters, production of alginate and adhesion, twitching motility and pilin export is regulated by two interlinked quorum sensing circuits, Moreover, it has been demonstrated that this signaling system is involved in the ability of *P. aeruginosa* to form biofilms (Davies et al, *Science* 280:295-8, 1998). Recently Huber et al. (*Microbiology* 147:2517-28, 2001) demonstrated that biofilm formation and swarming motility of *Burkholderia cepacia*, like *P. aeruginosa* a human opportunistic pathogen, is also dependent on an HSL-based quorum sensing system.

Biofilms are defined as an association of microorganisms growing attached to a surface and producing a slime layer of extracellular polymers in which the microbial consortia is embedded in a protective environment (for a review see: Costerton et al., *Ann. Rev. Microbiol.* 49:711-45, 1995). Biofilms represent a severe problem as bacteria integrated in such a polymer matrix develop resistance to conventional antimicrobial agents. *P. aeruginosa* cells, for example, growing in an alginate slime matrix have been demonstrated to be resistant to antibiotics (e.g., aminoglycosides, β-lactam antibiotics, fluoroquinolones) and disinfectants (Govan & Deretic, *Microbiol. Rev.* 60:539-74, 1996). Several mechanisms for biofilm-mediated resistance development have been proposed (Costerton et al., *Science* 284:1318-22, 1999).

In most natural, clinical and industrial settings bacteria are predominantly found in biofilms. Drinking water pipes, ship hulls, teeth or medical devices represent typical surfaces colonized by bacteria. On the one hand biofilms decrease the life time of materials through corrosive action in the industrial field, a process also referred to as "biofouling". Furthermore, microbial biofilms growing for example on ship hulls increase fuel consumption through enhanced frictional resistance and simultaneously reduce maneuverability. On the other hand two thirds of all bacterial infections in humans are associated with biofilms (Lewis, *Antimicrob. Agents Chemother.* 45:999-1007, 2001).

*Pseudomonas aeruginosa*, for example, forms infectious biofilms on surfaces as diverse as cystic fibrosis lung tissue, contact lenses, and Catheter tubes (Stickler et al., *Appl. Environm. Microbiol.* 64:3486-90, 1998). *Burkholderia cepacia* also forms biofilms in lungs of cystic fibrosis patients and is a major industrial contaminant (Govan et al., *J. Med. Microbiol.* 45:395-407, 1996). Since biofilm formation of both organisms is demonstrated to require an HSL signaling system, inhibition of their quorum sensing systems would result in an impaired ability to form biofilms and therefore in an increased susceptability to antibacterial treatment.

Beside the role of HSL derivatives as signaling molecules of bacterial cell-to-cell communication it has been demonstrated that HSL interfere also with higher organisms. Since HSL derivatives inhibit murine and human leucocyte proliferation and TNF-alpha secretion by lipopolysaccharide (LPS) stimulated human leucocytes (Chhabra et al., *J. Med. Chem.* 46:97-104, 2003), the suitability of these compounds for immunological diseases, particularly autoimmune diseases such as psoriasis, rheumatoid arthritis, multiple sclerosis and type 1 (autoimmune) diabetes is indicated (WO 03/004017, WO 03/022828).

Furthermore, certain HSL molecules are capable of reducing the heart beat without substancially reducing arterial blood pressure. These compounds and analogs of them could, therefore, be suitable for the treatment of cardiac tachyarrhythmias, ischaemic heart disease, congestive heart failure (WO 01/26650). Additionally, HSL compounds have been reported as possible antiallergic drug (WO 95/01175) and for the treatment of a range of diseases including cancer, breast cancer, obesity, lipid metabolism disorders, immune disease, immune deficiency or immune disorders by modulationg STAT activity (WO 03/026641).

The discovery that a wide spectrum of bacterial organisms use quorum sensing to control virulence factor production and other phenotypes such as biofilm formation makes it an attractive target for antimicrobial therapy. Pathogenic organisms using this signaling system to control virulence could potentially be rendered avirulent by blocking this cell-cell communication system. In contrast to traditional antibiotics, the risk of resistance development seems to be very low, since quorum sensing blocking agents would not kill the organism but disturb signal transduction pathways. There are several possibilities of interrupting the quorum sensing circuit.

For example, plants expressing an HSL-lactonase enzyme originally derived from *Bacillus* sp. have been demonstrated to quench pathogen quorum sensing signaling and to significantly enhance resistance to *Erwinia carotovora* infections (Dong et al., *Nature* 411:813-7, 2001). An alternative way to block cell signaling could be to interrupt the HSL synthesis by using analogs of HSL precursors.

However, the most promising possibility to block quorum sensing is to take advantage of the unique specificity the HSLs and HSL-receptor proteins show for one another. The ability of homoserine lactone-based analogs to inhibit activation of HSL-receptor proteins has already been demonstrated in a number of bacteria including *Vibrio fischeri* (Schaefer et al, *J. Bacteriol.* 178:2897-901, 1996), *Agrobacterium tumefaciens* (Zhu et al., *J. Bacteriol.* 180:5398-405, 1998), *Chromobacterium violaceum* (McLean et al., *Microbiology* 143:3703-11, 1997), *Aeromonas salmonicida* (Swift et al., *J. Bacteriol.* 179:5271-81, 1997) and *Pseudomonas aeruginosa* (Pesci et al., *J. Bacteriol.* 179:3127-32, 1997). However, none of these compounds have been developed as antimicrobial agents, e.g. in medical therapy, so far.

The are only few non-HSL-based antimicrobials described which are supposed to interfere specifically with HSL-regulated processes, for example halogenated furanone derivatives which are structurally similar to HSLs and have been isolated from red marine algae *Delisea pulchra* (WO 96/29392; Hentzer et al., *Microbiology* 148:87-102, 2002). Additionally, these substances have been demonstrated to inhibit also Gram-positive bacteria (WO 99/53915). However, the use of most of these furanone compounds is limited due to their toxicity making them unsuitable for veterinary and medical applications.

Futhermore, Smith et al. (*Chem. Biol.*, 10:81-9, 2003) recently published *Pseudomonas aeruginosa* HSL analogs with slight structural variations targeted to the HSL moiety which act both as quorum sensing agonists and antagonists. Additionally, WO 02/088298 reportedly provides certain nitrogen heterocyclic molecules for controlling biofilms based on the interference with quorum sensing.

Many target genes involved in biofilm formation, methods of screening for compounds to control biofilm development and HSL-based compositions to prevent biofilm formation have been described (WO 99/55368, WO 98/57618, WO 99/27786, WO 98/58075), but until now no promising antibacterial drug candidate has been developed that is capable of inhibiting virulence gene expression and biofilm formation in different areas, preferentially in the medical field.

It is an object of the present invention to provide compounds blocking specifically quorum sensing regulated processes without inhibiting bacterial growth, Furthermore, these compounds should not be structural derivatives of the homoserine lactone family of regulatory compounds and should not exhibit any toxic properties.

Accordingly, we have been able to find compounds that can significantly reduce virulence gene expression and biofilm formation of several human pathogens. In contrast to the furanones the compounds of this invention do not show any toxic effect and are therefore suitable for applications in a wide area. Such applications could be the use of the compounds for instance as new antibiotic therapeutics, disinfectants, antifouling coatings or coatings of medical devices. In contrast to traditional antibacterial agents (like amide or 1,2-acylhydrazine derivatives in WO 01/51456; for the synthesis of amide or 1,2-acylhydrazine derivatives see also EP 638545 and EP 982292), the compounds of the present invention do not kill the microorganisms, but render them avirulent. The advantage of this alternative strategy is that the emergence of bacterial resistance against such antimicrobials is extremely improbable.

SUMMARY OF THE INVENTION

In general, the present invention provides compounds selectively modulating bacterial cell-cell communication. Through inhibition of this communication system the expression of many HSL-dependent virulence genes and other phenotypes like swarming motility and biofilm formation are significantly reduced or completely abolished rendering a bacterial population more susceptible to the host immune-response or to treatment with traditional antibacterial agents.

Thus, in one aspect, the invention refers to a method for inhibiting an HSL-regulated process in a microorganism by exposing the microorganism to a new class of compounds with an inhibitory effect on bacterial signaling.

The present invention therefore refers to compounds of the general Formula (I)

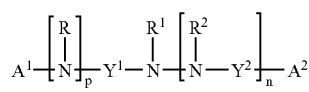

wherein
R is H, alkyl, cycloalkyl, aryl or heteroaryl;
$R^1$ is H, alkyl, cycloalkyl, aryl or heteroaryl;
$R^2$ is H, alkyl, cycloalkyl, aryl or heteroaryl;
$A^1$ and $A^2$ each independently represent an optionally substituted $C_1$-$C_{20}$-alkyl group which may contain one or more group(s) Z, or a monocyclic or polycyclic optionally substituted aromatic or non-aromatic ring system which may contain one or more group(s) X, and in case of a polycyclic ring system, said system contains at least one aromatic ring;

Z is selected from the group consisting of S, O, N, $NR^4$, CO, $CO_2$, CS, SO or $SO_2$ X is selected from the group consisting of S, O, N, $NR^4$, SO or $SO_2$;

said substituted ring system carries a substituent $R^3$ on one or more of the carbon atoms of said ring system;

said substituted $C_1$-$C_{20}$-alkyl group carries a substituent $R^3$ on one or more of the carbon atoms of said alkyl group;

$R^3$ is independently H, $OR^4$, $SR^4$, hydroxyalkyl, hydroxyalkylamino, cycloalkyl, halogen, haloalkyl, haloalkyloxy, $NO_2$, CN, $SO_2NR^4R^5$, $CO_2NR^4R^5$, $COR^4$, $CO_2R^4$, $SO_2R^4$, $SO_3R^4$, $NR^4R^5$, alkyl, aryl or heteroaryl;

$R^{3'}$ is independently H, $OR^4$, $SR^4$, hydroxyalkyl, hydroxyalkylamino, cycloalkyl, halogen, haloalkyl, haloalkyloxy, $NO_2$, CN, $SO_2NR^4R^5$, $CO_2NR^4R^5$, $COR^4$, $CO_2R^4$, $SO_2R^4$, $SO_3R^4$, $NR^4R^5$, alkyl, aryl or heteroaryl;

$R^{3''}$ is independently H, $OR^4$, $SR^4$, hydroxyalkyl, hydroxyalkylamino, cycloalkyl, halogen, haloalkyl, haloalkyloxy, $NO_2$, CN, $SO_2NR^4R^5$, $CO_2NR^4R^5$, $COR^4$, $CO_2R^4$, $SO_2R^4$, $SO_3R^4$, $NR^4R^5$, alkyl, aryl or heteroaryl;

$R^4$ is H, alkyl, cycloalkyl, aryl or heteroaryl;

$R^5$ is H, O-alkyl, O-aryl, alkyl, heteroaryl or aryl;

$Y^1$ and $Y^2$ are independent from each other C=O, C=S, $SO_2$ or C=$NR^5$;

p is 0, n is 0;
or p is 0, n is 1;
or p is 1, n is 0;
or p is 1, n is 1;

In Formula (I) the following definitions are used:

an alkyl group, if not stated otherwise, denotes a linear or branched $C_1$-$C_6$-alkyl, preferably a linear or branched chain of one to five carbon atoms, a linear or branched $C_1$-$C_6$-alkenyl or a linear or branched $C_1$-$C_6$-alkinyl group, which can optionally be substituted by one or more substituents $R^3$, preferably by halogen;

the $C_1$-$C_6$-alkyl $C_1$-$C_6$-alkenyl and $C_1$-$C_6$-alkinyl residue may be selected from the group comprising —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —$C_6H_{13}$, —C($R_3$)$^3$, —$CR^3(R^{3'})_3$, —$CR^3(R^{3'})R^{3''}$, —$C_2(R^3)_5$, —$CH_2$—C($R^3$)$_3$, —$CH_2$—$CR^3(R^{3'})_2$, —$CH_2$—$CR^3(R^{3'})R^{3''}$, —$C_3(R^3)_7$, —$C_2H_4$—C($R^3$)$_3$, —$C_2H_4$—CH=$CH_2$, —CH=CH—$C_2H_5$, —CH=C($CH_3$)$_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH=$CH_2$, —CH=CH—$C_3H_7$, —$C_2H_4$—CH=CH—$CH_3$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$CH_2$—CH=C($CH_3$)$_2$, —C($CH_3$)=C($CH_3$)$_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH =$CH_2$, —CH=CH—C($CH_3$)=$CH_2$, —CH=CH—C($CH_3$)=$CH_2$, —C($CH_3$)=CH—C≡CH, —CH=C($CH_3$)—C≡CH, —C≡C—C($CH_3$)=$CH_2$, —$C_3H_6$—CH($CH_3$)$_2$, —$C_2H_4$—(CH$_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3$)$_2$, —$C_2H_4$—CH=C($CH_3$)$_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$;

a cycloalkyl group denotes a non-aromatic ring system containing three to eight carbon atoms, preferably four to eight carbon atoms, wherein one or more of the carbon atoms in the ring can be substituted by a group X, X being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$;

an alkoxy group denotes an O-alkyl group, the alkyl group being as defined above; the alkoxy group is preferably a methoxy, ethoxy, isopropoxy, t-butoxy or pentoxy group; an haloalkyl group denotes an alkyl group which is substituted by one to five halogen atoms, the alkyl group being as defined above; the haloalkyl group is preferably a —C($R^{10}$)$_3$, —$CR^{10}(R^{10'})_2$, —$CR^{10}(R^{10'})R^{10''}$, —$C_2(R^{10})_5$, —$CH_2$—C($R^{10}$)$_3$, —$CH_2$—$CR^{10}(R^{10'})_2$, —$CH_2$—$CR^{10}(R^{10'})R^{10''}$, —$C_3(R^{10})_7$ or —$C_2H_4$—C($R^{10}$)$_3$, wherein $R^{10}$, $R^{10'}$, $R^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC($R^{10}$)$_3$, —$OCR^{10}(R^{10'})_2$, —$OCR^{10}(R^{10'})R^{10''}$, —$OC_2(R^{10})_5$, —$OCH_2$—C($R^{10}$)$_3$, —$OCH_2$—$CR^{10}(R^{10'})_2$, —$OCH_2$—$CR^{10}(R^{10'})R^{10''}$, —$OC_3(R^{10})_7$ or —$OC_2H_4$—C($R^{10}$)$_3$, wherein $R^{10}$, $R^{10'}$, $R^{10''}$ represent F, Cl, Br or I, preferably F;

a hydroxyalkylamino group denotes an (HO-alkyl)$_2$-N- group or HO-alkyl-NH- group, the alkyl group being as defined above;

a halogen group is chlorine, bromine, fluorine or iodine;

an aryl group preferably denotes an aromatic group having five to fifteen carbon atoms, which can optionally be substituted by one or more substituents $R^3$, where $R^3$ is as defined above; the aryl group is preferably a phenyl group, —$CH_2$—$C_6H_4$, —$C_2H_4$—$C_6H_4$, —CH=CH—$C_6H_4$, —C≡C—$C_6H_4$, -o-$C_6H_4$—$R^3$, -m-$C_{64}$—$R^3$, -p-$C_6H_4R^3$, -o-$CH_2$—$C_6H_4$—$R^3$, -m-$CH_2$—$C_6H_4$—$R^3$, -p-$CH_2$—$C_6H_4$—$R^3$;

a heteroaryl group denotes a 5- or 6-membered heterocyclic group which contains at least one heteroatom like O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol- 5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydro-quinolinyl, isoquinolinyl, tetrahydroisoquinolinyl group. This heterocyclic group can optionally be substituted by one or more substituents $R^3$, where $R^3$ is as defined above.

In Formula (I), $A^1$ or $A^2$ each independently represent a $C_1$-$C_{20}$-alkyl group which is optionally substituted by one or more substituents $R^3$, or a monocyclic or polycyclic aromatic or non-aromatic ring system which is optionally substituted by one or more substituents $R^3$ and in case of an aromatic ring system contains at least one aromatic ring. The optionally substituted monocyclic or polycyclic aromatic or non-aromatic ring system may also contain one or more groups X selected from S, O, N, $NR^4$, SO or $SO_2$. In preferred embodiments, $A^1$ and $A^2$ each independently represent an optionally substituted $C_1$-$C_{20}$-alkyl group or an optionally substituted monocyclic or bicyclic aromatic ring system. In case of substitutions of carbon atoms in the ring system, preferably one, two or three carbon atoms am substituted by a group X, wherein X is selected from the group consisting of S, O, N, $NR^4$, SO or $SO_2$. In one preferred embodiment, one of the carbon atoms is substituted by a group X=O, S, NH.

In Formula (I), $A^1$ and/or $A^2$ independently represent an optionally substituted $C_1$-$C_{20}$-alkyl group which is optionally substituted by one or more substituents $R^3$. Preferably $A^1$ and/or $A^2$ independently represent an optionally substituted $C_1$-$C_{12}$-alkyl group, said alkyl group may be a straight chain or branched chain alkyl group, and examples include methyl, ethyl, propyl, isopropyl, butyl, t-butyl, isobutyl, pentyl, hexyl, heptyl, octyl, nonyl, decyl, undecyl and dodecyl groups. The term alkyl group also contains alkenyl and alkinyl groups, that means that the alkyl group contains one or more double or triple bounds.

In Formula (I), $A^1$ and/or $A^2$ represent an optionally aromatic or non-aromatic ring system, which is substituted by one or more substituents $R^3$, said ring system may be a phenyl, 1-naphthyl, 2-napthyl, 1-anthracenyl, 2-anthracenyl, 2-pyranyl, 3-pyranyl, 4-pyranyl, 2-thiazolyl, 4-thiazolyl, 5-thiazolyl, 2-oxazolyl, 4-oxazolyl and 5-oxazolyl, in particular 3-pyrazolyl, 4-pyrazolyl, 5-pyrazolyl, 2-pyrazinyl, 3-pyrazinyl, 1-imidazolyl, 2-imidazolyl, 2-thienyl, 3-thienyl, 2-furyl, 3-furyl, 2-pyridyl, 3-pyridyl, 4-pyridyl, benzothiophene, pyrazolo[3,4-b]-pyridyl, 2-pyrimidyl, 4-pyrimidyl and 9H-thioxanthene-10,10-dioxide ring, in which the ring system can be fused to one or more other monocyclic aromatic or non-aromatic rings.

Suitable substituents for $A^1$ and/or $A^2$ are independently H, $CO_2R^4$, $COR^4$, $CONR^4R^5$, $NR^4R^5$, $OR^4$, $SR^4$, hydroxyalkylamino, $NO_2$, CN, hydroxylalkyl, halogen, haloalkyl, haloalkyloxy, $SO_2NR^4R^5$, $CO_2NR^4R^5$, $CO_2R^4$, $SO_2R^4$, $SO_3R^4$, $NR^4R^5$, alkyl, cycloalkyl, arylalkyl, aryl or heteroaryl.

Furthermore the present invention is directed to novel compounds of the general Formula (X) and pharmaceutically acceptable salts thereof:

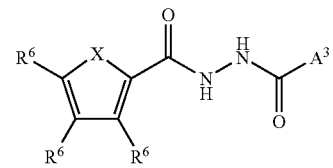

wherein
$A^3$ is an optionally substitued $C_3$-$C_{20}$-alkyl group or

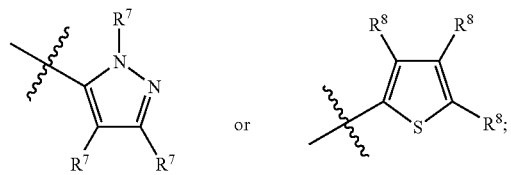

an $C_3$-$C_{20}$-alkyl group denotes a linear or branched $C_3$-$C_{20}$-alkyl group, which is optionally substituted by $R^3$, $R^3$ being as defined below; the $C_3$-$C_{20}$-alkyl residue may be selected from the group comprising —$C_3H_7$, —$CH(CH_3)_2$, —$C_4H_9$, —$CH_2$—$CH(CH_3)_2$, —$CH(CH_3)$—$C_2H_5$, —$CH_2$—$CH(CH_3)$—$CH_3$, —$C(CH_3)_3$, —$C_5H_{11}$, —$C_2H_4$—$CH(CH_3)_2$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2CH(CH_3)_2$, —$C_2H_4$—$C(CH_3)_3$, —$CH(CH_3)$—$C(CH_3)_3$, —$C_7H_{15}$, —$C_3H_6$—$C(CH_3)_3$, —$C_4H_8$—$CH(CH_3)_2$, —$C_3H_6$—$CH(CH_3)$—$C_2H_5$, —$C_2H_4$—$C(CH_3)_2$—$C_2H_5$, —$C_2H_4$—$CH(CH_3)$—$C_3H_7$, —$CH_2$—$C(CH_3)_2$—$C_3H_7$, —$CH_2$—$CH(CH_3)$—$C_4H_9$, —$CH(CH_3)$—$C_5H_{11}$, —$C(CH_3)_2$—$C(CH_3)_2$—$CH_3$, —$C(CH_3)_2$—$CH_2$—$CH(CH_3)_2$, —$CH(CH_3)$—$C_2H_4$—$CH(CH_3)_2$, —$CH_2$—$CH(CH_3)$—$CH_2$—$CH(CH_3)_2$, —$CH_2$—$C(CH_3)_2$—$CH(CH_3)_2$, —$CH(CH_3)$—$CH_2$—$C(CH_3)_3$, —$CH_2$—$CH(CH_3)$—$C(CH_3)_3$, —$C_8H_{17}$, —$C_4H_8$—$C(CH_3)_3$, —$C_5H_{10}$—$CH(CH_3)_2$, —$C_4H_8$—$CH(CH_3)$—$C_2H_5$, —$C_3H_6$—$C(CH_3)_2$—$C_2H_5$, —$C_3H_6$—$CH(CH_3)$—$C_3H_7$, —$C_2H_4$—$C(CH_3)_2$—$C_3H_7$, —$C_2H_4$—$CH(CH_3)$—$C_4H_9$, —$CH_2$—$C(CH_3)_2$—$C_4H_9$) —$CH_2$—$CH(CH_3)$—$C_5H_{11}$, —$C(CH_3)_2$—$C_5H_{11}$, —$CH(CH_3)$—$C_6H_{13}$, —$C_9H_{19}$, —$C_5H_{10}$—$C(CH_3)_3$, —$C_6H_{12}$—$CH(CH_3)_2$, —$C_5H_{10}$—$CH(CH_3)$—$C_2H_5$, —$C_4H_8$—$C(CH_3)_2$—$C_2H_5$, —$C_4H_8$—$C(CH_3)$—$C_3H_7$, —$C_3H_6$—$C(CH_3)_2$—$C_3H_7$, —$C_3H_6$—$CH(CH_3)$—$C_4H_9$, —$C_2H_4$—$C(CH_3)_2$—$C_4H_9$, —$C_2H_4$—$CH(CH_3)$—$C_5H_{11}$, —$CH_2$—$C(CH_3)_2$—$C_5H_{11}$, —$CH_2$—$CH(CH_3)$—$C_6H_{13}$, —$C(CH_3)_2$—$C_6H_{13}$, —$CH(CH_3)$—$C_7H_{15}$, —$C_{10}H_{21}$, —$C_6H_{12}$—$C(CH_3)_3$, —$C_7H_{14}$—$CH(CH_3)_2$, —$C_6H_{12}$—$CH(CH_3)$—$C_2H_5$, —$C_5H_{10}$—$C(CH_3)_2$—$C_2H_5$, —$C_5H_{10}$—$CH(CH_3)$—$C_3H_7$, —$C_4H_8$—$C(CH_3)_2$—$C_3H_7$, —$C_4H_8$—$CH(CH_3)$—$C_4H_9$, —$C_3H_6$—$C(CH_3)_2$—$C_4H_9$, —$C_3H_6$—$CH(CH_3)$—$C_5H_{11}$, —$C_2H_4$—$C(CH_3)_2$—$C_5H_{11}$, —$C_2H_4$—$CH(CH_3)$—$C_6H_{13}$, —$CH_2$—$C(CH_3)_2$—$C_6H_{13}$, —$CH_2$—$CH(CH_3)$—$C_7H_{15}$, —$C(CH_3)_2$—

$C_7H_{15}$, —CH(CH$_3$)—C$_8$H$_{17}$, —C$_{11}$H$_{23}$, —C$_7$H$_{14}$—C(CH$_3$)$_3$, —C$_8$H$_{16}$—CH(CH$_3$)$_2$, —C$_7$H$_{14}$—CH(CH$_3$)—C$_2$H$_5$, —C$_6$H$_{12}$—C(CH$_3$)$_2$—C$_2$H$_5$, —C$_6$H$_{12}$—CH(CH$_3$)—C$_3$H$_7$, —C$_5$H$_{10}$—C(CH$_3$)$_2$—C$_3$H$_7$, —C$_5$H$_{10}$—CH(CH$_3$)—C$_4$H$_9$, —C$_4$H$_8$—C(CH$_3$)$_2$—C$_4$H$_9$, —C$_4$H$_8$—CH(CH$_3$)—C$_5$H$_{11}$, —C$_3$H$_6$—C(CH$_3$)$_2$—C$_5$H$_{11}$, —C$_3$H$_6$—CH(CH$_3$)—C$_6$H$_{13}$, —C$_2$H$_4$—C(CH$_3$)$_2$—C$_6$H$_{13}$, —C$_2$H$_4$—CH(CH$_3$)—C$_7$H$_{15}$, —CH$_2$—C(CH$_3$)$_2$—C$_7$H$_{15}$, —CH$_2$—CH(CH$_3$)—C$_8$H$_{17}$, —C(CH$_3$)$_2$—C$_8$H$_{17}$, —CH(CH$_3$)—C$_9$H$_{19}$, —C$_{12}$H$_{25}$, —C$_8$H$_{16}$—C(CH$_3$)$_3$, —C$_9$H$_{18}$—CH(CH$_3$)$_2$, —C$_8$H$_{16}$—CH(CH$_3$)—C$_2$H$_5$, —C$_7$H$_{14}$—C(CH$_3$)$_2$—C$_2$H$_5$, —C$_7$H$_{14}$—CH(CH$_3$)—C$_3$H$_7$, —C$_6$H$_{12}$—C(CH$_3$)$_2$—C$_3$H$_7$, —C$_6$H$_{12}$—CH(CH$_3$)—C$_4$H$_9$, —C$_5$H$_{10}$—C(CH$_3$)$_2$—C$_4$H$_9$, —C$_5$H$_{10}$—CH(CH$_3$)—C$_5$H$_{11}$, —C$_4$H$_8$—C(CH$_3$)$_2$—C$_5$H$_{11}$, —C$_4$H$_8$—CH(CH$_3$)—C$_6$H$_{13}$, —C$_3$H$_6$—C(CH$_3$)$_2$—C$_6$H$_{13}$, —C$_3$H$_6$—CH(CH$_3$)—C$_7$H$_{15}$, —C$_2$H$_4$—C(CH$_3$)$_2$—C$_7$H$_{15}$, —C$_2$H$_4$—CH(CH$_3$)—C$_8$H$_{17}$, —CH$_2$—C(CH$_3$)$_2$—C$_8$H$_{17}$, —CH$_2$—CH(CH$_3$)—C$_9$H$_{19}$, —C(CH$_3$)$_2$—C$_9$H$_{19}$, —CH(CH$_3$)—C$_{10}$H$_{21}$;

$R^6$ is independently of each other —H, —F, —Cl, —Br, —I, —NO$_2$, —NR$^4$R$^5$, —CN, alkyl, cycloalkyl, —OH, alkoxy, alkylthio, hydroxyalkylamino, haloalkyl, haloalkyloxy, hydroxyalkyl, aryl or heteroaryl;

$R^7$ is independently of each other —H, —F, —Cl, —Br, —I, —NO$_2$, —NR$^4$R$^5$, —CN, alkyl, cycloalkyl, —OH, alkoxy, alkylthio, hydroxyalkylamino, haloalkyl, haloalkyloxy, hydroxyalkyl, aryl or heteroaryl, $R^8$ is independently of each other —H, —F, —Cl, —Br, —I, —NO$_2$, —NR$^4$R$^5$, —CN, alkyl, cycloalkyl, —OH, alkoxy, alkylthio, hydroxyalkylamino, haloalkyl, haloalkyloxy, hydroxyalkyl, aryl or heteroaryl;

X is selected from the group consisting of S, O, N, NR$^4$, SO or SO$_2$;

$R^4$ is H, alkyl, cycloalkyl, aryl or heteroaryl;

$R^5$ is H, O-alkyl, O-aryl, alkyl, heteroaryl or aryl;

$R^3$, $R^{3'}$ or $R^{3''}$ are independently H, OR$^4$, SR$^4$, hydroxyalkyl, hydroxyalkylamino, cycloalkyl, halogen, haloalkyl, haloalkyloxy, NO$_2$, CN, SO$_2$NR$^4$R$^5$, CO$_2$NR$^4$R$^5$, COR$^4$, CO$_2$R$^4$, SO$_2$R$^4$, SO$_3$R$^4$, NR$^4$R$^5$, alkyl aryl or heteroaryl; with R$^4$, R$^5$ being as defined above;

an alkyl group, if not stated otherwise, denotes a linear or branched $C_1$-$C_6$-alkyl, preferably a linear or branched chain of one to five carbon atoms, a linear or branched $C_1$-$C_6$-alkenyl or a linear or branched $C_1$-$C_6$-alkinyl group, which can optionally be substituted by one or more substituents R$^3$, preferably by halogen;

the $C_1$-$C_6$-alkyl, $C_1$-$C_6$-alkenyl and $C_1$-$C_6$-alkinyl residue may be selected from the group comprising —CH$_3$, —C$_2$H$_5$, —CH=CH$_2$, —C≡CH, —C$_3$H$_7$, —CH(CH$_3$)$_2$, —CH$_2$—CH=CH$_2$, —C(CH$_3$)=CH$_2$, —CH=CH—CH$_3$, —C≡C—CH$_3$, —CH$_2$—C≡CH, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C(R$^3$)$_3$, —CR$_3$(R$^{3'}$)$_2$, —CR$^3$(R$^{3'}$)R$^{3''}$, —C$_2$(R$^3$)$_5$, —CH$_2$—C(R$^3$)$_3$, —CH$_2$—CR$^3$(R$^{3'}$)$_2$, —CH$_2$—CR$^3$(R$^{3'}$)R$^{3''}$, —C$_3$(R$^3$)$_7$, —C$_2$H$_4$—C(R$^3$)$_3$, —C$_2$H$_4$—CH=CH$_2$, —CH=CH—C$_2$H$_5$, —CH=C(CH$_3$)$_2$, —CH$_2$—CH=CH—CH$_3$, —CH=CH—CH=CH$_2$, —C$_2$H$_4$—C≡CH, —C≡C—C$_2$H$_5$, —CH$_2$—C≡C—CH$_3$, —C≡C—CH$_2$, —CH=CH—C≡CH, —C≡C—C≡CH, —C$_2$H$_4$—CH(CH$_3$), —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH=CH$_2$, —CH=CH—CH=CH—CH$_3$, —CH=CH—CH=CH—CH$_2$, —C(CH$_3$)=CH—CH=CH$_2$, —CH=C(CH$_3$)—CH=CH$_2$, —CH=CH—C(CH$_3$)=CH$_2$, —CH$_2$—CH=C(CH$_3$)$_2$, —C(CH$_3$)=C(CH$_3$)$_2$, —C$_3$H$_6$—C≡CH, —C≡C—C$_3$H$_7$, —C$_2$H$_4$—C≡C—CH$_3$, —CH$_2$—C≡C—C$_2$H$_5$, —CH$_2$—C≡C—CH=CH$_2$, —CH$_2$—CH=CH—C≡CH, —CH$_2$—C≡C—C≡CH, —C≡C—CH=CH—CH$_3$, —CH=CH—C≡C—CH$_3$, —C≡C—C≡C—CH$_3$, —C≡C—CH$_2$—CH=CH$_2$, —CH=CH—CH$_2$—C≡CH, —C≡C—CH$_2$—C≡CH, —C(CH$_3$)=CH—CH=CH$_2$, —CH=C(CH$_3$)—CH=CH$_2$, —CH=CH—C(CH$_3$)=CH$_2$, —C(CH$_3$)=CH—C≡CH, —CH=C(CH$_3$)—C≡CH, —C≡C—C(CH$_3$)=CH$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH=CH$_2$, —CH=CH—C$_4$H$_9$, —C$_3$H$_6$—CH=CH—CH$_3$, —CH$_2$—CH=CH—C$_3$H$_7$, —C$_2$H$_4$—CH=CH—C$_2$H$_5$, —CH$_2$—C(CH$_3$)=C(CH$_3$)$_2$, —C$_2$H$_4$—CH=C(CH$_3$)$_2$, —C$_4$H$_8$—C≡CH, —C≡C—C$_4$H$_9$, —C$_3$H$_6$—C≡C—CH$_3$, —CH$_2$—C≡C—C$_3$H$_7$, —C$_2$H$_4$—C≡C—C$_2$H$_5$;

a cycloalkyl group denotes a non-aromatic ring system containing three to eight carbon atoms, preferably four to eight carbon atoms, wherein one or more of the carbon atoms in the ring can be substituted by a group X, X being as defined above; the $C_3$-$C_8$-cycloalkyl residue may be selected from the group comprising -cyclo-C$_3$-H$_5$, -cyclo-C$_4$H$_7$, -cyclo-C$_5$H$_9$, -cyclo-C$_6$H$_{11}$, -cyclo-C$_7$H$_{13}$, -cyclo-C$_8$H$_{15}$;

an alkoxy group denotes an O-alkyl group, the alkyl group being as defined above; the alkoxy group is preferably a methoxy, ethoxy, isopropoxy, t-butoxy or pentoxy group.

an haloalkyl group denotes an alkyl group which is substituted by one to five halogen atoms, the alkyl group being as defined above; the haloalkyl group is preferably a —C(R$^{10}$)$_3$, —CR$^{10}$(R$^{10'}$)$_2$, —CR$^{10}$(R$^{10'}$)R$^{10''}$, —C$_2$(R$^{10}$)$_5$, —CH$_2$—C(R$^{10}$)$_3$, —CH$_2$—CR$^{10}$(R$^{10'}$)$_2$, —CH$_2$—CR$^{10}$(R$^{10'}$)R$^{10''}$, —C$_3$(R$^{10}$)$_7$ or —C$_2$H$_4$—C(R$^{10}$)$_3$, wherein R$^{10}$, R$^{10'}$, R$^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC(R$^{10}$)$_3$, —OCR$^{10}$(R$^{10'}$)$_2$, —OCR$^{10}$(R$^{10'}$)R$^{10''}$, —OC$_2$(R$^{10}$)$_5$, —OCH$_2$—C(R$^{10}$)$_3$, —OCH$_2$—CR$^{10}$(R$^{10'}$)$_2$, —OCH$_2$—CR$^{10}$(R$^{10'}$)R$^{10''}$, —OC$_3$(R$^{10}$)$_7$ or —OC$_2$H$_4$—C(R$^{10}$)$_3$, wherein R$^{10}$, R$^{10'}$, R$^{10''}$ represent F, Cl, Br or I, preferably F;

a hydroxyalkylamino group denotes an (HO-alkyl)$_2$-N-group or HO-alkyl-NH- group, the alkyl group being as defined above;

a halogen group is chlorine, bromine, fluorine or iodine;

an aryl group preferably denotes an aromatic group having five to fifteen carbon atoms, which can optionally be substituted by one or more substituents R$^3$, where R$^3$ is as defined above, the aryl group is preferably a phenyl group, —CH$_2$—C$_6$H$_4$, —C$_2$H$_4$—C$_6$H$_4$, —CH=CH—C$_6$H$_4$, —C≡C—C$_6$H$_4$, -o-C$_6$H$_4$—R$^3$, -m-C$_6$H$_4$—R$^3$, -p-C$_6$H$_4$—R$^3$, -o-CH$_2$—C$_6$H$_4$R$^3$, -m-CH$_2$—C$_6$H$_4$—R$^3$, -p-CH$_2$—C$_6$H$_4$—R$^3$;

a heteroaryl group denotes a 5- or 6-membered heterocyclic group which contains at least one heteroatom like O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl group. This heterocyclic group can optionally be substituted by one or more substituents R$^3$, where R$^3$ is as defined above.

However, the following compounds are excluded from Formula (X):

2-thiophenecarboxylic acid-5-nitro-2-(2-thienylcarbonyl) hydrazide, 4butylthiophene-2-carboxylic acid-N'-(4-butyl-thiophen-2-carbonyl)hydrazide, 2-thiophenecarboxylic acid-3-chloro-2-(2-thienylcarbonyl)hydrazide, 2-thiophene carboxylic acid-5-bromo-2-(2-thienylcarbonyl)hydrazide, 1H-pyrazole-5-carboxylic acid-1-methyl-2-(2-thienylcarbonyl)hydrazide, 2-thiophenecarboxylic acid-5-(4,5,6,7-tetrahydro-benzo[b]thien-2yl)-2-[[5-(4,5,6,7-tertahydrobenzo[b]thien-2-yl)-2-thienyl]-carbonyl]-hydrazide, 1H-pyrrole-2-carboxylic acid-2-(2-thienylcarbonyl)hydrazide, 2-thiophenecarboxylic acid-2-(2-thienylcarbonyl)-hydrazide, 2-thiophenecarboxylic acid N'-(furan-2-carbonyl)hydrazide, 2-thiophenecarboxylic acid-N'-(5-bromofuran-2carbonyl)hydrazide, 1H-pyrazole-3-carboxylic acid-4bromo-1,5-dimethyl-2-(2-thienylcarbonyl)hydrazide, thiophene-2-carboxylic acid N'-(3-chloro-4-methylthiophene-2-carbonyl)hydrazide and 2-furancarboxylic acid-5-[[[4-methyl-6-(trifluoromethyl)-2-pyrimidinyl]thio]methyl]-2-(2-thienylcarbonyl) hydrazide.

Furthermore the present invention is directed to novel compounds of the general Formula (X) and pharmaceutically acceptable salts thereof:

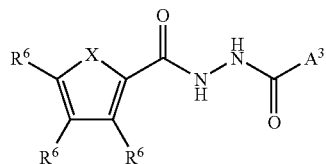

wherein
A$^3$ is an optionally substitued C$_3$-C$_{20}$-alkyl group or

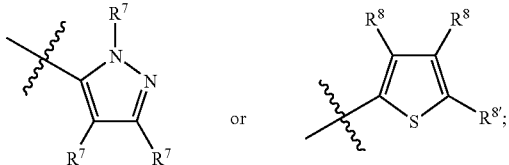

with the C$_3$-C$_{20}$-alkyl group being as defined above for Formula (X)

R$^3$ is defined as above in Formula (X)
R$^4$ is defined as above in Formula (X)
R$^5$ is defined as above in Formula (X)
R$^6$ is independently of each other —H, —F, —Cl, —Br, —I, —NR$^4$R$^5$, C$_1$-C$_3$-alkyl, alkoxy, alkylthio, hydroxyalkylamino, —CN, —NO$_2$, —OH, haloalkyl, haloalkyloxy, hydroxyalkyl, aryl or heteroaryl;

said C$_1$-C$_3$-alkyl of R$^6$ denotes a linear or branched C$_1$-C$_3$-alkyl, a linear or branched C$_1$-C$_3$-alkenyl or a linear or branched C$_1$-C$_3$-alkinyl group, which can optionally be substituted by one or more substituents R', preferably by halogen; the C$_1$-C$_3$-alkyl, C$_1$-C$_3$-alkenyl and C$_1$-C$_3$-alkinyl residue may be selected from the group comprising —CH$_3$, —C$_2$H$_5$, —CH=CH$_2$, —C≡CH, —C$_3$H$_7$, —CH(CH$_3$)$_2$, —C≡C—CH$_3$, —CH$_2$—C≡CH;

R' is independently H, OR$^4$, hydroxyalkyl, hydroxyalkylamino, cycloalkyl, halogen, haloalkyl, haloalkyloxy, NO$_2$, CN, SO$_2$NR$^4$R$^5$, CO$_2$NR$^4$R$^5$, COR$^4$, CO$_2$R$^4$, SO$_2$R$^4$, SO$_3$R$^4$, NR$^4$R$^5$, alkyl, aryl or heteroaryl;

R$^7$ is independently of each other —H, —F, —Cl, —I, —NO$_2$, —NR$^4$R$^5$, —CN, C$_2$-C$_6$-alkyl, cycloalkyl, —OH, alkoxy, alkylthio, hydroxyalkylamino, haloalkyl, haloalkyloxy, hydroxyalkyl, aryl or heteroaryl;

said C$_2$-C$_6$-alkyl of R$^7$, denotes a linear or branched C$_2$-C$_6$-alkyl, a linear or branched C$_2$-C$_6$-alkenyl or a linear or branched C$_2$-C$_6$-alkinyl group, which can optionally be substituted by one or more substituents R$^3$, preferably by halogen; the C$_2$-C$_6$-alkyl, C$_2$-C$_6$-alkenyl and C$_2$-C$_6$-alkinyl residue may be selected from the group comprising —C$_2$H$_5$, —CH=CH$_2$, —C≡CH, —C$_3$H$_7$, —CH(CH$_3$)$_2$, —C≡C—CH$_3$, —CH$_2$—C≡CH, —CH$_2$—CH=CH$_2$, —C(CH$_3$)=CH$_2$, —CH=CH—CH$_3$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C(R$^3$)$_3$, —CR$^3$(R$^{3'}$)$_2$, —CR$^3$(R$^{3'}$)R", —C$_2$(R$^3$)$_5$, —CH$_2$—C(R$^3$)$_3$, —CH$_2$—CR$^3$(R$^{3'}$)$_2$, —CH$_2$—CR$^3$(R$^{3'}$)R"', —C$_3$(R$^3$)$_7$, —C$_2$H$_4$—C(R$^3$)$_3$, —C$_2$H$_4$—CH=CH$_2$, —CH=CH—C$_2$H$_5$, —CH=C(CH$_3$)$_2$, —CH$_2$—CH=CH—CH$_3$, —CH=CH—CH=CH$_2$, —C$_2$H$_4$—C≡CH, —C≡C—C$_2$H$_5$, —CH$_2$—C≡C—CH$_3$, —C≡C—CH=CH$_2$, —CH=CH—C≡CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH=CH$_2$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —CH$_2$—

CH=C(CH₃)₂, —C(CH₃)=C(CH₃)₂, —C₃H₆—C=CH, —C≡C—C₃H₇, —C₂H₄—C≡C—CH₃, —CH₂—C≡C—C₂H₅, —CH₂—C≡C—CH=CH₂, —CH₂—CH=CH—C≡CH, —CH₂—C≡C—C≡CH, —C≡C—CH=CH—CH₃, —CH=CH—C≡C—CH₃, —C≡C—C≡C—CH₃, —C≡C—CH₂—CH=CH₂, —CH=CH—CH₂—C≡CH, —C≡C—CH₂—C≡CH, —C(CH₃)=CH—CH=CH₂, —CH=C(CH₃)—CH=CH₂, —CH=CH—C(CH₃)—CH₂, —C(CH₃)=CH—C≡CH, —CH=C(CH₃)—C≡CH, —C≡C—C(CH₃)=CH₂, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —C₄H₈—CH=CH₂, —CH=CH—C₄H₉, —C₃H₆—CH=CH—CH₃, —CH₂—CH=CH—C₃H₇, —C₂H₄—CH=CH—C₂H₅, —CH₂—C(CH₃)=C(CH₃)₂, —C₂H₄—CH=C(CH₃)₂, —C₄H₈—C≡CH, —C≡C—C₄H₉, —C₃H₆—C≡C—CH₃, —CH₂—C≡C—C₃H₇, —C₂H₄—C≡C—C₂H₅;

R³, R³' or R³'' are defined as above in Formula (X)

R⁴, R⁵ are defined as above in Formula (X);

R⁸ is independently of each other —H, 'F, —I, —NR⁴R⁵, —CN, C₁-C₃-alkyl, —OH, alkoxy, alkylthio, hydroxyalkylamino, haloalkyl, haloalkyloxy, hydroxyalkyl, aryl or heteroaryl;

said C₁-C₃-alkyl of R⁸, denotes a linear or branched C₁-C₃-alkyl, a linear or branched C₁-C₃-alkenyl or a linear or branched C₁-C₃-alkinyl group, which can optionally be substituted by one or more substituents R', preferably by halogen; the C₁-C₃-alkyl, C₁-C₃-alkenyl and C₁-C₃-alkinyl residue may be selected from the group comprising —CH₃, —C₂H₅, —CH=CH₂, C≡CH, —C₃H₇, —CH(CH₃)₂, —C≡C—CH₃, —CH₂—C≡CH;

R' is defined as above in Formula (X);

R⁴, R⁵ are defined as above in Formula (X);

R⁸' is independently of each other —F, —I, —NR⁴R⁵, —CN, C₁-C₃-alkyl, —OH, alkoxy, alkylthio, hydroxyalkylamino, haloalkyl, haloalkyloxy, hydroxyalkyl, aryl or heteroaryl;

said C₁-C₃-alkyl of R⁸', denotes a linear or branched C₁-C₃-alkyl, a linear or branched C₁-C₃-alkenyl or a linear or branched C₁-C₃-alkinyl group, which can optionally be substituted by one or more substituents R', preferably by halogen; the C₁-C₃-alkyl, C₁-C₃-alkenyl and C₁-C₃-alkinyl residue may be selected from the group comprising —CH₃, —C₂H₅, —CH=CH₂, —C≡CH, —C₃H₇, —CH(CH₃)₂, —C≡C—CH₃, —CH₂—C≡CH;

R' is defined as above in Formula (X);

an alkyl group, referring to R³, R³', R³'', R⁴ or R⁵ denotes a linear or branched C₁-C₆-alkyl, preferably a linear or branched chain of 1 to 5 carbon atoms, a linear or branched C₁-C₆-alkenyl or a linear or branched C₁-C₆-alkinyl group, which can optionally be substituted by one or more substituents R³, preferably by halogen;

the C₁-C₆-alkyl, C₁-C₆-alkenyl and C₁-C₆-alkinyl residue may be selected from the group comprising —CH₃, —C₂H₅, —CH=CH₂, —C≡CH, —C₃H₇, —CH(CH₃)₂, —CH₂—CH=CH₂, —C(CH₃)=CH₂, —CH=CH—CH₃, —C≡C—CH₃, —CH₂—C≡CH, —C₄H₉, —CH₂—CH(CH₃)₂, —CH(CH₃)—C₂H₅, —C(CH₃)₃, —C₅H₁₁, —C₆H₁₃, —C(R³)₃, —CR³(R³')₂, —CR³(R³')R³'', —C₂(R³)₅, —CH₂—C(R³)₃, —CH₂—CR³(R³')₂, —CH₂—CR³(R³')R³'', —C₃(R³)₇, —C₂H₄—C(R³)₃, —C₂H₄—CH=CH₂, —CH=CH—C₂H₅, —CH₂—C(CH₃)₂, —CH₂—CH=CH—CH₃, —CH=CH—CH=CH₂, —C₂H₄—C≡CH, —C≡C—C₂H₅, —CH₂—C≡C—CH₃, —C≡C—CH=CH₂, —CH=CH—C≡CH, —C≡C—C≡CH, —C₂H₄—CH(CH₃)₂, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —C₃H₆—CH=CH₂, —CH=CH—C₃H₇, —C₂H₄—CH=CH—CH₃, —CH₂—CH=CH—C₂H₅, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —CH₂—CH=C(CH₃)₂, —C(CH₃)=C(CH₃)₂, —C₃H₆—C≡CH, —C≡C—C₃H₇, —C₂H₄—C≡C—CH₃, —CH₂—C≡C—C₂H₅, —CH₂—C≡C—CH=CH₂, —CH₂—CH=CH—C≡CH, —CH₂—C≡C—C≡CH, —C≡C—CH=CH—CH₃, —CH=CH—C≡C—CH₃, —C≡C—C≡C—CH₃, —C≡C—CH₂—CH=CH₂, —CH=CH—CH₂—C≡CH, —C≡C—CH₂—C≡CH, —C(CH₃)=CH—CH=CH₂, —CH=C(CH₃)—CH=CH₂, —CH=CH—C(CH₃)=CH₂, —C(CH₃)=CH—C≡CH, —CH=C(CH₃)—C≡CH, —C≡C—C(CH₃)=CH₂, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —C₄H₈—CH=CH₂, —CH=CH—C₄H₉, —C₃H₆—CH=CH—CH₃, —CH₂—CH=CH—C₃H₇, —C₂H₄—CH=CH—C₂H₅, —CH₂—C(CH₃)=C(CH₃)₂, —C₂H₄—CH=C(CH₃)₂, —C₄H₈—C≡CH, —C≡C—C₄H₉, —C₃H₆—C≡C—CH₃, —CH₂—C≡C—C₃H₇, —C₂H₄—C≡C—C₂H₅;

R³, R³' or R³'' are defined as above in Formula (X);

a cycloalkyl group is defined as above in Formula (X);

an alkoxy group is defined as above in Formula (X);

an haloalkyl is defined as above for in Formula (X);

a hydroxyalkyl group is defined as above in Formula (X);

an haloalkyloxy group is defined as above in Formula (X);

a hydroxyalkylamino group is defined as above in Formula (X);

a halogen group is defined as above in Formula (X);

an aryl group is defined as above in Formula (X);

a heteroaryl group is defined as above in Formula (X).

Furthermore the present invention is directed to novel compounds of the general Formula (XI) and pharmaceutically acceptable salts thereof:

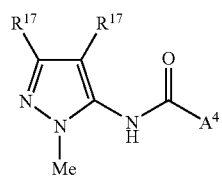

wherein
- $A^4$ is an optionally substituted $C_2$-$C_{20}$-alkyl or a 5-membered heteroaryl group, which contains at least one heteroatom like O, N, S, $NR^4$, SO, $SO_2$, Se; which can optionally be substituted by one or more substituents $R^3$;
- $R^3$ is independently H, $OR^4$, $SR^4$, hydroxyalkyl, hydroxyalkylamino, cycloalkyl, halogen, haloalkyl, haloalkyloxy, $NO_2$, CN, $SO_2NR^4R^5$, $CO_2NR^4R^5$, $COR_4$, $CO_2R^4$, $SO_2R^4$, $SO_3R^4$, $NR^4R^5$, alkyl, aryl or heteroaryl;
- $R^4$ is H, alkyl, cycloalkyl, aryl or heteroaryl;
- $R^5$ is H, O-alkyl, O-aryl, alkyl, heteroaryl or aryl;
- $R^{17}$ is independently of each other —H, —F, —Cl, —I, —$NO_2$, —$NR^4R^5$, —CN, alkyl, cycloalkyl, —OH, alkoxy, alkylthio, hydroxyalkylamino, haloalkyl, haloalkyloxy, hydroxyalkyl, aryl or heteroaryl;
- said $C_2$-$C_{20}$-alkyl residue may be selected from the group comprising —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$C_2H_4$—$CH(CH_3)_2$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$C_7H_{15}$, —$C_3H_6$—$C(CH_3)_3$, —$C_4H_8$—$CH(CH_3)_2$, —$C_3H_6$—$CH(CH_3)$—$C_2H_5$, —$C_2H_4$—$C(CH_3)_2$—$C_2H_5$, —$C_2H_4$—$CH(CH_3)$—$C_3H_7$, —$CH_2$—$C(CH_3)_2$—$C_3H_7$, —$CH_2$—$CH(CH_2)$—$C_4H_9$, —$CH(CH_3)$—$C_5H_{11}$, —$C_8H_{17}$, —$C_4H_8$—$C(CH_3)_3$, —$C_5H_{10}$—$CH(CH_3)_2$, —$C_4H_8$—$CH(CH_3)$—$C_2H_5$, —$C_3H_6$—$C(CH_3)_2$—$C_2H_5$, —$C_3H_6$—$CH(CH_3)$—$C_3H_7$, —$C_2H_4$—$C(CH_3)_2$—$C_3H_7$, —$C_2H_4$—$CH(CH_3)$—$C_4H_9$, —$CH_2$—$C(CH_3)_2$—$C_4H_9$, —$CH_2$—$CH(CH_3)$—$C_5H_{11}$, —$C(CH_3)_2$—$C_5H_{11}$, —$CH(CH_3)$—$C_6H_{13}$, —$C_9H_{19}$, —$C_5H_{10}$—$C(CH_3)_3$, —$C_6H_{12}$—$CH(CH_3)_2$, —$C_5H_{10}$—$CH(CH_3)$—$C_2H_5$, —$C_4H_8$—$C(CH_3)_2$—$C_2H_5$, —$C_4H_8$—$CH(CH_3)$—$C_3H_7$, —$C_3H_6$—$C(CH_3)_2$—$C_3H_7$, —$C_3H_6$—$CH(CH_3)$—$C_4H_9$, —$C_2H_4$—$C(CH_3)_2$—$C_4H_9$, —$C_2H_4$—$CH(CH_3)$—$C_5H_{11}$, —$CH_2C(CH_3)_2$—$C_5H_{11}$, —$CH_2$—$CH(CH_3)$—$C_6H_{13}$, —$C(CH_3)_2$—$C_6H_{13}$, —$CH(CH_3)$—$C_7H_{15}$, —$C_{10}H_{21}$, —$C_6H_{12}$—$C(CH_3)_3$, —$C_7H_{14}$—$CH(CH_3)_2$, —$C_6H_{12}$—$CH(CH_3)$—$C_2H_5$, —$C_5H_{10}$—$C(CH_3)_2$—$C_2H_5$, —$C_5H_{10}$—$CH(CH_3)$—$C_3H_7$, —$C_4H_8$—$C(CH_3)_2$—$C_3H_7$, —$C_4H_8$—$CH(CH_3)$—$C_4H_9$, —$C_3H_6$—$C(CH_3)_2$—$C_4H_9$, —$C_3H_6$—$CH(CH_3)$—$C_5H_{11}$, —$C_2H_4$—$C(CH_3)_2$—$C_5H_{11}$, —$C_2H_4$—$CH(CH_3)$—$C_6H_{13}$, —$CH_2$—$C(CH_3)_2$—$C_6H_{13}$, —$CH_2$—$CH(CH_3)$—$C_7H_{15}$, —$C(CH_3)_2$—$C_7H_{15}$, —$CH(CH_3)$—$C_8H_{17}$, —$C_{11}H_{23}$, —$C_7H_{14}$—$C(CH_3)_3$, —$C_8H_{16}$—$CH(CH_3)_2$, —$C_7H_{14}$—$CH(CH_3)$—$C_2H_5$, —$C_6H_{12}$—$C(CH_3)_2$—$C_2H_5$, —$C_6H_{12}$—$CH(CH_3)$—$C_3H_7$, —$C_5H_{10}$—$C(CH_3)_2$—$C_3H_7$, —$C_5H_{10}$—$CH(CH_3)$—$C_4H_9$, —$C_4H_8$—$C(CH_3)_2$—$C_4H_9$, —$C_4H_8$—$CH(CH_3)$—$C_5H_{11}$, —$C_3H_6$—$C(CH_3)_2$—$C_5H_{11}$, —$C_3H_6$—$CH(CH_3)$—$C_6H_{13}$, —$C_2H_4$—$C(CH_3)_2$—$C_6H_{13}$, —$C_2H_4$—$CH(CH_3)$—$C_7H_{15}$, —$CH_2$—$C(CH_3)_2$—$C_7H_{15}$, —$CH_2$—$CH(CH_3)$—$C_8H_{17}$, —$C(CH_3)_2$—$C_8H_{17}$, —$CH(CH_3)$—$C_9H_{19}$, —$C_{12}H_{25}$, —$C_8H_{16}$—$C(CH_3)_3$, —$C_9H_{18}$—$CH(CH_3)_2$, —$C_8H_{16}$—$CH(CH_3)$—$C_2H_5$, —$C_7H_{14}$—$C(CH_3)_2$—$C_2H_5$, —$C_7H_{14}$—$C(CH_3)$—$C_3H_7$, —$C_6H_{12}$—$C(CH_3)_2$—$C_3H_7$, —$C_6H_{12}$—$CH(CH_3)$—$C_4H_9$, —$C_5H_{10}$—$C(CH_3)_2$—$C_4H_9$, —$C_5H_{10}$—$CH(CH_3)$—$C_5H_{11}$, —$C_4H_8$—$C(CH_3)_2$—$C_5H_{11}$, —$C_4H_8$—$CH(CH_3)$—$C_6H_{13}$, —$C_3H_6$—$C(CH_3)_2$—$C_6H_{13}$, —$C_3H_6$—$CH(CH_3)$—$C_7H_{15}$, —$C_2H_4$—$C(CH_3)_2$—$C_7H_{15}$, —$C_2H_4$—$CH(CH_3)$—$C_8H_{17}$, —$CH_2$—$C(CH_3)_2$—$C_8H_{17}$, —$CH_2$—$CH(CH_3)$—$C_9H_{19}$, —$C(CH_3)_2$—$C_9H_{19}$, —$CH(CH_3)$—$C_{10}H_{21}$;
- an alkyl group, if not stated otherwise, denotes a linear or branched $C_1$-$C_6$-alkyl, preferably a linear or branched chain of one to five carbon atoms, a linear or branched $C_1$-$C_6$-alkenyl or a linear or branched $C_1$-$C_6$-alkinyl group, which can optionally be substituted by one or more substituents $R^3$, preferably by halogen;
- the $C_1$-$C_6$-alkyl, $C_1$-$C_6$-alkenyl and $C_1$-$C_6$-alkinyl residue may be selected from the group comprising —$CH_3$, —$C_2H_5$, —$CH=CH_2$, —$C\equiv CH$, —$C_3H_7$, —$CH(CH_3)_2$, —$CH_2$—$CH=CH_2$, —$C(CH_3)=CH_2$, —$CH=CH$—$CH_3$, —$C\equiv C$—$CH_3$, —$CH_2$—$C\equiv CH$, —$C_4H_9$, —$CH_2$—$CH(CH_3)_2$, —$CH(CH_3)$—$C_2H_5$, —$C(CH_3)_3$, —$C_5H_{11}$, —$C_6H_{13}$, —$C(R^3)_3$, —$CR^3(R^{3'})_2$, —$CR^3(R^{3'})R^{3''}$, —$C_2(R^3)_5$, —$CH_2$—$C(R^3)_3$, —$CH_2$—$CR^3(R^3)_2$, —$CH_2$—$CR^3(R^{3'})R^{3''}$, —$C_3(R^3)_7$, —$C_2H_4$—$C(R^3)_3$, —$C_2H_4$—$CH=CH_2$, —$CH=CH$—$C_2H_5$, —$CH=C(CH_3)_2$, —$CH_2$—$CH=CH$—$CH_2$, —$CH=CH$—$CH=CH_2$, —$C_2H_4$—$C\equiv CH$, —$C\equiv C$—$C_2H_5$, —$CH_2$—$C\equiv C$—$CH_3$, —$C\equiv C$—$CH=CH_2$, —$CH=CH$—$C\equiv CH$, —$C\equiv C$—$C\equiv CH$, —$C_2H_4$—$CH(CH_3)_2$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$C_3H_6$—$CH=CH_2$, —$CH=CH$—$C_3H_7$, —$C_2H_4$—$CH=CH$—$CH_3$, —$CH_2CH=CH$—$C_2H_5$, —$CH_2$—$CH=CH$—$CH=CH_2$, —$CH=CH$—$CH=CH$—$CH_3$, —$CH=CH$—$CH_2$—$CH=CH_2$, —$C(CH_3)=CH$—$CH=CH_2$, —$CH=C(CH_3)$—$CH=CH_2$, —$CH=CH$—$C(CH_3)=CH_2$, —$CH_2$—$CH=C(CH_3)_2$, —$C(CH_3)=C(CH_3)_2)$, —$C_3H_6$—$C\equiv CH$, —$C\equiv C$—$C_3H_7$, —$C_2H_4$—$C\equiv C$—$CH_3$, —$CH_2$—$C\equiv C$—$C_2H_5$, —$CH_2$—$C\equiv C$—$CH=CH_2$, —$CH_2$—$CH=CH$—$C\equiv CH$, —$CH_2$—$C\equiv C$—$C\equiv CH$, —$C\equiv C$—$CH=CH$—$CH_3$, —$CH=CH$—$C\equiv C$—$CH_3$, —$C\equiv C$—$C\equiv C$—$CH_3$, —$C\equiv C$—$CH_2$—$CH=CH_2$, —$CH=CH$—$CH_2$—$C\equiv CH$, —$C\equiv C$—$CH_2$—$C\equiv CH$, —$C(CH_3)=CH$—$CH=CH_2$, —$CH=C(CH_3)$—$CH=CH_2$, —$CH=CH$—$C(CH_3)=CH_2$, —$C(CH_3)=CH$—$C\equiv CH$, —$CH=C(CH_3)$—$C\equiv CH$, —$C\equiv C$—$C(CH_3)=CH_2$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH)CH_3)$—$C_2H_5$, —$CH_2$—$CH(CH_3)$—$CH(CH_3)_2$, —$CH_2C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$C_4H_8$—$CH=CH_2$, —$CH=CH$—$C_4H_9$, —$C_3H_6$—$CH=CH$—$CH_3$, —$CH_2$—$CH=CH$—$C_3H_7$, —$C_2H_4$—$CH=CH$—$C_2H_5$, —$CH_2$—$C(CH_3)=C(CH_3)_2$, —$C_2H_4$—$CH=C(CH_3)_2$, —$C_4H_8$—$C\equiv CH$, —$C\equiv C$—$C_4H_9$, —$C_3H_6$—$C\equiv C$—$CH_3$, —$CH_2$—$C\equiv C$—$C_3H_7$, —$C_2H_4$—$C\equiv C$—$C_2H_5$;
- a cycloalkyl group denotes a non-aromatic ring system containing three to eight carbon atoms, preferably four to eight carbon atoms, wherein one or more of the carbon atoms in the ring can be substituted by a group X, X being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$;

an alkoxy group denotes an O-alkyl group, the alkyl group being as defined above, the alkoxy group is preferably a methoxy, ethoxy, isopropoxy, t-butoxy or pentoxy group.

an haloalkyl group denotes an alkyl group which is substituted by one to five halogen atoms, the alkyl group being as defined above; the haloalkyl group is preferably a —$C(R^{10})_3$, —$CR^{10}(R^{10'})_2$, —$CR^{10}(R^{10'})R^{10''}$, —$C_2(R^{10})_5$, —$CH_2$—$C(R^{10})_3$, —$CH_2$—$CR^{10}(R^{10'})_2$, —$CH_2$—$CR^{10}(R^{10'})R^{10''}$, —$C_3(R^{10})_7$ or —$C_2H_4$—$C(R^{10})_3$, wherein $R^{10}$, $R^{10'}$, $R^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —$OC(R^{10})_3$, —$OCR^{10}(R^{10'})_2$, —$OCR^{10}(R^{10'})R^{10''}$, —$OC_2(R^{10})_5$, —$OCH_2$—$C(R^{10})_3$, —$OCH_2$—$CR^{10}(R^{10'})_2$, —$OCH_2$—$CR^{10}(R^{10'})R^{10''}$, —$OC_3(R^{10})_7$ or —$OC_2H_4$—$C(R^{10})_3$, wherein $R^{10}$, $R^{10'}$, $R^{10''}$ represent F, Cl, Br or I, preferably F;

a hydroxyalkylamino group denotes an (HO-alkyl)$_2$-N- group or HO-alkyl-NH- group, the alkyl group being as defined above;

a halogen group is chlorine, bromine, fluorine or iodine;

an aryl group preferably denotes an aromatic group having five to fifteen carbon atoms, which can optionally be substituted by one or more substituents $R^3$, where $R^3$ is as defined above; the aryl group is preferably a phenyl group, —$CH_2$—$C_6H_4$, —$C_2H_4$—$C_6H_4$, —CH=CH—$C_6H_4$, —C≡C—$C_6H_4$, -o-$C_6H_4$—$R^3$, -m-$C_6H_4$—$R^3$, -p-$C_6H_4$—$R^3$, -o-$CH_2$—$C_6H_4$—$R^3$, -m-$CH_2$—$C_6H_4$—$R^3$, -p-$CH_2$—$C_6H_4$—$R^3$;

a heteroaryl group denotes a 5- or 6-membered heterocyclic group which contains at least one heteroatom like O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl group. This heterocyclic group can optionally be substituted by one or more substituents $R^3$, where $R^3$ is as defined above.

with the proviso that N-(1-methyl-1H-pyrazole-5-yl)-1H-pyrazole-1-carboxamide, and 1-ethyl-3-methyl-N-(1-methyl-1H-pyrazole-5-yl)-4-nitro-1H-pyrazole-5-carboxamide are excluded.

Furthermore the present invention is directed to novel compounds of the general Formula (XI) and pharmaceutically acceptable salts thereof;

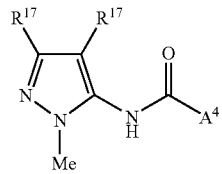

wherein $A^4$ is an optionally substituted $C_2$-$C_{20}$-alkyl or a 5-membered heteroaryl group, which contains at least one heteroatom like O, N, S, $NR^4$, SO, $SO_2$, Se; which can optionally be substituted by one or more substituents $R^3$;

$R^3$ is independently H, $OR^4$, $SR^4$, hydroxyalkyl, hydroxyalkylamino, cycloalkyl, halogen, haloalkyl, haloalkyloxy, $NO_2$, CN, $SO_2NR^4R^5$, $CO_2NR^4R^5$, $COR^4$, $CO_2R^4$, $SO_2R^4$, $SO_3R^4$, $NR^4R^5$, alkyl, aryl or heteroaryl;

$R^4$ is H, alkyl, cycloalkyl, aryl or heteroaryl;

$R^5$ is H, O-alkyl, O-aryl, alkyl, heteroaryl or aryl;

$R^{17}$ is independently of each other —H, —F, —Cl, —I, —$NO_2$, —$NR^4R^5$, —CN, alkyl, cycloalkyl, —OH, alkoxy, alkylthio, hydroxyalkylamino, haloalkyl, haloalkyloxy, hydroxyalkyl, aryl or heteroaryl;

said $C_2$-$C_{20}$-alkyl residue may be selected from the group given above for $C_2$-$C_{20}$-alkyl residue of Formula (XI).

a cycloalkyl group is defined as above in Formula (X);

an alkoxy group is defined as above in Formula (X);

an haloalkyl is defined as above for in Formula (X);

a hydroxyalkyl group is defined as above in Formula (X);

an haloalkyloxy group is defined as above in Formula (X);

a hydroxyalkylamino group is defined as above in Formula (X);

a halogen group is defined as above in Formula (X);

an aryl group is defined as above in Formula (X);

a heteroaryl group may be selected from the group comprising oxazole-2-yl, oxazol-4-yl, oxazole-5-yl, thiazole-2-yl, thiazole-4yl, thiazole-5-yl, isothiazole-3-yl, isothiazole-4-yl, isothiazole-5-yl, 1,2,4-oxadiazole-3-yl, 1,2,4oxadiazole-5-yl, 1,2,4-thiadiazole-3-yl, 1,2,4-thiadiazole-5-yl, 1,2,5-oxadiazole-3-yl, 1,2,5-oxadiazole-4-yl, 1,2,5-thiadiazole-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 4-pyridyl, 4-pyrimidinyl, 5-pyrimidinyl, 3-pyridazinyl, 4-pyridazinyl, 2-pyrazinyl, 3-pyrazolyl, 4-pyrazolyl, indolyl, indolinyl, benzo[b]thiophenyl, benzimidazolyl, quinazolinyl, quinoxazolinyl, preferably isoxazole-3-yl, isoxazole-4-yl, isoxazole-5-yl, tetrahydroquinolinyl, isoquinolinyl, tetrahydroisoquinolinyl group, wherein said heteroaryl group can optionally be substituted by one or more substituents $R^3$, $R^3$ being as defined above in Formula (XI).

Furthermore the present invention is directed to novel compounds of the general Formula (XII) and pharmaceutically acceptable salts thereof:

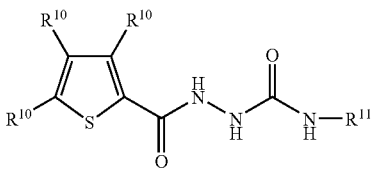

wherein
- R¹¹ is an optionally substituted phenyl group by one to five substituents R⁹ or an optionally substituted $C_4$-$C_{20}$-alkyl group by one or more substituents R³;
- R⁹ is independently of each other —H, —F, —Cl, —Br, —I, —SO₂NH⁴, —SO₂N(R⁴)₂, —NR⁴R⁵, —NR⁴—CO—($C_1$-$C_6$)-haloalkyl, —NO₂, —NR⁴—SO₂—($C_1$-$C_6$)-haloalkyl, —CN, alkyl, cycloalkyl, —OH, —SH, alkylthio, alkoxy, hydroxyalkylamino, haloalkyloxy, haloalkyl, hydroxyalkyl, -aryl or heteroaryl;
- R¹⁰ is independently of each other —H, —F, —Cl, —Br, —I, —NO₂, NR⁴R⁵, —CN, alkyl, —OH, cycloalkyl, —SH, alkylthio, hydroxyalkylamino, hydroxyalkyl, aryl or heteroaryl;
- R³, R³', R³'' is independently H, OR⁴, SR⁴, hydroxyalkyl, hydroxyalkylamino, cycloalkyl, halogen, haloalkyl, haloalkyloxy, NO₂, CN, SO₂NR⁴R⁵, CO₂NR⁴R⁵, COR⁴, CO₂R⁴, SO₂R⁴, SO₃R⁴, NR⁴R⁵, alkyl, aryl or heteroaryl,
- R⁴ is H, alkyl, cycloalkyl, aryl or heteroaryl;
- R⁵ is H, O-alkyl, O-aryl, alkyl, heteroaryl or aryl;
- X is selected from the group consisting of S, O, N, NR⁴, SO or SO₂;
- said $C_4$-$C_{20}$-alkyl residue may be selected from the group comprising —C₄H₉, —CH₂—CH(CH₃)₂, —CH(CH₃)—C₂H₅, —C(CH₃)₃, —C₅H₁₁, —C₂H₄—CH(CH₃)₂, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —C₇H₁₅, —C₃H₆—C(CH₃)₃, —C₄H₈—CH(CH₃)₂, —C₃H₆—CH(CH₃)—C₂H₅, —C₂H₄—C(CH₃)₂—C₂H₅, —C₂H₄—CH(CH₃)—C₃H₇, —CH₂—C(CH₃)₂—C₃H₇, —CH₂—CH(CH₃)—C₄H₉, —CH(CH₃)—C₅H₁₁, —C₈H₁₇, —C₄H₈—C(CH₃)₃, —C₅H₁₀—CH(CH₃)₂, —C₄H₈—CH(CH₃)—C₂H₅, —C₃H₆—C(CH₃)₂—C₂H₅, —C₃H₆—CH(CH₃)—C₃H₇, —C₂H₄—C(CH₃)₂—C₃H₇, —C₂H₄—CH(CH₃)—C₄H₉, —CH₂—C(CH₃)₂—C₄H₉, —CH₂—CH(CH₃)—C₅C₁₁, —C(CH₃)₂—C₅H₁₁, —CH(CH₃)—C₆H₁₃, —C₉H₁₉, —C₅H₁₀—C(CH₃)₃, —C₆H₁₂—CH(CH₃)₂, —C₅H₁₀—CH(CH₃)—C₂H₅, —C₄H₈—C(CH₃)₂—C₂H₅, —C₄H₈—CH(CH₃)—C₃H₇, —C₃H₆—C(CH₃)₂—C₃H₇, —C₃H₆—CH(CH₃)—C₄H₉, —C₂H₄—C(CH₃)₂—C₄H₉, —C₂H₄—CH(CH₃)—C₅H₁₁, —CH₂—C(CH₃)₂—C₅H₁₁, —CH₂—CH(CH₃)—C₆H₁₃, —C(CH₃)₂—C₆H₁₃, —CH(CH₃)—C₇H₁₅, —C₁₀H₂₁, —C₆H₁₂—C(CH₃)₃, —C₇H₁₄—CH(CH₃)₂, —C₆H₁₂—CH(CH₃)—C₂H₅, —C₅H₁₀—C(CH₃)₂—C₂H₅, —C₅H₁₀—CH(CH₃)—C₃H₇, —C₄H₈—C(CH₃)₂—C₃H₇, —C₄H₈—CH(CH₃)—C₄H₉, —C₃H₆—C(CH₃)₂—C₄H₉, —C₃H₆—CH(CH₃)—C₅H₁₁, —C₂H₄—C(CH₃)₂—C₅H₁₁, —C₂H₄—CH(CH₃)—C₆H₁₃, —CH₂—C(CH₃)₂—C₆H₁₃, —CH₂—CH(CH₃)—C₇H₁₅, —C(CH₃)₂—C₇H₁₅, —CH(CH₃)—C₈H₁₇, —C₁₁H₂₃, —C₇H₁₄—C(CH₃)₃, —C₈H₁₆—CH(CH₃)₂, —C₇H₁₄—CH(CH₃)—C₂H₅, —C₆H₁₂—C(CH₃)₂—C₂H₅, —C₆H₁₂—CH(CH₃)—C₃H₇, —C₅H₁₀—C(CH₃)₂—C₃H₇, —C₅H₁₀—CH(CH₃)—C₄H₉, —C₄H₈—C(CH₃)₂—C₄H₉, —C₄H₈—CH(CH₃)—C₅H₁₁, —C₃H₆—C(CH₃)₂—C₅H₁₁, —C₃H₆—CH(CH₃)—C₆H₁₃, —C₂H₄—C(CH₃)₂—C₆H₁₃, —C₂H₄—CH(CH₃)—C₇H₁₅, —CH₂—C(CH₃)₂—C₇H₁₅, —CH₂—CH(CH₃)—C₈H₁₇, —C(CH₃)₂—C₈H₁₇, —CH(CH₃)—C₉H₁₉, —C₁₂H₂₅, —C₈H₁₆—C(CH₃)₃, —C₉H₁₈—CH(CH₃)₂, —C₈H₁₆—CH(CH₃)—C₂H₅, —C₇H₁₄—C(CH₃)₂—C₂H₅, —C₇H₁₄—CH(CH₃)—C₃H₇, —C₆H₁₂—C(CH₃)₂—C₃H₇, —C₆H₁₂—CH(CH₃)—C₄H₉, —C₅H₁₀—C(CH₃)₂—C₄H₉, —C₅H₁₀—CH(CH₃)—C₅H₁₁, —C₄H₈—C(CH₃)₂—C₅H₁₁, —C₄₈—CH(CH₃)—C₆H₁₃, —C₃H₆—C(CH₃)₂—C₆H₁₃, —C₃H₆—CH(CH₃)—C₇H₁₅, C₂H₄—C(CH₃)₂—C₇H₁₅, —C₂H₄—CH(CH₃)—C₈H₁₇, CH₂—C(CH₃)₂—C₈H₁₇, —CH₂—CH(CH₃)—C₉H₁₉, —C(CH₃)₂—C₉H₁₉, —CH(CH₃)—C₁₀H₂₁;
- an alkyl group, if not stated otherwise, denotes a linear or branched $C_1$-$C_6$-alkyl, preferably a linear or branched chain of one to five carbon atoms, a linear or branched $C_1$-$C_6$-alkenyl or a linear or branched $C_2$-$C_6$-alkinyl group, which can optionally be substituted by one or more substituents R³, preferably by halogen;
- the $C_1$-$C_6$-alkyl, $C_1$-$C_6$-alkenyl and $C_1$-$C_6$-alkinyl residue may be selected from the group comprising —CH₃, —C₂H₅, —CH=CH₂, —C≡CH, —C₃H₇, —CH(CH₃)₂, —CH₂—CH=CH₂, —C(CH₃)=CH₂, —CH=CH—CH₃, —C≡C—CH₃, —CH₂—C≡CH, —C₄H₉, —CH₂—CH(CH₃)₂, —CH(CH₃)—C₂H₅, —C(CH₃)₃, —C₅H₁₁, —C₆H₁₃, —C(R³)₃, —CR³(R³')₂, —CR³(R³')R³'', —C₂(R³)₅, —CH(CH₃)—C₂H₅, —C(CH₃)₃, —C₅H₁₁, —C₆H₁₃, —C(R³)₂—CH₂—C(R³)₃, —CH₂—CR³(R³')₂, —CH₂—CR³(R³')R³'', —C₃(R³)₇, —C₂H₄—C(R³)₃, —C₂H₄—CH=CH₂, —CH=CH—C₂H₅, —CH=C(CH₃)₂, —CH₂—CH=CH—CH₃, —CH=CH—CH=CH₂, —C₂H₄—C≡CH, —C≡C—C₂H₅, —CH₂—C≡C—CH₃, —C≡C—CH=CH₂, —CH=CH—C≡CH, —C≡C—C≡CH, —C₂H₄—CH(CH₃)₂, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —C₃H₆—CH=CH₂, —CH=CH—C₃H₇, —C₂H₄—CH=CH—CH₃, —CH₂—CH=CH—C₂H₅, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —CH₂—CH=C(CH₃)₂, —C(CH₃)=C(CH₃)₂, —C₃H₆—C≡CH, —C≡C—C₃H₇, —C₂H₄—C≡C—CH₃, —CH₂—C≡C—C₂H₅, —CH₂—C≡C—CH=CH₂, —CH₂—CH=CH—C≡CH, —CH₂C≡C—C≡CH, —C≡C—CH=CH—CH₃, —CH=CH—C≡C—CH₃, —C≡C—C≡C—CH₃, —C≡C—CH₂—CH=CH₂, —CH=CH—CH₂—C≡CH, —C≡C—CH₂—C≡CH, —C(CH₃)=CH—CH=CH₂, —CH=C(CH₃)—CH=CH₂, —CH=CH—C(CH₃)=CH₂, —C(CH₃)=CH—C≡CH, —CH=C(CH₃)—

C≡CH, —C≡C—C(CH₃)=CH₂, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —C₄H₈—CH=CH₂, —CH=CH—C₄H₉, —C₃H₆—CH=CH—CH₃, —CH₂—CH=CH—C₃H₇, —C₂H₄—CH=CH—C₂H₅, —CH₂—C(CH₃)=C(CH₃)₂, —C₂H₄—CH=C(CH₃)₂, —C₄H₈—C≡CH, —C≡C—C₄H₉, —C₃H₆—C≡C—CH₃, —CH₂—C≡C—C₃H₇, —C₂H₄—C≡C—C₂H₅; $R^3$, $R^{3'}$ or $R^{3''}$ being as defined above;

a cycloalkyl group denotes a non-aromatic ring system containing three to eight carbon atoms, preferably four to eight carbon atoms, wherein one or more of the carbon atoms in the ring can be substituted by a group X, X being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$;

an alkoxy group denotes an O-alkyl group, the alkyl group being as defined above; the alkoxy group is preferably a methoxy, ethoxy, isopropoxy, t-butoxy or pentoxy group, an haloalkyl group denotes an alkyl group which is substituted by one to five halogen atoms, the alkyl group being as defined above; the haloalkyl group is preferably a —C($R^{10}$)₃, —C$R^{10}$($R^{10'}$)₂, —C$R^{10}$($R^{10'}$)$R^{10''}$, —C₂($R^{10}$)₅, —CH₂C($R^{10}$)₃, —CH₂—C$R^{10}$($R^{10'}$)₂, —CH₂—C$R^{10}$($R^{10'}$)$R^{10''}$, —C₃($R^{10}$)₇ or —C₂H₄—C($R^{10}$)₃, wherein $R^{10}$, $R^{10'}$, $R^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC($R^{10}$)₃, —OC$R^{10}$($R^{10'}$)₂, —OC$R^{10}$($R^{10'}$)$R^{10''}$, —OC₂($R^{10}$)₅, —OCH₂—C($R^{10}$)₃, —OCH₂—C$R^{10}$($R^{10'}$)₂, —OCH₂C$R^{10}$($R^{10'}$)$R^{10''}$, —OC₃($R_{10}$)₇ or —OC₂H₄—($R^{10}$)₃, wherein $R^{10}$, $R^{10'}$, $R^{10''}$ represent F, Cl, Br or I, preferably F;

a hydroxyalkylamino group denotes an (HO-alkyl)₂-N- group or HO-alkyl-NH- group, the alkyl group being as defined above;

a halogen group is chlorine, bromine, fluorine or iodine;

an aryl group preferably denotes an aromatic group having five to fifteen carbon atoms, which can optionally be substituted by one or more substituents $R^3$, where $R^3$ is as defined above; the aryl group is preferably a phenyl group, —CH₂—C₆H₄, —C₂H₄—C₆H₄, —CH=CH—C₆H₄, —C≡C—C₆H₄, -o-C₆H₄—$R^3$, -m-C₆H₄—$R^3$, -p-C₆H₄—$R^3$, -o-CH₂—C₆H₄—$R^3$, -m-CH₂—C₆H₄—$R^3$, -p-CH₂—C₆H₄—$R^3$;

a heteroaryl group denotes a 5- or 6-membered heterocyclic group which contains at least one heteroatom like O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl group. This heterocyclic group can optionally be substituted by one or more substituents $R^3$, where $R^3$ is as defined above.

However, the following compounds are excluded from Formula (XI): 2-thiophenecarboxylic acid-5-bromo-2-[[(4chlorophenyl)amino]carbonyl]hydrazide, 2-thiophenencarboxylic acid-2-[[(4-ethoxyphenyl)amino]carbonyl]hydrazide, 2-thiophenecarboxylic acid-3-methyl-2-[[(3,4dichlorophenyl)amino]carbonyl]hydrazide, 2-thiophenecarboxylic acid-2-[[(4-methylphenyl)amino]carbonyl]hydrazide, 2-thiophene-carboxylic acid-2-[[(4-chlorophenyl)amino]carbonyl]hydrazide, 2-thiophenecarboxylic acid-2-[[(3chlorophenyl)amino]carbonyl]hydrazide and 2-thiophenecarboxylic acid-2-[(phenylamino)carbonyl]hydrazide.

Furthermore the present invention is directed to novel compounds of the general Formula (XII) and pharmaceutically acceptable salts thereof:

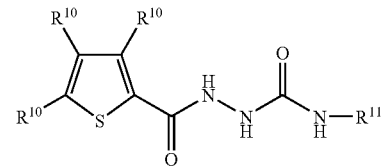

wherein $R^{11}$ is an optionally substituted phenyl group by one to five substituents $R^9$ or an optionally substituted $C_4$-$C_{20}$-alkyl group by one or more substituents $R^3$;

$R^9$ is independently of each other —F, —I, —SO₂NH$R^4$, —SO₂N($R^4$)₂, —N$R^4R^5$, —N$R^4$—CO—($C_1$-$C_6$)-haloalkyl, —NO₂, —N$R_4$—SO₂—($C_1$-$C_6$)-haloalkyl, —CN, $C_2$-$C_5$-alkyl, cycloalkyl, —OH, —SH, alkylthio, methoxy, propoxy, hydroxyalkylamino, haloalkyloxy, haloalkyl, hydroxyalkyl, aryl or heteroaryl;

$R^{10}$ is independently of each other —H, —F, —Cl, —I, —NO₂, N$R^4R^5$, —CN, $C_2$-$C_5$-alk cycloalkyl, —OH, —SH, alkylthio, hydroxyalkylamino, hydroxyalkyl, aryl or heteroaryl;

wherein said $C_2$-$C_5$-alkyl group of $R^9$ and $R^{10}$ denotes a linear or branched $C_2$-$C_5$-alkyl, a linear or branched $C_2$-$C_5$-alkenyl or a linear or branched $C_2$-$C_5$-alkinyl group, which can optionally be substituted by one or more substituents $R^3$, preferably by halogen; the $C_2$-$C_5$-alkyl, $C_2$-$C_5$-alkenyl and $C_2$-$C_5$-alkinyl residue may be selected from the group comprising —C₂H₅, —CH=CH₂, —C≡CH, —C₃H₇, —CH(CH₃)₂, —C≡C—CH₃, —CH₂—C≡CH, —CH₂—CH=CH₂, —C(CH₃)=CH₂, —CH=CH—CH₃, —C₄H₉, —C₂—CH(CH₃)₂, —CH(CH₃)—C₂H₅, —C(CH₃)₃, —C₅H₁₁, —C($R^3$)₃, —C$R^3$($R^3$)₂, —C$R^3$($R^{3'}$)$R^{3''}$, —C₂($R^3$)₅, —CH₂—C($R^3$)₃, —CH₂—C$R^3$($R^{3'}$)₂, —CH₂—C$R^3$($R^{3'}$)$R^{3''}$, —C₃($R^3$)₇, —C₂H₄—C($R^3$)₃, —C₂H₄—CH=CH₂, —CH=CH—C₂H₅, —CH=C(CH₃)₂, —CH₂—CH=CH—CH₃, —CH=CH—CH=CH$_2$, —C$_2$H$_4$—C≡CH, —C≡C—C$_2$H$_5$, —CH$_2$—C≡C—CH$_3$, —C≡C—CH=CH$_2$, —CH=CH—C≡CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —CH$_2$—CH=C(CH$_3$)$_2$, —C(CH$_3$)=C(CH$_3$)$_2$, —C$_3$H$_6$—C≡CH, —C≡C—C$_3$H$_7$, —C$_2$H$_4$—C≡C—CH$_3$, —CH$_2$—C≡C—C$_2$H$_5$, —CH$_2$—C≡CH—C=CH$_2$, —CH$_2$—CH=CH—C≡CH, —CH$_2$—C≡C—C≡CH, —C≡C—CH=CH—CH$_3$, —CH=CH—C≡C—CH$_3$, —C≡C—C≡C—CH$_3$, —C≡C—CH$_2$—C≡CH, —CH=CH—CH$_2$—C≡CH, —C≡C—CH$_2$—C≡CH, —C(CH$_3$)=CH—CH=CH$_2$, —CH=C(CH$_3$)—CH=CH$_2$, —CH=CH—C(CH$_3$)=CH$_2$, —C(CH$_3$)=CH—C≡CH, —CH=C(CH$_3$)—C≡C—C(CH$_3$)=CH$_2$;

R$^3$, R$^{3'}$ or R$^{3''}$ are defined as above for Formula (XII);
R$^4$ is defined as above for Formula (XII);
R$^5$ is defined as above for Formula (XII);
said C$_2$-C$_{20}$-alkyl residue is defined as above for Formula (XII);
an alkyl group, referring to R$^3$, R$^{3'}$, R$^{3''}$, R$^4$ R$^5$R$^9$ or R$^{10}$ denotes a linear or branched C$_1$-C$_6$-alkyl, preferably a linear or branched chain of one to five carbon atoms, a linear or branched C$_1$-C$_6$-alkenyl or a linear or branched C$_1$-C$_6$-alkinyl group, which can optionally be substituted by one or more substituents R$^3$, preferably by halogen;
the C$_1$-C$_6$-alkyl, C$_1$-C$_6$-alkenyl and C$_1$-C$_6$alkinyl residue may be selected from the group comprising —CH$_3$, —C$_2$H$_5$, —CH=CH$_2$, —C≡CH, —C$_3$H$_7$, —CH(CH$_3$)$_2$, —CH$_2$—CH=CH$_2$, —C(CH$_3$)=CH$_2$, —CH=CH—CH$_3$, —C≡CH$_3$, —CH$_2$—C≡CH, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C(R$^3$)$_3$, —CR$^3$(R$^{3'}$)$_2$, —CR$^3$(R$^{3'}$)R$^{3''}$, —C$_2$(R$^3$)$_5$, —CH$_2$—(R$^3$)$_3$, —CH$_2$—CR$^3$(R$^{3'}$)$_2$, —CH$_2$—CR$^3$(R$^{3'}$)R$^{3''}$, —C$_3$(R$^3$)$_7$, —C$_2$H$_4$—C(R$^3$)$_3$, —C$_2$H$_4$—CH=CH$_2$, —CH=CH—C$_2$H$_5$, —CH=C(CH$_3$)$_2$, —CH$_2$—CH=CH—CH$_3$, —CH=CH—CH=CH$_2$, —C$_2$H$_4$—C≡CH, —C≡C—C$_2$H$_5$, —CH$_2$—C≡C—CH$_3$, —C≡C—CH=CH$_2$, —CH=CH—C≡CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —CH$_2$—CH=C(CH$_3$)$_2$, —C(CH$_3$)=C(CH$_3$)$_2$, —C$_3$H$_6$—C≡CH, —C≡C—C$_3$H$_7$, —C$_2$H$_4$—C≡C—CH$_3$, —CH$_2$—C≡C—C$_2$H$_5$, —CH$_2$—C≡C—CH=CH$_2$, —CH$_2$—CH=CH—C≡CH, —CH$_2$—C≡C—C≡CH, —C≡C—CH=CH—CH$_3$, —CH=CH—C≡C—CH$_3$, —C≡C—C≡C—CH$_3$, —C≡C—CH$_2$—C≡CH, —CH=CH—CH$_2$—C≡CH, —C≡C—CH$_2$—C≡CH, —C(CH$_3$)=CH—CH=CH$_2$, —CH=C(CH$_3$)—CH=CH$_2$, —CH=CH—C(CH$_3$)=CH$_2$, —C(CH$_3$)=CH—C≡CH, —CH=C(CH$_3$)—C≡CH, —C≡C—C(CH$_3$)=CH$_2$, —C$_3$H$_6$—CH(CH$_3$)$_2$, —C$_2$H$_4$—CH(CH$_3$)—C$_2$H$_5$, —CH$_2$—CH(CH$_3$)—C$_4$H$_9$, —CH$_2$—CH(CH$_3$)—C$_3$H$_7$, —CH(CH$_3$)—C$_2$H$_4$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—CH(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH=CH$_2$, —CH=CH—C$_4$H$_9$, —C$_3$H$_6$—CH=CH—C(CH$_3$)=CH$_3$, —CH$_2$—CH=CH—C$_3$H$_7$, —C$_2$H$_4$—CH=CH—C$_2$H$_5$, —CH$_2$—C(CH$_3$)$_2$, —C$_2$H$_4$—CH=C(CH$_3$)$_2$, —C$_4$H$_8$—C≡CH, —C≡C—C$_4$H$_9$, —C$_3$H$_6$—C≡C—CH$_3$, —CH$_2$—C≡C—C$_3$H$_7$, —C$_2$H$_4$—C≡C—C$_2$H$_5$; R$^3$, R$^{3'}$ or R$^{3''}$ being as defined above;

an cycloalkyl group is defined as above in Formula (XII);
an alkoxy group is defined as above in Formula (XII);
an haloalkyl group is defined as above in Formula (XII);
a hydroxyalkyl group is defined as above in Formula (XII);
an haloalkyloxy group is defined as above in Formula (XII);
a hydroxyalkylamino group is defined as above in Formula (XII);
a halogen group is chlorine, bromine, fluorine or iodine;
an aryl group is defined as above in Formula (XII);
a heteroaryl group is defined as above in Formula (XII);
Furthermore the present invention is directed to novel compounds of the general Formula (XIII) and pharmaceutically acceptable salts thereof:

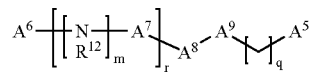

wherein
A$^7$ is independently C=O, C=S, SO$_2$, CH—OR$^{13}$, C=NR$^{12}$, or CH$_2$—CHOR$^{13}$;
A$^8$ is independently C(R$^{14}$)$_2$, O, S, or NR$^{12}$;
A$^9$ is independently C=O, C=S, SO$_2$, CH—OR$^{13}$, C=NR$^{12}$, or CH$_2$—CHOR$^{13}$;
m is 0, or 1;
q is 0, or 1;
r is 0, or 1;
R$^{12}$ is independently H, CH$_3$, CH$_2$—CH$_3$, OCH$_3$, OCH$_2$—CH$_3$, OH, or SH;
R$^{13}$ is independently H, CH$_3$, or CH$_2$—CH$_3$;
R$^{14}$ is independently H, alkyl, alkoxy, OH, or SH;
A$^5$ is a optionally substituted C$_3$-C$_{16}$-alkyl group by one or more substituents R$^3$or an optionally substituted heteroaryl group, which contains at least one heteroatom like O, N, S, NR$^4$, SO, SO$_2$, Se, and which can optionally be substituted by one or more substituents R$^8$, R$^{8'}$, or R$^9$;
A$^6$ is an optionally substituted heteroaryl group, which contains at least one heteroatom like O, N, S, NR$^4$, SO, SO$_2$, Se, and which can optionally be substituted by one or more substituents R$^8$, R$^{8'}$, or R$^9$,
or a heterocyclic group, which contains at least one double bond, and which may contain a heteroatom like O, N, S, NR$^4$, SO, SO$_2$, Se, and which can optionally be substituted by one or more substituents R$^8$, R$^{8'}$, or R$^9$, or one of the groups below:
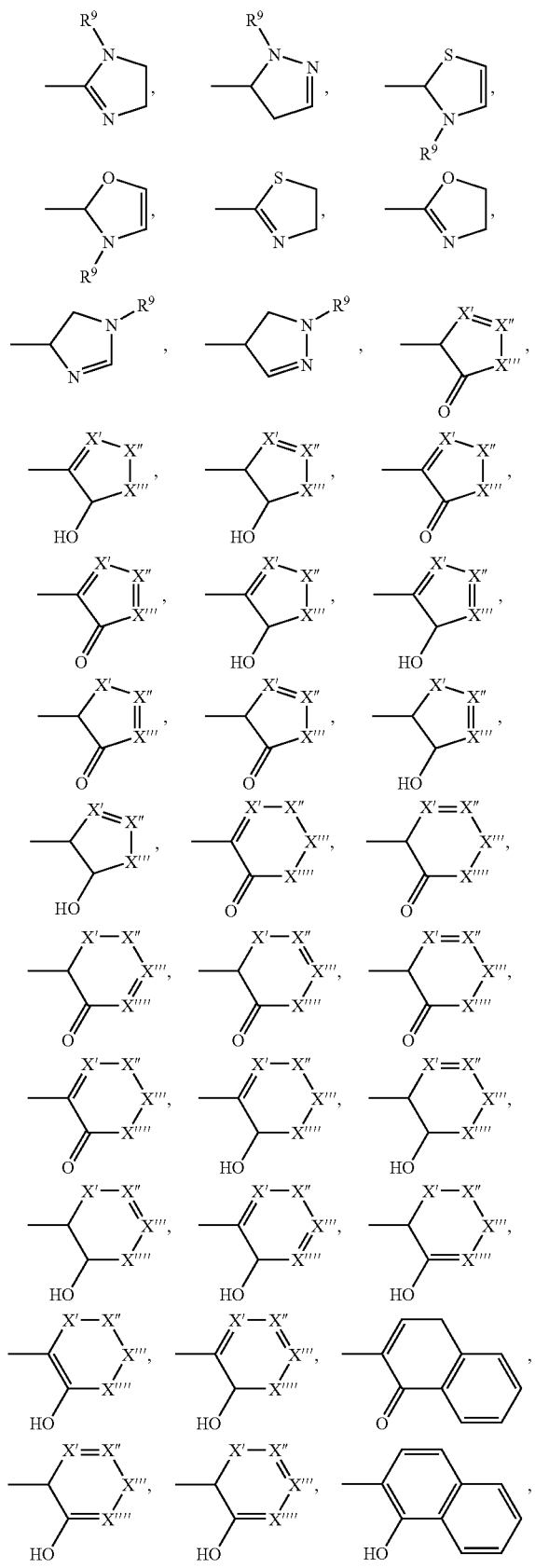
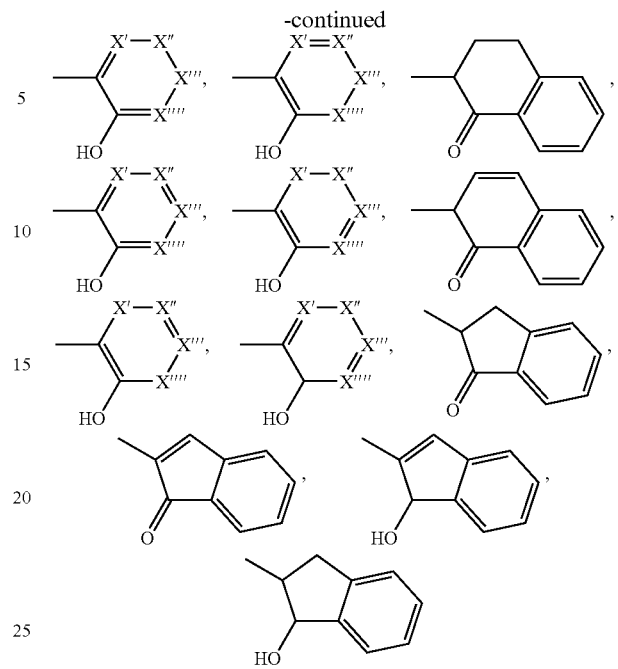
or one of the groups mentioned below: wherein m=0,
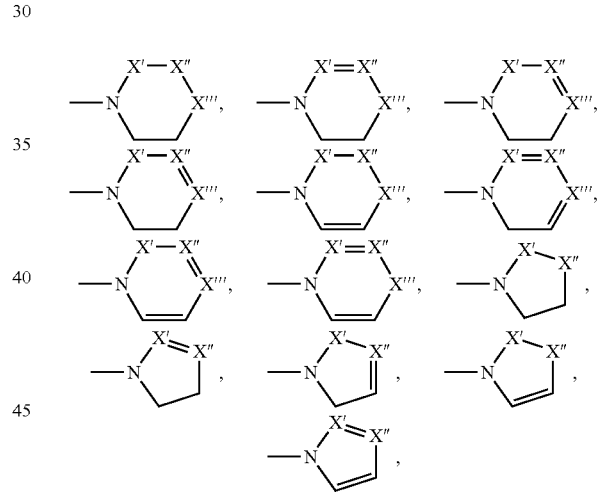
or one of the groups mentioned below: wherein m and r=0,
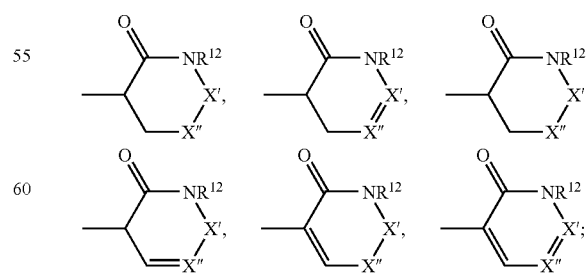
wherein X', X", X''', X"" is independently H, S, O, N, NR$^4$, SO, SO$_2$, CH, or CH$_2$;

$R^8$, $R^{8'}$, $R^9$ is independently H, methyl, ethyl, t-butyl, CN, halogen, OH, alkoxy, $NR^4R^5$, $COOR^4$;

$R^3$ is independently H, $OR^4$, $SR^4$, hydroxyalkyl, hydroxyalkylamino, cycloalkyl, halogen, haloalkyl, haloalkyloxy, $NO_2$, CN, $SO_2NR^4R^5$, $CO^2NR^4R^5$, $COR^4$, $CO_2R^4$, $SO_2R^4$, $SO_3R^4$, $NR^4R^5$, alkyl, aryl or heteroaryl;

$R^4$ is H, alkyl, cycloalkyl, aryl or heteroaryl;

$R^5$ is H, O-alkyl, O-aryl, alkyl, heteroaryl or aryl, said heteroaryl group of $A^5$ or $A^6$ may be selected from the group comprising:

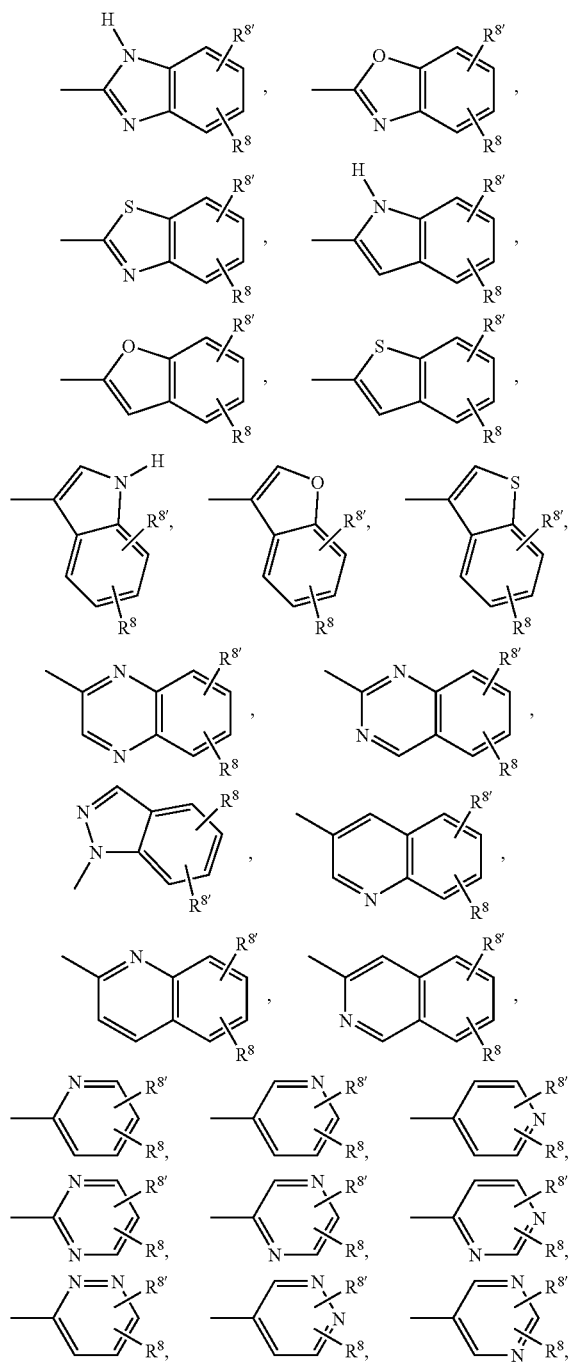

-continued

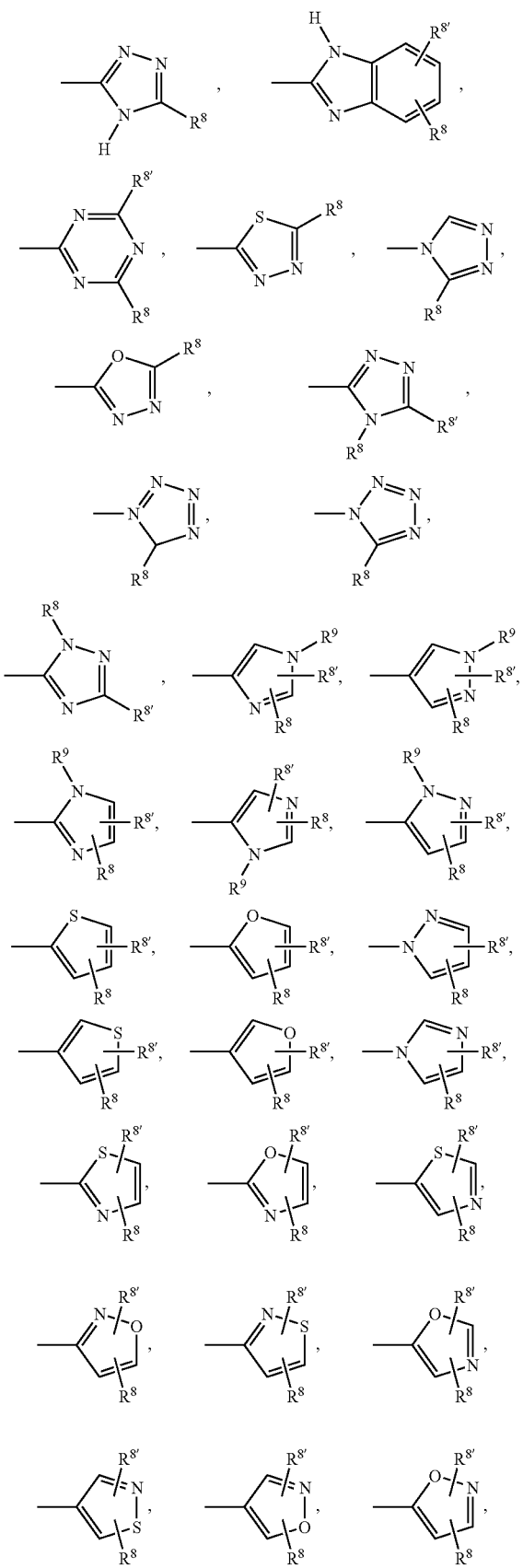

-continued

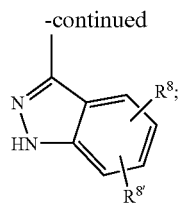

said C₃-C₁₆ alkyl residue may be selected from the group comprising —C₃H₇, —CH(CH₃)₂, —C₄H₉, —CH₂—CH(CH₃)₂, —CH(CH₃)—C₂H₅, —CH₂—CH(CH₃)—CH₃, —C(CH₃)₃, —C₅H₁₁, —C₂H₄—CH(CH₃)₂, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—₂H₅, —C(CH₃)₂—C₃H₇, —C(CH₃)₂—CH(CH₃)₂, —C₂H₄—C(CH₃)₃, —CH(CH₃)—CH(CH₃)₃, —C₇H₁₅, —C₃H₆—C(CH₃)₃, —C₄H₈—CH(CH₃)₂, —C₃H₆—CH(CH₃)—C₂H₅, —C₂H₄—C(CH₃)₂—C₂H₅, —C₂H₄—CH(CH₃)—C₃H₇, —CH₂—C(CH₃)₂—C₃H₇, —CH₂—CH(CH₃)—C₄H₉, —CH(CH₃)—C₅H₁₁, —C₈H₁₇, —C₄H₈—C(CH₃)₃, —C₅H₁₀—CH(CH₃)₂, —C₄H₈—CH(CH₃)—C₂H₅, —C₃H₆—C(CH₃)₂—C₂H₅, —C₃H₆—CH(CH₃)—C₃H₇, —C₂H₄—C(CH₃)₂—C₃H₇, —C₂H₄—CH(CH₃)—C₄H₉, —CH₂—C(CH₃)₂—C₄H₉, —CH₂—CH(CH₃)—C₅H₁₁, —C(CH₃)₂—C₅H₁₁, —CH(CH₃)—C₆H₁₃, —C₉H₁₉, —C₅H₁₀—C(CH₃)₃, —C₆H₁₂—CH(CH₃)₂, —C₅H₁₀—CH(CH₃)—C₂H₅, —C₄H₈—C(CH₃)₂—C₂H₅, —C₄H₈—CH(CH₃)—C₃H₇, —C₃H₆—C(CH₃)₂C₃H₇, —C₃H₆—CH(CH₃)—C₄H₉, —C₂H₄—C(CH₃)₂—C₄H₉, —C₂H₄—CH(CH₃)—C₅H₁₁, —CH₂—C(CH₃)₂—C₅H₁₁, —CH₂—CH(CH₃)—C₆H₁₃, —C(CH₃)₂—C₆H₁₃, —CH(CH₃)—C₇H₁₅, —C₁₀H₂₁, —C₆H₁₂—C(CH₃)₃, —C₇H₁₄—CH(CH₃)₂, —C₆H₁₂—CH(CH₃)—C₂H₅, —C₅H₁₀—C(CH₃)₂—C₂H₅, —C₅H₁₀—CH(CH₃)—C₃H₇, —C₄H₈—C(CH₃)₂—C₃H₇, —C₄H₈—CH(CH₃)—C₄H₉, —C₃H₆—C(CH₃)₂—C₄H₉, —C₃H₆—CH(CH₃)₂—C₅H₁₁, —CH₅H₁₁, —C₅H₁₁, —C₂H₄—C(CH₃)₂—C₅H₁₁, —C₂H₄—CH(CH₃)—C₆H₁₃, —CH₂—C(CH₃)₂—C₆H₁₃, —CH₂—CH(CH₃)—C₇H₁₅, —C(CH₃)₂—C₇H₁₅, —CH(CH₃)—C₈H₁₇, —C₁₁H₂₃, —C₇H₁₄—C(CH₃)₃, —C₈H₁₆—CH(CH₃)₂, —C₇H₁₄—CH(CH₃)—C₂H₅, —C₆H₁₂—C(CH₃)₂—C₂H₅, —C₆H₁₂—CH(CH₃)—C₃H₇, —C₅H₁₀—C(CH₃)₂—C₃H₇, —C₅H₁₀—CH(CH₃)—C₄H₉, —C₄H₈—C(CH₃)₂—C₄H₉, —C₄H₈—CH(CH₃)—C₅H₁₁, —C₃H₆C(CH₃)₂—C₅H₁₁, —C₃H₆—CH(CH₃)—C₆H₁₃, —C₂H₄—C(CH₃)₂—C₆H₁₃, —C₂H₄—CH(CH₃)—C₇H₁₅, —CH₂—C(CH₃)₂—C₇H₁₅, —CH₂—CH(CH₃)—C₈H₁₇, —C(CH₃)₂—C₈H₁₇, —CH(CH₃)—C₉H₁₉, —C₁₂H₂₅, —C₈H₁₆—C(CH₃)₃, —C₉H₁₈—CH(CH₃)₂, —C₈H₁₆—CH(CH₃)—C₂H₅, —C₇H₁₄—C(CH₃)₂—C₂H₅, —C₇H₁₄—CH(CH₃)—C₃H₇, —C₆H₁₂—C(CH₃)₂—C₃H₇, —C₆H₁₂—CH(CH₃)—C₄H₉, —C₅H₁₀—C(CH₃)₂—C₆H₉, —C₅H₁₀—CH(CH₃)—C₅H₁₁, —C₄H₈—C(CH₃)₂C₅H₁₁, —C₄H₈—CH(CH₃)—C₆H₁₃, —C₃H₆—C(CH₃)₂—C₆H₁₃, —C₃H₆—CH(CH₃)—C₇H₁₅, —C₂H₄—C(CH₃)₂—C₇H₁₅, —C₂H₄—CH(CH₃)— C₈H₁₇, CH₂—C(CH₃)₂—C₈H₁₇, —CH₂—CH(CH₃)—C₉H₁₉, —C(CH₃)—C₁₀H₂₁;

an alkyl group, if not stated otherwise, denotes a linear or branched C₁-C₆-alkyl, preferably a linear or branched chain of one to five carbon atoms, a linear or branched C₁-C₆-alkenyl or a linear or branched C₁-C₆-alkinyl group, which can optionally be substituted by one or more substituents R³, preferably by halogen;

the C₁-C₆-alkyl, C₁-C₆-alkenyl and C₁-C₆-alkinyl residue may be selected from the group comprising —CH₃, —C₂H₅, —CH═CH₂, —C≡CH, —C₃H₇, —CH(CH₃)₂, —CH₂—CH═CH₂, —C(CH₃)═CH₂, —CH═CH—CH₃, —C≡C—CH₃, —CH₂—C≡CH, —C₄H₉, —CH₂—CH(CH₃)₂, —CH(CH₃)—C₂H₅, —C(CH₃)₃, —C₅H₁₁, —C₆H₁₃, —C(R³)₃, —CR³(R³')₂, —CR³(R³')R³'', —C₂(R³)₅, —CH₂—C(R³)₃, —CH₂—CR³(R³')₂, —CH₂—CR³(R³')R³'', —C₃(R³)₇, —C₂H₄—C(R³)₃, —C₂H₄—CH═CH₂, —CH═CH—C₂H₅, —CH═C(CH₃)₂, —CH₂—CH═CH—CH₃, —CH═CH—CH═CH₂, —C₂H₄—C≡CH, —C≡C—C₂H₅, —CH₂—C≡C—CH₃, —C≡C—CH═CH₂, —CH═CH—C≡CH, —C≡C—C≡CH, —C₂H₄—CH(CH₃)₂, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —C₃H₆—CH═CH₂, —CH═CH—C₃H₇, —C₂H₄—CH═CH—CH₃, —CH₂—CH═CH—C₂H₅, —CH₂—CH═CH—CH═CH₂, —CH═CH—CH═CH—CH₃, —CH═CH—CH₂—CH═CH₂, —C(CH₃)═CH—CH═CH₂, —CH═C(CH₃)—CH═CH₂, —CH═CH—C(CH₃)═CH₂, —CH₂—CH═C(CH₃)₂, —C(CH₃)═C(CH₃)₂, —C₃H₆—C≡CH, —C≡C—C₃H₇, —C₂H₄—C≡C—CH₃, —CH₂—C≡C—C₂H₅, —CH₂—C≡C—CH═CH₂, —CH₂—CH═CH—C≡CH, —CH₂—C≡C—C≡CH, —C≡C—CH═CH—CH₃, —CH═CH—C≡C—CH₃, —C≡C—C≡C—CH₃, —C≡C—CH₂—CH═CH₂, —CH═CH—CH₂—C≡CH, —C≡C—CH₂—C≡CH, —C(CH₃)═CH—CH═CH₂, —CH═C(CH₃)—CH═CH₂, —CH═CH—C(CH₃)═CH₂, —C(CH₃)═CH—C≡CH, —CH═C(CH₃)—C≡CH, —C≡C—C(CH₃)═CH₂, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —C₄H₈—CH═CH₂, —CH═CH—C₄H₉, —C₃H₆—CH═CH—CH₃, —CH₂—CH═CH—C₃H₇, —C₂H₄—CH═CH—C₂H₅, —CH₂—C(CH₃)═C(CH₃)₂, —C₂H₄—CH═C(CH₃)₂, —C₄H₈—C≡CH, —C≡C—C₄H₉, —C₃H₆—C≡C—CH₃, —CH₂—C≡C—C₃H₇, —C₂H₄—C≡C—C₂H₅; R³, R³' or R³'' being as defined above;

a cycloalkyl group denotes a non-aromatic ring system containing three to eight carbon atoms, preferably four to eight carbon atoms, wherein one or more of the carbon atoms in the ring can be substituted by a group X, X being as defined above; the C₃-C₈-cycloalkyl residue may be selected from the group comprising -cyclo-C₃H₅, -cyclo-C₄H₇, -cyclo-C₅H₉, -cyclo-C₆H₁₁, -cyclo-C₇H₁₃, -cyclo-C₈H₁₅;

an alkoxy group denotes an O-alkyl group, the alkyl group being as defined above; the alkoxy group is preferably a methoxy, ethoxy, isopropoxy, t-butoxy or pentoxy group.

an haloalkyl group denotes an alkyl group which is substituted by one to five halogen atoms, the alkyl group being as defined above; the haloalkyl group is preferably a —C(R$^{10}$)$_3$, —CR$^{10}$(R$^{10'}$)$_2$, —CR$^{10}$(R$^{10'}$)R$^{10''}$, —C$_2$(R$^{10}$)$_5$, —CH$_2$—C(R$^{10}$)$_3$, —CH$_2$—CR$^{10}$(R$^{10'}$)$_2$, —CH$_2$—CR$^{10}$(R$^{10'}$)R$^{10''}$, —C$_3$(R$^{10}$)$_7$ or —C$_2$H$_4$—C(R$^{10}$)$_3$, wherein R$^{10}$, R$^{10'}$, R$^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC(R$^{10}$)$_3$, —OCR$^{10}$(R$^{10'}$)$_2$, —OCR$^{10}$(R$^{10'}$)R$^{10''}$, —OC$_2$(R$^{10}$)$_5$, —OCH$_2$—C(R$^{10}$)$_3$, —OCH$_2$—CR$^{10}$(R$^{10'}$)$_2$, —OCH$_2$—CR$^{10}$(R$^{10'}$)R$^{10''}$, —OC$_3$(R$^{10}$)$_7$ or —OC$_2$H$_4$—C(R$^{10}$)$_3$, wherein R$^{10}$, R$^{10'}$, R$^{10''}$ represent F, Cl, Br or I, preferably F;

a hydroxyalkylamino group denotes an (HO-alkyl)$_2$-N-group or HO-alkyl-NH- group, the alkyl group being as defined above:

a halogen group is chlorine, bromine, fluorine or iodine;

an aryl group preferably denotes an aromatic group having five to fifteen carbon atoms, which can optionally be substituted by one or more substituents R$^3$, where R$^3$ is as defined above; the aryl group is preferably a phenyl group, —CH$_2$—C$_6$H$_4$, —C$_6$H$_4$—C$_6$H$_4$, —CH=CH—C$_6$H$_4$, —C≡C—C$_6$H$_4$, -o-C$_6$H$_4$—R$^3$, -m-C$_6$H$_4$—R$^3$, -p-C$_6$H$_4$—R$^3$, -o-CH$_2$—C$_6$H$_4$—R$^3$, -m-CH$_2$—C$_6$H$_4$—R$^3$, -p-CH$_2$—C$_6$H$_4$—R$^3$;

a heteroaryl group denotes a 5- or 6-membered heterocyclic group which contains at least one heteroatom like O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl group. This heterocyclic group can optionally be substituted by one or more substituents R$^3$, where R$^3$ is as defined above.

The invention also provides a pharmaceutical composition comprising a compound of Formula (I), (XIII), (X), (XI) or (XII), in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered.

In another aspect, the present invention also provides a method for the treatment or prophylaxis of a condition where there is an advantage in inhibiting quorum sensing which comprises the administration of an effective amount of a compound of Formula (I), (XIII), (X), (XI) or (XII) and physiologically acceptable salts or physiologically functional derivatives thereof. The term "quorum sensing" is intended to describe cell-density dependent gene regulation through a diffusible signal molecule (Fuqua et al., *J. Bacteriol.* 176:269-75, 1994).

The invention is also directed to the use of compounds of Formula (I), (XIII), (X), (XI) or (XII) and of their pharmacologically tolerable salts or physiologically functional derivatives for the production of a medicament or medical device for the prevention and treatment of diseases, where quorum sensing inhibition is beneficial. Furthermore, the invention is also directed to the use of compounds of Formula (I), (XIII), (X), (XI) or (XII) and of their pharmacologically tolerable salts or physiologically functional derivatives for the production of an antibacterial agent for the prevention and treatment of bacterial biofilms in industrial and environmental settings.

In addition, the present invention provides methods for preparing the desired compounds of Formula (I), (XIII), (X), (XI) or (XII).

DETAILED DESCRIPTION OF THE INVENTION

Figure 1:
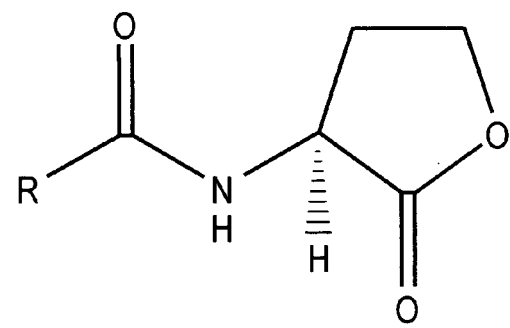
FIG. 1 illustrates the general structure of the N-acyl-L-homoserine lactone.

One possibility for the synthesis of compounds of Formula (I) (n, p=0) or compounds of Formula (XI) comprises the step of reacting an amine of Formula (II) with a compound of Formula (III). Possibilities for preparing different amides are described by J. Zabicky in "The Chemistry of Amides", in the serial of S. Patai (ed.), "The Chemistry of Functional Groups", John Wiley & Sons, 1975, p. 74-131. Methods for preparing thioamides are described in Houben-Weyl, J. Falbe (ed.), G. Thieme Verlag, vol. E5, p. 1219-59. Methods for preparing sulfamides are described by Caldwell et al., *J. Am. Chem. Soc.* 1944, 66, 1479-82, or by Flynn et al, *Med. Chem. Res.*, 1998, 8, 219-43 and Dziadulewicz et al, *Bioorg. Med. Chem. Lett.* 2001, 11, 5, 705-10.

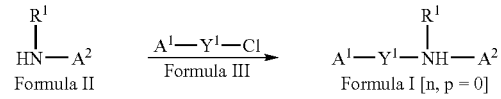

One method for preparing the compounds of Formula (I) (p=0, n=1) or compounds of Formula (X) comprises the step of reacting a compound of Formula (IV) with a compound of Formula (III). Other methods for preparing different 1,2-diacylhydrazines are described in Houben-Weyl, "Methoden der organischen Chemie", Vierte Auflage, G. Thieme Verlag, J. Falbe (ed.). vol. E5, p. 1173-80 or P. A. S. Smith, "Open-Chain Organic Nitrogen Compounds", W. A. Benjamin Inc., New York, vol. 2, p. 173-201. Methods for preparing different 1,2-disulfonylhydrazines are described in *Arch. Pharm.* 1953, 286, 338-43 or in U.S. Pat. No. 6,291,504. Methods for preparing 1-acyl-2-sulfonylhydrazines are described in *Russ. J. Gen. Chem.* 2000, 70, 3, 459-60 or by Leadini et al., *J. Chem. Soc. Perkin Trans. 1* 1998, 1833-8 and by M. Reinecke et al., *J. Org. Chem.* 1988, 53, 1, 208-10.

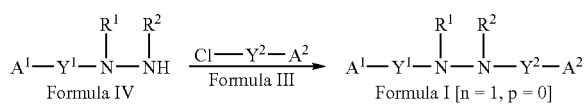

One possibility for the synthesis of compounds of Formula (I) (n,p=1) or compounds of Formula (XII) comprises the step of reacting a compound of Formula (V) with a compound of the Formula (VI). For example, one method for preparing carbamoylhydrazide is described in *Bull. Soc. Chim. Fr.* 1975, 864.

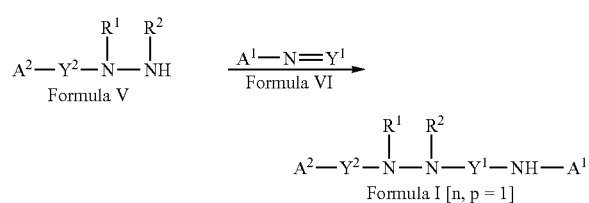

One possibility for preparing the compounds of Formula (XIII) ($A^7$, $A^9$=CO, $A^8$=$CH_2$) comprises the step of reacting a compound of Formula XIV with a compound of the Formula XV. For example, this method is described in *Synthesis* 1992, 1213-1214.

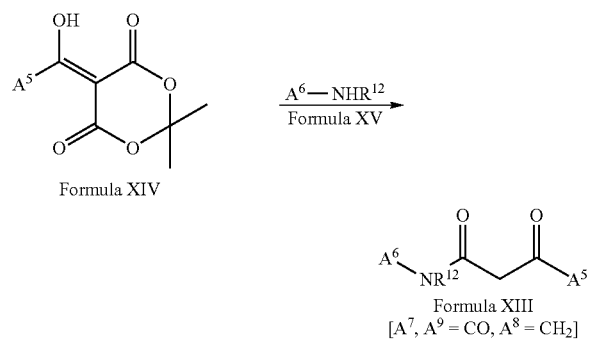

One method for preparation of compounds of Formula (XIV) comprises the step of reacting a carboxylic acid chloride with Meldrum's acid in presence of a base. For example, this reaction is described in *Org. Synth., Coll. Vol.* 7, 359-360 (*Org. Synth.* 1984, *Ann. Vol.* 63, 198-199), or *J. Org. Chem.* 1978, 43, 2087-2088, and *Bull. Chem. Soc. Jpn.* 1982, 55, 2186-2189.

Another possibility for preparing compounds of Formula (XIII) ($A^7$, $A^9$=CO, $A^8$=$CH_2$) comprises the reaction of a 3-oxo carboxylic acid chloride with a compound of Formula (XV). For example, this procedure is described in *Chem. Pharm. Bull.* 1980, 28, 2494-2502.

Another possibility for preparing compounds of Formula (XIII) ($A^7$, $A^9$=CO, $A^8$=$CH_2$) comprises the reaction of a 3-oxo carboxylic acid ester with a compound of Formula (XV). For example, this procedure is described in *Gazz. Chim. Ital.* 1936, 66, 723-731.

Another possibility for preparing the compounds of Formula (XIII) ($A^7$, $A^9$=CO, $A^8$=$CH_2$) comprises the reaction of a 3-oxo carboxylic acid with or without 3-oxo protection with a compound of Formula (XV) using a peptide coupling method. For example, this procedure is described in *Tetrahedron Lett.* 1996, 37, 1883-1884, and *Chem. Biol.* 2003, 10, 81-89.

Another possibility for preparing compounds of Formula (XIII) ($A^7$, $A^9$=CO, $A^8$=$CH_2$) comprises the reaction of a deprotonated methyl ketone with an isocyanate. For example, this method is described in *J. Med. Chem.* 1993, 36, 2943-2949, or *J. Med Chem.* 1993, 36, 3386-3396.

Other methods for preparing compounds of Formula (XIII) are described in *Chem. Pharm. Bull.* 1984, 32, 3848-3856, or *Tetrahedron Lett.* 2001, 5195-5197, and *J. Am. Chem. Soc.* 1995, 117, 12360-12361.

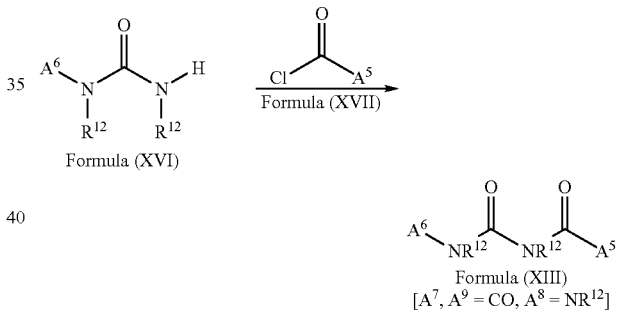

One possibility for preparing the compounds of Formula (XIII) ($A^7$, $A^9$=CO, $A^8$=$NR^{12}$) comprises the step of reacting a compound of Formula (XVI) with a compound of Formula (XVII). For example, this method is described in *Farmaco Ed. Sci.* 1982, 37, 335-342, or in *Monatsh. Chemie* 1981, 112, 871-874, or in *Monatsh. Chemie* 1982, 113, 101-110, or in *J. Am. Chem. Soc.* 2000, 122, 8155-8167, or in *Synth. Commun.* 1989, 19, 3543-3552.

A preferred compound of Formula (I) is a compound wherein p, and n are 0, $A^1$ represents a substituted monocyclic aromatic ring system, and $A^2$ represents an optionally substituted monocyclic aromatic ring system.

A preferred compound of Formula (I) is a compound wherein p, and n are 0, $A^1$ represents a substituted monocyclic aromatic ring system, and $A^2$ represents an optionally substituted alkyl group.

A more preferred compound of Formula (I) is a compound wherein p is 0 and n is 1, one of $A^1$ and $A^2$ represent an optionally substituted 5-membered aromatic ring system, and the other one of $A^1$ and $A^2$ represent an optionally substituted alkyl group or a substituted monocyclic aromatic ring system.

A more preferred compound of Formula (I) is a compound wherein p is 0 and n is 1, $A^1$ and $A^2$ represent an optionally substituted 5-membered aromatic ring system.

A more preferred compound of Formula (I) is a compound wherein p, and n are 1, one of $A^1$ and $A^2$ represent an optionally substituted 5-membered aromatic ring system, and the other one of $A^1$ and $A^2$ represent an optionally substituted alkyl group or a substituted monocyclic aromatic ring system.

A more preferred compound of Formula (I) is a compound wherein p, n are 1, $A^1$ and $A^2$ represents an optionally substituted 5-membered aromatic ring system.

A more preferred compound of Formula (I) is a compound wherein p and n are 1, one of $A^1$ and $A^2$ represent an optionally substituted 5-membered aromatic ring system, and the other one of $A^1$ and $A^2$ represent an optionally substituted alkyl group or a substituted monocyclic aromatic ring system.

A more preferred compound of Formula (I) is a compound wherein p and n are 1 $A^1$ and $A^2$ represent an optionally substituted 5-membered aromatic ring system.

In the compounds of Formula (I), R is independently H, alkyl, cycloalkyl, aryl or heteroaryl. Preferably, R is H.

In the compounds of Formula (I), $R^1$ is independently H, alkyl, cycloalkyl, aryl or heteroaryl. Preferably, $R^1$ is H.

In the compounds of Formula (I), $R^2$ is independently H, alkyl, cycloalkyl, aryl or heteroaryl. Preferably, $R^2$ is H.

Preferably, $R^3$ in Formula (XIII), (I), (X), (XI) or (XII) is independently H, halogen, $CF_3$, $OCF_3$, phenyl or alkyl.

$R^4$ in Formula (XIII), (I), (X) or (XII) is independently H, alkyl, cycloalkyl, aryl or heteroaryl. Preferably $R^4$ is H.

$R^5$ in Formula (XIII), (I), (X) or (XII) is independently H, O-alkyl, O-aryl, alkyl, heteroaryl or aryl. Preferably $R^5$ is H.

In Formula (I) $Y^1$ and $Y^2$ are independently from each other CO, CS, $SO_2$ or $CNR^5$, preferably both are CO.

In Formula (I) Z is independently S, O, N, $NR^4$, CO, $CO_2$, CS, SO or $SO_2$. Preferably, Z is O, CO, $CO_2$.

In Formula (I) or (X) X is independently S, O, N, $NR^4$, SO or $SO_2$. Preferably, X is N, S, O, $NR^4$.

In Formula (I), most preferably, n is 1 and p is 0.

In Formula (I), more preferably, n and p are 0.

In Formula (I), most preferably, n and p are 1.

In Formula (XII), most preferably q is 1 or 2.

A preferred compound of Formula (XIII) is a compound wherein $R^{14}$ is H or methyl more preferably H.

A preferred compound of Formula (XIII) is a compound wherein $R^{12}$ is H or methyl more preferably H.

A preferred compound of Formula (XIII) is a compound wherein $A^8$ is $CH_2$.

A preferred compound of Formula (XIII) is a compound wherein $A^7$ and/or $A^9$ are CO.

A preferred compound of Formula (XIII) is a compound wherein $A^5$ is $C_6$-$C_{10}$-alkyl.

A preferred compound of Formula (XIII) is a compound wherein $A^6$ is selected from the following group:

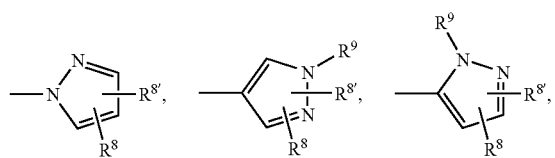

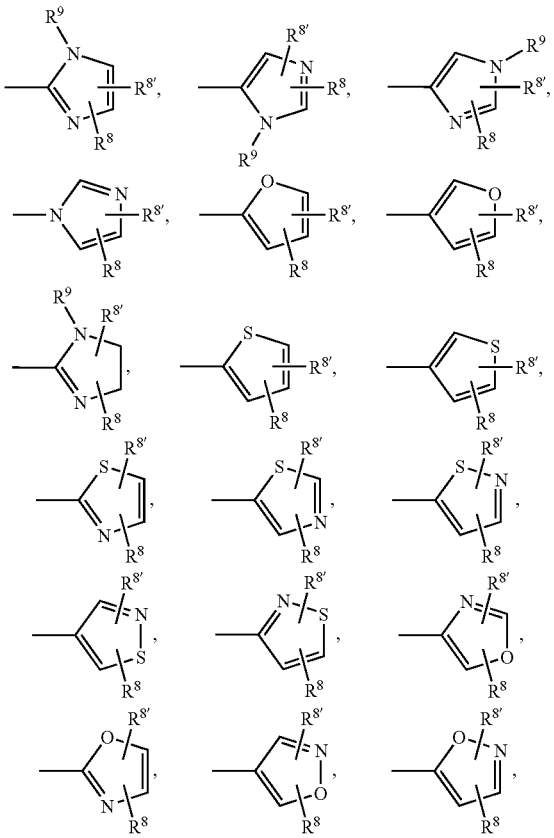

-continued

A preferred compound of Formula (XIII) is a compound wherein $A^6$ is 5-membered ring system wherein X' is N, and X" is O or S, and X'" is CH or $CH_2$.

A preferred compound of Formula (XIII) is a compound wherein $A^6$ is 5-membered ring system wherein X' is N and X" is N, and X'" is CH or $CH_2$.

A preferred compound of Formula (XIII) is a compound wherein $A^6$ is 6-membered ring system wherein X' is N, and X" is O or S, and X'" is CH or $CH_2$, and X"" is CH or $CH_2$.

A preferred compound of Formula (XIII) is a compound wherein $A^6$ is 6-membered ring system wherein X' is N and X" is N, and X'" is CH or $CH_2$, and X"" is CH or $CH_2$.

A preferred compound of Formula (XIII) is a compound wherein m is 1 and q, r are 0.

A preferred compound of Formula (XIII) is a compound wherein $R^{13}$ is H.

A preferred compound of Formula (XIII) is a compound wherein $R^8$, $R^{8'}$ or $R^9$ are H.

Most preferred is the use of one or more compounds of Formula (I), (X), (XI) or (XII), including the compounds excluded by any of the disclaimers, and/or pharmaceutically acceptable salts thereof for regulation of the quorum sensing system of microorganisms, in particular gram-negative bacteria. In one embodiment of the invention also the use of the following compounds is preferred:

2-Chloro-4-trifluoromethyl-pyrimidine-5-carboxylic acid (2-methyl-2H-pyrazol-3-yl)-amide; 2,5-Dichloro-thiophene-3-carboxylic acid pyridin-3-ylamide; 2-[(2-Chloro-4-trifluoro-methyl-pyrimidine-5-carbonyl)-amino]-thiophene-3-carboxylic acid methyl ester; 2-Chloro-4-trifluoromethyl-pyrimidine-5-carboxylic acid (3-trifluoromethyl-phenyl)-amide; 2-Chloro-4-trifluoromethyl-pyrimidine-5-carboxylic acid (4-trifluoromethoxy-phenyl)-amide; 2-Methyl-6-trifluoromethyl-nicotinic acid N'-(thiophene-2-carbonyl)-hydrazide; 4-Trifluoromethyl-benzoic acid N'-(4-methyl-thiophene-2-carbonyl)-hydrazide; 4-Chloro-benzoic acid N'-(4-methoxy-thiophene-3-carbonyl)-hydrazide; 3-Chloro-benzoic acid N'-(thiophene-2-carbonyl)-hydrazide; N'-(3-Methyl-1,4-dioxy-quinoxaline-2-carbonyl)-thiophene-2-carboxylic acid hydrazide; Furan-2-carboxylic acid N'-(thiophene-2-carbonyl)-hydrazide, Furan-2-carboxylic acid N'-(3-chloro-4-methyl-thiophene-2-carbonyl)-hydrazide; Furan-2-carboxylic acid N'-(3-ethoxy-thiophene-2-carbonyl)-hydrazide; Furan-2-carboxylic acid N'-(3-chloro-benzo[b]thiophene-2-carbonyl)-hydrazide: Thiophene-2-carboxylic acid N'-(5-bromo-4-methoxy-thiophene-3-carbonyl)-hydrazide; Thiophene-2-carboxylic acid N'-(3-chloro-4-methyl-thiophene-2-carbonyl)-hydrazide; Thiophene-2-carboxylic acid N'-(thiophene-2-carbonyl)-hydrazide; 3-Chloro-thiophene-2-carboxylic acid N'-(thiophene-2-carbonyl)-hydrazide; Thiophene-2-carboxylic acid N'-(5-bromo-thiophene-2-carbonyl)-hydrazide; 3-Chloro-benzo[b]thiophene-2-carboxylic acid N'-(thiophene-2-carbonyl)-hydrazide; Thiophene-2-carboxylic acid N'-(4-bromo-1,5-dimethyl-1H-pyrazole-3-carbonyl)-hydrazide; Thiophene-2-carboxylic acid N'-butyryl-hydrazide.

Preferred compounds of the present invention and/or pharmaceutically acceptable salts thereof are selected from the group comprising;

3-Oxo-nonanoic acid (2H-pyrazol-3-yl)-amide; 3-Oxo-nonanoic acid (2methyl-2H-pyrazol-3-yl)-amide; 3-Oxo-dodecanoic acid (2-methyl-2H-pyrazol-3-yl)-amide; 3-Oxo-nonanoic acid (2-ethyl-2H-pyrazol-3-yl)-amide; 3-Oxo-dodecanoic acid (2-ethyl-2H-pyrazol-3-yl)-amide; 3-Oxo-nonanoic acid (2,5-dimethyl-2H-pyrazol-3-yl)-amide; 3-Oxo-dodecanoic acid (2,5-dimethyl-2H-pyrazol-3-yl)-amide;, 3-Oxo-nonanoic acid pyrazol-1-ylamide; 2-(3-Oxo-nonanoylamino)-thiophene-3-carboxylic acid methyl ester; 2(3-Oxo-dodecanoylamino)-thiophene-3-carboxylic acid methyl ester; 4-Methyl-2-(3-oxo-nonanoylamino)-thiophene-3-carboxylic acid ethyl ester: 4-Methyl-2-(3-oxo-dodecanoylamino)-thiophene-3-carboxylic acid ethyl ester; 3-Oxo-nonanoic acid (3-methyl-isothiazol-5-yl)-amide; 3-Oxo-dodecanoic acid (3-methyl-isothiazol-5-yl)-amide; 3-Oxo-nonanoic acid thiazol-2-ylamide; 3-Oxo-dodecanoic acid thiazol-2-ylamide; 3-Oxo-nonanoic acid (5-acetyl-2-methylsulfanyl-thiazol-4yl)-amide; 3-Oxo-nonanoic acid isoxazol-3-ylamide; 3-Oxo-dodecanoic acid isoxazol-3-ylamide; 3-Oxo-nonanoic acid (3-methyl-isoxazol-5-yl)-amide; 3-Oxo-dodecanoic acid (3-methyl-isoxazol-5-yl)-amide; 3-Oxo-nonanoic acid (4-methyl-oxazol-2-yl)-amide; 3-Oxo-nonanoic acid (4cyano-2-methyl-oxazol-5-yl)-amide; 3-Oxo-nonanoic acid (3-cyano-4,5-dimethyl-furan-2-yl)-amide; 3-Oxododecanoic acid (3-cyano-4,5-dimethyl-furan-2-yl)-amide; 5-(3-Oxo-nonanoylamino)-furan-2-carboxylic acid methyl ester 3-Bromo-thiophene-2-carboxylic acid (6-methoxy-pyridin-3-yl)-amide; 4-Methyl-3-[(thiophene-2-carbonyl)-amino]-thiophene-2-carboxylic acid methyl ester; N-(6-Methoxy-pyridin-3-yl)-2-methylsulfanyl-nicotinamide; 5-Bromo-N-(6-methoxy-pyridin-3-yl)-nicotinamide; N-(5-Bromo-pyridin-2-yl)-2,6-dichloro-isonicotinamide; 2-Chloro-6-methyl-N-pyridin-3-yl-isonicotinamide; 4-Bromo-2-ethyl-5-methyl-2H-pyrazole-3-carboxylic acid (2-methyl-2H-pyrazol-3-yl)-amide; 2-tert-Butyl-5-methyl-2H-pyrazole-3-carboxylic acid (2-methyl-2H-pyrazol-3-yl)-amide, Thiophene-2-carboxylic acid [5-(4-chloro-phenyl)-2-methyl-2H-pyrazol-3-yl]-amide; 3-Chloro-N-(2-methyl-5-thiophen-2-yl-2H-pyrazol-3-yl)-benzamide; 6-Bromo-hexanoic acid [5-(4chloro-phenyl)-2-methyl-2H-pyrazol-3-yl]-amide; Heptanoic acid (2-methyl-5-phenyl-2H-pyrazol-3-yl)-amide; 6-Bromo-hexanoic acid (2-methyl-5-phenyl-2H-pyrazol-3-yl)-amide; Heptanoic acid (2-methyl-5-thiophen-2-yl-2H-pyrazol-3-yl)-amide; 6-Bromo-hexanoic acid (2-methyl-5-thiophen-2-yl-2H-pyrazol-3-yl)-amide; Heptanoic acid (4-bromo-2-methyl-2H-pyrazol-3-yl-amide; 6-Bromo-hexanoic acid (2-methyl-2H-pyrazole-3-yl)-amide; 6-Bromo-hexanoic acid (4-bromo-2-methyl-2H-pyrazol-3-yl)-amide; Heptanoic acid (2-methyl-2H-pyrazol-3-yl)-amide; Thiophene-2carboxylic acid N'-(4-trifluoromethyl-pyrimidin-2-yl)-hydrazide; 2,5-Dimethyl-2H-pyrazol-3-carboxylic acid N'-(4-trifluoromethyl-pyrimidin-2-yl)-hydrazide; 4-Trifluoromethoxy-benzoic acid N'-(thiophene-2-carbonyl)-hydrazide; 3-Chloro-thiophene-2-carboxylic acid N'-(1-phenyl-5-trifluoromethyl-1H-pyrazole-4-carbonyl)-hydrazide; Thio-phene-2-carboxylic acid N'-[1-(4-chloro-phenyl)-5-trifluoromethyl-1H-pyrazole-4-carbonyl]-hydrazide; Furan-2-carboxylic acid N'-(5-chloro-4-methoxy-thiophene-3-carbonyl)-hydrazide; Furan-2-carboxylic acid N'-(3-bromo-thiophene-2-carbonyl)-hydrazide; Furan-2-carboxylic acid N'-(2,5-dichloro-thiophene-3-carbonyl)-hydrazide; 3-Chloro-thiophene-2-carboxylic acid N'-(3-ethoxy-thiophene-2-carbonyl)-hydrazide; Thiophene-2-carboxylic acid N'-(3-ethoxy-thiophene-2-carbonyl)-hydrazide; Thiophene-3-carboxylic acid N'-(thiophene-2-carbonyl)-hydrazide; 3-Bromo-thiophene-2-carboxylic acid N'-(2-chloromethylsulfanyl-acetyl)-hydrazide; 3-Chloro-thiophene-2-carboxylic acid N'-(3-chloro-thiophene-2-carbonyl)-hydrazide; 5-Chloro-4-methoxy-thiophene-3-carboxylic acid N'-(thiophene-2-carbonyl)-hydrazide; Thiophene-2-carboxylic acid N'-(5-chloro-thiophene-2-carbonyl)-hydrazide; 5-Bromo-4-methoxy-thiophene-3-carboxylic acid N'-(5-methyl-thiophene-2-carbonyl)-hydrazide; Thiophene-2-carboxylic acid N'-(5-methyl-thiophene-2-carbonyl)-hydrazide; Thiophene-2-carboxylic acid N'-(3-bromo-thiophene-2-carbonyl)-hydrazide; 3-Bromo-thiophene-2-carboxylic acid N'-(3-ethoxy-thiophene-2-carbonyl)-hydrazide; 3-Bromo-thiophene-2-carboxylic acid N'-(5-methyl-thiophene-2-carbonyl)-hydrazide; 3-Chloro-thiophene-2-carboxylic acid N'-(5-chloro-thiophene-2-carbonyl)-hydrazide; 3-Chloro-benzo[b]thiophene-2-carboxylic acid N'-(3-bromo-thiophene-2-carbonyl)-hydrazide; 3-Chloro-benzo[b]thiophene-2-carboxylic acid N'-(5-bromo-thiophene-2-carbonyl)-hydrazide; 4-Chloro-1,3-dimethyl-1H-pyrazolo[3,4-b]-pyridine-5-carboxylic acid N'-(thiophene-2-carbonyl-hydrazide; 2,5-Dimethyl-2H-pyrazole-3-carboxylic acid N'-(3-chloro-benzo[b]thiophene-2-carbonyl)-hydrazide; 2,5-Dimethyl-2H-pyrazole-3-carboxylic acid N'-(thiophene-2-carbonyl)-hydrazide; 4-Bromo-2ethyl-5-methyl-2H-pyrazole-3-carboxylic acid N'-(5-chloro-thiophene-2-carbonyl)-hydrazide; Thiophene-2-carboxylic acid N'-(2-tert-butyl-5-methyl-2H-pyrazole-3-carbonyl)-hydrazide; 5-tert-Butyl-2-methyl-2H-pyrazole-3-carboxylic acid N'-(5-chlorothiophene-2-carbonyl)-hydrazide; Thiophene-2-carboxylic acid N'-(5-tert-butyl-2-methyl-2H-pyrazole-3-carbonyl)-hydrazide; 4Bromo-2-ethyl-5-methyl-2H-pyrazole-3-carboxylic acid N'-(5-bromo-thiophene-2-carbonyl)-hydrazide; 4-Bromo-2-ethyl-5-methyl-2H-pyrazole-3-carboxylic acid N'-(3-chloro-4-methylthiophene-2-carbonyl)-hydrazide; 4-Bromo-2-ethyl-5-methyl-2H-pyrazole-3-carboxylic acid N'-(5-chloro-thiophene-2-carbonyl)-hydrazide; 4-Bromo-2-ethyl-5-methyl-2H-pyrazole-3-carboxylic acid N'-(4,5-di-bromo-thiophene-2-carbonyl)-hydrazide; 5-Methyl-thiophene-2-carboxylic acid N'-butyryl-hydrazide; 5-Bromo-thiophene-2-carboxylic acid N'-butyryl-hydrazide; Thiophene-2-carboxylic acid N'-(6-bromo-hexanoyl)-hydrazide; Thiophene-2-carboxylic acid N'-heptanoyl-hydrazide; 3-Chloro-4-methyl-thiophene-2-carboxylic acid N'-(6-bromo-hexanoyl)-hydrazide; 3-Chloro-4-methyl-thiophene-Z-carboxylic acid N'-heptanoyl-hydrazide; 5-Methyl-thiophene-2-carboxylic acid N'-(6-bromohexanoyl)-hydrazide; 5-Methyl-thiophene-2-carboxylic acid N'-heptanoyl-hydrazide; 5-Bromo-thiophene-2-carboxylic acid N'-heptanoyl-hydrazide; 3-Bromo-thiophene-2carboxylic acid N'-octanoyl-hydrazide; Thiophene-2-carboxylic acid N'-dodecanoyl-hydrazide; 5-Methyl-thiophene-2-carboxylic acid N'-(3-cyclopentyl-propionyl)-hydrazide; 5-[N'-(5-Methyl-thiophene-2-carbonyl)-hydrazino]-5-oxo-pentanoic acid methyl ester; Furan-2-carboxylic acid N'-heptanoyl-hydrazide; Furan-2-carboxylic acid N'-(3-cyclopentyl-propionyl)-hydrazide; 3,5-Dimethyl-isoxazole-4carboxylic acid N'-octanoyl-hydrazide; 4-Bromo-2-ethyl-5-methyl-2H-pyrazole-3-carboxylic acid N'-octanoyl-hydrazide; 2-Chloro-isonicotinic acid N'-octanoyl-hydrazide; 2-Chloro-nicotinic acid N'-octanoyl-hydrazide; 3-[N'-(3-Bromo-thiophene-2-carbonyl)-hydrazino]-3-oxo-propionic acid ethyl ester; 3-[N'-(Benzo[b]thio-phene-2-carbonyl)-hydrazino]-3-oxo-propionic acid ethyl ester; N'-(5-Chloro-thiophen-2-sulfonyl)-thiophene-2-carboxylic acid hydrazide; Butyric acid N'-(5-chloro-thiophen-2-sulfonyl)-hydrazide; N'-(5-Chloro-thiophen-2-sulfonyl)-heptanoic acid hydrazide; 4-Butyl-1-(thiophene-2-carbonyl)-thiosemicarbazide; 1-(4,5-Dibromo-thiophene-2-carbonyl)-4-pentyl-semicarbazide; 1-(5-Bromo-thiophene-2-carbonyl)-4-(4-fluoro-2-trifluoromethyl-phenyl)-semicarbazide; 4-(4-Chloro-3-trifluoromethyl-phenyl)-1-(4,5-dibromo-thiophene-2-carbonyl)-semicarbazide; 1-(4,5-Dibromo-thiophene-2-carbonyl)-4-(3-trifluoromethyl-phenyl)-semicarbazide; 1-(3-Chloro-4-methyl-thiophene-2-carbonyl)-4-(4-methylsulfanyl-phenyl)-semicarbazide; 4-(4-Bromo-phenyl)-1-(3-chloro-4-methyl-thiophene-2-carbonyl)-semicarbazide; 1-(5-Bromo-thiophene2-carbonyl)-4-(2-chloromethyl-phenyl)-semicarbazide; 4(2-Chloro-methyl-phenyl)-1-(5-chloro-thiophene-2-carbonyl)-semicarbazide; 1-(5-Bromo-thiophene-2-carbonyl)-4-(4-methoxy-phenyl)-semicarbazide; 1-(5-Bromo-thiophene-2-carbonyl)-4-(2,6-difluoro-phenyl)-semicarbazide; 1-(3-Chloro-benzo[b]thiophene-2-carbonyl)-4-(2,6-dichloro-pyridinyl)-semicarbazide; 1-(3-Chloro-benzo[b]thiophene-2-carbonyl)-4-o-tolyl-semi-carbazide The compounds of the Formula (XIII), (I), (X), (XI) or (XII) according to the invention can be also used in form of the corresponding salts with inorganic or organic acids or bases. Examples of such salts are, e.g., alkali metal salts, in particular sodium and potassium salts, hydrochloride or ammonium salts.

In general, the compounds of the present invention can be used to inhibit quorum sensing signaling of bacteria employing HSLs as signal molecules for cell-cell communication. Preferably, the compounds can be applied to the bacteria listed in Table 1, and more preferably to the bacteria of Table 1 that are pathogens. In the following it is explained that the compounds of the present invention can be used as antibacterial agents in various applications.

In a preferred form, the compounds of Formula (XIII), (I), (X), (XI) or (XII) are useful for the treatment of a variety of human, animal and plant diseases, where bacterial pathogens regulate the expression of virulence genes and other phenotypes, e.g. biofilm formation, through an HSL-based quorum sensing system. Furthermore, as the list of organisms (see Table 1) employing quorum sensing signaling for their virulence continues to increase, the compounds of the invention can be used also for organisms which will be added to the above listed in future.

In a first embodiment, the compounds are useful for the treatment of mammalian in particular human diseases caused by bacteria through the inhibition of the bacterial quorum sensing cascade rendering the pathogen avirulent. Such diseases include endocarditis, respiratory and pulmonary infections (preferably in immunocompromized and cystic fibrosis patients), bacteremia, central nervous system infections, ear infections including external otitis, eye infections, bone and joint infections, urinary tract infections, gastrointestinal infections and skin and soft tissue infections including wound infections, pyoderma and dermatitis which all can be triggered by *Pseudomonas aeruginosa*. Furthermore, the compounds can be used for the treatment of pulmonary infections caused by *Burkholderia cepacia* (preferably in immunocompromized and cystic fibrosis patients), gastroenteritis and wound infections caused by *Aeromonas hydrophila*, sepsis in tropical and subtropical areas caused by *Chromobacterium violaceum*, diarrhoea with blood and haemolytic uremic syndrome (HUS) caused by *Escherichia coli*, yersiniosis triggered by *Yersinia enterocolitica* and *Y. pseudotuberculosis*, and transfusion-related sepsis and fistulous pyoderma caused by *Serratia liquefaciens*.

In a second embodiment the compounds can be used in the treatment of immunological diseases, particularly autoimmune diseases such as psoriasis, rheumatoid arthritis, multiple sclerosis and type 1 (autoimmune) diabetes, of cardiovascuklar diseases such as cardiac tachyarrhythmias, ischaemic heart disease, congestive heart failure, of allergic diseases and of diseases including cancer, breast cancer, obesity, lipid metabolism disorders, immune disease, immune deficiency or immune disorders.

In a third embodiment, the compounds can be used to prevent and/or treat plant diseases, where inhibition of the HSL-mediated signaling system reduces or abolishes virulence of bacterial plant pathogens. Such diseases include crown gall tumors caused by *Agrobacterium tumefaciens*, soft rot caused by *Burkholderia cepacia*, *Erwinia carotovora* and *Erwinia chrysanthemi*, sweet corn and maize infections caused by *Pantoea stewartii* and wilt disease caused by *Ralstonia solanacearum*.

In a fourth embodiment, the compounds can be used for the prevention and/or treatment of animal diseases, preferably fish diseases such as septicemia caused by *Aeromonas hydrophila* and *Vibrio anguillarum*, furunculosis in salmonids caused by *Aeromonas salmonicida*, prawn infections caused by *Vibrio harveyi* and enteric redmouth disease caused by *Yersinia ruckeri*, but also for the prevention and/or treatment of insect diseases caused, for example, by *Xenorhabdus nematophilus*.

In general, the present invention provides a method for reducing the virulence of bacterial pathogens employing an HSL-based signaling system. In a preferred form, a method is provided to remove, diminish, detach or disperse a bacterial biofilm from a living or nonliving surface by treating the surface with a compound of Formula (XIII), (I), (X), (XI) or (XII). This method is also useful to prevent biofilm formation on a living or nonliving surface by treating the surface with a compound of Formula (XIII), (I), (X), (XI) or (XII) before bacterial colonization can initialize. The term "biofilm" refers to cell aggregations comprising either a single type of organism or a mixture of more than one organism, then also referred to as "mixed biofilms". It is clear to persons skilled in the art, that the compounds of the present invention can be applied in a wide variety of different fields such as environmental, industrial and medical applications in order to prevent and/or treat damages or diseases caused by bacteria.

In one aspect, the compounds of Formula (XIII), (I), (X), (XI) or (XII) can be used for all kinds of surfaces in private and public areas, where it is beneficial to inhibit quorum sensing systems of Gram-negative bacteria in order to prevent and/or treat colonization and biofilm formation. The compounds here can be used in form of a solution, powder or as a coating. The compound is preferably applied to the surface as a solution of the compound, alone or together with other materials such as conventional surfactants, preferably sodium dodecyl sulfate, or detergents, biocides, fungicides, antibiotics, pH regulators, perfumes, dyes or colorants, In combination with a bacteriocidal agent, e.g., the compounds of Formula (XIII), (I), (X), (XI) or (XII) inhibit virulence or biofilm formation whilst the bacteriocidal agent kills the pathogens.

In one embodiment, the compounds can be used as antibacterial agent for topical use in cleaning and treatment solutions such as disinfectants, detergents, household cleaner and washing powder formulations in the form of a spray or a dispensable liquid. In a preferred form, these solutions can be applied to windows, floors, clothes, kitchen and bathroom surfaces and other surfaces in the area of food preparation and personal hygiene. In addition, the compounds of Formula (XIII), (I), (X), (XI) or (XII) can be used as antibacterial ingredients in personal hygiene articles, toiletries and cosmetics such as dentifrices, mouthwashes, soaps, shampoos, shower gels, ointments, creams, lotions, deodorants and disinfectants and storage solutions for contact lenses. In the case of contact lenses the compounds of Formula (XIII), (I), (X), (XI) or (XII) can also be applied as coating or additive to the lens material.

In another embodiment, the compounds can be used to prevent or treat bacterial biofilms in industrial settings such as ship hulls, paper and metal manufacturing, oil recovery, food processing and other applications where process disturbances are referred to biofouling on surfaces. The compounds here can be used in form of a solution, paint or coating, for example as an ingredient in cooling lubricants. The compounds can also be applied to water processing plants or drinking water distribution systems where the colonized surface (preferably by *Pseudomonas aeruginosa*) is preferably the inside of an aqueous liquid system such as water pipes, water injection jets, heat exchangers and cooling towers. Until now biocides are the preferred tools to encounter these problems, but since biocides do not have a high specificity for bacteria, they are often toxic to humans as well. This can be circumvented by the application of the compounds of the present invention.

In a further embodiment, the present invention relates to a method of inhibiting and/or preventing medical device-associated bacterial infections. The invention provides articles coated and/or impregnated with a compound of Formula (XIII), (I), (X), (XI) or (XII) in order to inhibit and/or prevent biofilm formation thereon. The articles are preferably surgical instruments, blood bag systems or medical devices; more preferably either permanently implanted devices such as artificial heart valve, prostethic joint, voice prosthesis, stent, shunt or not permanently implanted devices such as endotracheal or gastrointestinal tube, pacemaker, surgical pin or indwelling catheter.

In a more preferred form, the indwelling catheters are urinary catheters, vascular catheters, peritoneal dialysis catheter, central venous catheters and needleless connectors. The catheter materials can be polyvinylchloride, polyethylene, latex, teflon or similar polymeric materials, but preferably polyurethane and silicone or a mixture thereof. In order to reduce the risk of catheter-related bacterial infections, several catheters coated and/or impregnated with antiseptic or antimicrobial agents such as chlorhexidine/silver-sulfadiazine and minocycline/rifampin, respectively, have been developed. Furthermore, collection bags or layers sandwiched between an external surface sheath and a luminal silicone sheath have been constructed to overcome rapid loss of antimicrobial activity. Nevertheless, the emerging risk of bacterial resistance against traditional antibiotics limits the routine use of antibiotic-coated catheters.

The compounds of the present invention, however, offer the possibility to effectively reduce catheter-related bacterial infections with a low risk of resistance development due to a novel therapeutic strategy targeting highly sensitive signal transduction mechanisms in bacteria. The preferred form of application is the coating and/or impregnating of catheter materials on both the inner and outer catheter surfaces. More preferably, the compounds of Formula (XIII), (I) can be included in a mixture of antibacterial agents released continously from a catheter-associated depot into the environment.

In a further embodiment, the compounds of the present invention and their pharmacologically acceptable salts can be administered directly to animals, preferably to mammals, and in particular to humans as antibiotics per se, as mixtures with one another or in the form of pharmaceutical preparations which allow enteral or parenteral use and which as active constituent contain an effective dose of at least one compound of the Formula (XIII), (I), (X), (XI) or (XII) or a salt thereof, in addition to customary pharmaceutical excipients and additives. The compounds of Formula (XIII), (I), (X), (XI) or (XII) can also be administered in form of their salts, which are obtainable by reacting the respective compounds with physiologically acceptable acids and bases.

The therapeutics can be administered orally, e.g., in the form of pills, tablets, coated tablets, sugar coated tablets, lozenges, hard and soft gelatin capsules, solutions, syrups, emulsions or suspensions or as aerosol mixtures. Administration, however, can also be carried out rectally, e.g., in the form of suppositories, or parenterally, e.g., in the form of injections or infusions, or percutaneously, e.g., in the form of ointments, creams or tinctures.

In addition to the active compounds of Formula (XIII), (I), (X), (XI) or (XII), the pharmaceutical composition can contain further customary, usually inert carrier materials or excipients. Thus, the pharmaceutical preparations can also contain additives or adjuvants commonly used in galenic formulations, such as, e.g., fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for modifying the osmotic pressure, coating agents or antioxidants. They can also contain two or more compounds of the Formula (I)or (XIII) or their pharmacologically acceptable salts and also other therapeutically active substances.

Thus, the compounds of the present invention can be used alone, in combination with other compounds of this invention or in combination with other active compounds, for example with active ingredients already known for the treatment of the afore mentioned diseases, whereby in the latter case a favorable additive effect is noticed. Suitable amounts to be administered to mammalian in particular humans range from 5 to 1000 mg, To prepare the pharmaceutical preparations, pharmaceutically inert inorganic or organic excipients can be used. To prepare pills, tablets, coated tablets and hard gelatin capsules, e.g., lactose, corn starch or derivatives thereof, talc, stearic acid or its salts, etc. can be used. Excipients for soft gelatin capsules and suppositories are, e.g., fats, waxes, semi-solid and liquid polyols, natural or hardened oils etc. Suitable excipients for the production of solutions and syrups are, e.g., water, alcohol, sucrose, invert sugar, glucose, polyols etc. Suitable excipients for the production of injection solutions are, e.g., water, alcohol, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 0.1 to 100 mg/kg animal body weight preferably 1 to 50 mg/kg. Suitable dosage fates for larger mammals, e.g., humans, are of the order of from about 10 mg to 3 g/day, conveniently administered once, in divided doses 2 to 4 times a day, or in sustained release form.

In general, a daily dose of approximately 0.1 mg to 5000 mg, preferably 10 to 500 mg, per mammalian in particular human individual is appropriate in the case of the oral administration which is the preferred form of administration according to the invention. In the case of other administration forms too, the daily dose is in similar ranges. The compounds of Formula (I) or (XIII) can also be used in the form of a precursor (prodrug) or a suitably modified form, that releases the active compound in vivo.

In a further embodiment, the compounds of the present invention can be used as pharmacologically active components or ingredients of medical devices, instruments and articles with an effective dose of at least one compound of the Formula (XIII), (I), (X), (XI) or (XII) or a salt thereof. The amount of the compounds used to coat for example medical device surfaces varies to some extent with the coating method and the application field. In general, however, the concentration range from about 0.01 mg per cm² to about 100 mg per cm². In a similar way the amount of the compounds has to be adjusted to the application mode it the compounds of the invention are used as components or ingredients in cleaning or treatment solutions. In general, effective dosages range from about 0.1 μM to about 1000 mM.

The following section shows examples for the synthesis of the compounds of the present invention and demonstrate their quorum sensing inhibiting effect.

EXAMPLES

1. Synthesis of Compounds of Formula (XIII), (I), (X), or (XII)

Synthesis Method A (1,2diacylhydrazine or 1-acyl-2sulfonylhydrazine Derivatives)

A solution of (1.2 eq) acid chloride or (1.2 eq) sulfonyl chloride in tetrahydrofuran was added to a solution of (1 eq) hydrazide in tetrahydrofuran and molecular sieve (0.4 nm) at 0° C. The mixture was stirred at room temperature. After 1 h the reaction mixture was concentrated in vacuum, and the resulting solid was purified by preparative thin layer chromatography (Merck, 20×20 cm, Silica gel 60 $F_{254}$, 1 mm) ($CH_2Cl_2$:MeOH, 100:1).

Synthesis Method B (1,2-diacylhydrazine or 1-acyl-2-sulfonylhydrazine Derivatives)

A solution of (1.2 eq) acid chloride or (1.2 eq) sulfonyl chloride in dimethylformamide was added to a solution of (1 eq) hydrazide in dimethylformamide and (1.2 eq) triethylamine at 0° C. The mixture was stirred at room temperature. After 1 h the reaction mixture was concentrated in vacuum, and the resulting solid was purified by preparative thin layer chromatography (Merck, 20×20 cm, Silica gel 60 $F_{254}$, 1 mm) ($CH_2Cl_2$:MeOH, 100:1).

Synthesis Method C (1,2diacylhydrazine or 1-acyl-2-sulfonylhydrazine Derivatives)

A solution of (1.2 eq) acid chloride or (1.2 eq) sulfonyl chloride in dichloromethane was added to a solution of (1 eq) hydrazide in dichloromethane and (1.2 eq) triethylamine at 0° C. The mixture was stirred at room temperature. After 1 h the reaction mixture was concentrated in vacuum, and the resulting solid was purified by preparative thin layer chromatography (Merck, 20×20 cm, Silica gel 60 $F_{254}$, 1 mm) (n-hexane:EtOAc, 9:1).

Synthesis Method D (Amide Derivatives)

A solution of (1.2 eq) acid chloride in tetrahydrofuran was added to a solution of (1 eq) amine in tetrahydrofuran and molecular sieve (0.4 nm) at 0° C. The mixture was stirred at room temperature. After 1 h the reaction mixture was concentrated in vacuum, and the resulting solid was purified by preparative thin layer chromatography (Merck, 20×20 cm, Silica gel 60 $F_{254}$, 1 mm) ($CH_2Cl_2$:MeOH, 100:1).

Synthesis Method E (Amide Derivatives)

A solution of (1.2 eq) acid chloride in dichloromethane was added to a solution of (1 eq) amine in dichloromethane and (1.2 eq) triethylamine at 0° C. The mixture was stirred at room temperature. After 1 h the reaction mixture was concentrated in vacuum, and the resulting solid was purified by preparative thin layer chromatography (Merck, 20×20 cm, Silica gel 60 $F_{254}$, 1 mm) (n-hexane:EtOAc, 9:1).

Synthesis Method F (Semicarbazide or Thiosemicarbazide Derivatives)

A solution of (1.3 eq) isocyanate or (1.3 eq) isothiocyanate in tetrahydrofuran was added to a solution of (1 eq) hydrazide in tetrahydrofuran and molecular sieve (0.4 nm) at 0° C. The mixture was stirred at room temperature. After 1 h the reaction mixture was concentrated in vacuum, and the resulting solid was purified by preparative thin layer chromatography (Merck, 20×20 cm, Silica gel 60 $F_{254}$, 1 mm) (CH$_2$Cl$_2$:MeOH, 100:5).

Synthesis Method G (Hydrazide Derivatives)

A solution of (1.2 eq) acid chloride in tetrahydrofuran was added to a solution of (1 eq) hydrazine in tetrahydrofuran and molecular sieve (0.4 nm) at 0° C. The mixture was stirred at room temperature. After 1 h the reaction mixture was concentrated in vacuum, and the resulting solid was purified by preparative thin layer chromatography (Merck, 20×20 cm, Silica gel 60 $F_{254}$, 1 mm) (CH$_2$Cl$_2$:MeOH, 100:1).

Synthesis Method H (β-Ketoamides)

The acyl Meldrum's acid (1.2 eq) was dissolved in anhydrous benzene (concentration approximately 0.4 mol/l), and the amine (1.0 eq) was added. In case of amine hydrochlorides, one equivalent of triethylamine or N,N-diisopropylethylamine was added. The mixture was refluxed until tlc showed complete conversion (typically, 4 to 6 h). The benzene solutions were directly chromatographed on silica gel in an appropriate solvent mixture (isohexane—ethyl acetate, dichloromethane—methanol, or dichloromethane—acetonitrile mixtures). Yields of the purified products typically were in the range fom 30 to 75%.

In the following Table 2, the synthesis method employed in each case for the respective compound or whether the compound was obtained is indicated. Furthermore, the mass found by LC/(+)-ESI and LC/(−)-ESI mass spectrometry, the molecular mass, the NMR data (300.13 MHz, residual solvent peaks were used as internal standards (chloroform, δ7.26; methanol, δ3.31; dimethyl sulfoxide, δ2.49; abbreviations, ψ=pseudo, br.=broad, s=singulet, d=doublet, t=triplet, q=quartet, quint.=quintet, sext.=sextet m$_c$=multiplet centered, m=multiplet, CH$_{ar}$=aromatic H, J=$^1$H-$^1$H coupling constant) and the IC$_{50}$ range as a measure of anti-quorum sensing activity are indicated. The NMR data of the small signals due to enol-tautomers or possible rotamers of the 3-oxo-carboxylic acid amides are not listed.

TABLE 2

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 1 | | Maybridge | — | — | +++ |
| 2 | | E | 313[M + H]$^+$ 311[M − H]$^−$ | δ(CDCl$_3$) = 3.88(s, 3H, OCH$_3$), 6.72(d, J=8.9 Hz, 1H, H-3), 7.03(d, J=5.2 Hz, 1H, H-4'), 7.46(d, J=5.3 Hz, 1H, H-5'), 7.95(dd, J=8.9, 2.7 Hz, 1H, H-4), 8.24(d, J=2.7 Hz, 1H, H-6), 8.65(br.s, 1H, NH) | +++ |
| 3 | | Maybridge | — | — | +++ |
| 4 | | Maybridge | — | — | + |

TABLE 2-continued

Structure and biosensor assay results of the tested compounds.

| # | Compound | Synthesis method/ supplier | HPLC/ MS (ESI) | ¹H-NMR (300 MHz) | IC$_{50}$* |
|---|---|---|---|---|---|
| 5 | [structure] | D | 282[M + H]⁺ 280[M − H]⁻ | δ(CD$_3$OD) = 2.23(s, 3H, CH$_3$), 3.79(s, 3H, 3H, OCH$_3$), 7.06-7.11(m, 2H, H-4 and H-2'), 7.50(dd, J=4.9, 1.1 Hz, 1H, H-3), 7.69(dd, J=3.8, 1.1 Hz, 1H, H-5), 9.71(s, 1H, NH) | + |
| 6 | [structure] | May-bridge | — | — | ++ |
| 7 | [structure] | May-bridge | — | — | +++ |
| 8 | [structure] | E | 276[M + H]⁺ 274[M − H]⁻ | δ(CDCl$_3$) = 2.54(s, 3H, SCH$_3$), 3.86(s, 3H, OCH$_3$), 6.70(d, J=8.9 Hz, 1H, H-3), 7.01(t, J=4.8 Hz, 1H, H-5'), 7.85(d, J=6.3 Hz, 1H, H-4'), 7.97(d, J=8.7 Hz, 1H, H-4), 8.22-8.23(br.s, 2H, H-6 and NH), 8.46(dd, J=4.8, 1.7 Hz, 1H, H-6') | + |
| 9 | [structure] | E | 308[M + H]⁺ 306[M − H]⁻ | δ(CD$_3$OD) = 3.85(s, 3H, OCH$_3$), 6.87(d, J=8.8 Hz, 1H, H-3), 8.10(dd, J=8.9, 2.6 Hz, 1H, H-4), 8.57(d, J=2.5 Hz, 1H, H-6), 8.64(d, J=2.1 Hz, 1H, H-4'), 8.91(d, J=2.2 Hz, 1H, H-6'), 9.13(d, J=1.9 Hz, 1H, H-2'), 10.81(s, 1H, NH) | + |
| 10 | [structure] | E | 346[M + H]⁺ 344[M − H]⁻ | δ(CDCl$_3$) = 7.63(s, 2H, H-3' and H-5'), 7.83(dd, J=8.8, 2.3 Hz, 1H, H-4), 8.17(d, J=8.8 Hz, 1H, H-3), 8.28(d, J=2.3 Hz, 1H, H-6), 8.63(s, 1H, NH) | + |
| 11 | [structure] | E | 248[M + H]⁺ 246[M − H]⁻ | δ(CDCl$_3$) = 2.53(s, 3H, CH$_3$), 7.24(dd, J=8.2, 4.9 Hz, 1H, H-5), 7.82(s, 1H, H-3'), 7.87(s, 1H, H-5'), 8.29(d, J=4.4 Hz, 1H, H-4), 8.36(d, J=8.4 Hz, 1H, H-6), 9.09(s, 1H, H-2), 10.30(br.s, 1H, NH) | +++ |

TABLE 2-continued

Structure and biosensor assay results of the tested compounds.

| # | Compound | Synthesis method/ supplier | HPLC/ MS (ESI) | ¹H-NMR (300 MHz) | IC$_{50}$* |
|---|---|---|---|---|---|
| 12 | | D | 312[M + H]⁺<br>310[M − H]⁻ | δ(CD$_3$OD) =<br>1.40(t, J=7.2 Hz, 3H, NCH$_2$CH$_3$),<br>2.25(s, 3H, CH$_3$),<br>3.82(s, 3H, NCH$_3$),<br>4.33(q, J=7.2 Hz, 2H, NCH$_2$CH$_3$),<br>6.40(br.s, 1H, CH$_{ar}$),<br>7.44(d, J=1.8 Hz, 1H, CH$_{ar}$) | +++ |
| 13 | | D | 262[M + H]⁺<br>260[M − H]⁻ | δ(CD$_3$OD) = 1.66(s, 9H, N-tBu),<br>2.24(s, 3H, CH$_3$),<br>3.75 (s, 3H, NCH$_3$),<br>6.30(br.s, 1H, CH$_{ar}$),<br>6.50(br.s, 1H, CH$_{ar}$),<br>7.43(d, J=2.1 Hz, 1H, CH$_{ar}$) | + |
| 14 | | D | 318[M + H]⁺<br>316[M − H]⁻ | δ(DMSO-d$_6$) = 3.73(s, 3H, NCH$_3$),<br>6.72(s, 1H, H-4'),<br>7.25(dd, J=3.6, 5.1 Hz, 1H, H-4),<br>7.43(d, J=8.3 Hz, 2H, CH$_{ar}$),<br>7.80(d, J=8.7 Hz, 2H, CH$_{ar}$),<br>7.90(dd, J=1.2, 4.8 Hz, 1H, H-3),<br>8.01(dd, J=0.9, 3.9 Hz, 1H, H-5),<br>10.43(s, 1H, NH) | +++ |
| 15 | | D | 218[M + H]⁺<br>216[M − H]⁻ | δ(CD$_3$OD) = 3.65(s, 3H, NCH$_3$),<br>6.44(s, 1H, H-4'),<br>6.92(dd, J=3.6, 5.1 Hz, 1H, H-4"),<br>7.19-7.23(m, 2H, CH$_{ar}$),<br>7.38(t, J=8.1 Hz, 1H, CH$_{ar}$),<br>7.50(d, J=8.1 Hz, 1H, CH$_{ar}$),<br>7.78(d, J=7.8 Hz, 1H, CH$_{ar}$),<br>7.87(d, J=1.8 Hz, 1H, CH$_{ar}$) | +++ |
| 16 | | D | 384[M + H]⁺<br>382[M − H]⁻ | δ(DMSO-d$_6$) = 1.34(m$_c$, 2H, CH$_2$),<br>1.53(m$_c$, 2H, CH$_2$),<br>1.74(m$_c$, 2H, CH$_2$),<br>2.28(t, J=7.2 Hz, 2H, CH$_2$),<br>3.45(t, J=6.6 Hz, 2H, CH$_2$),<br>3.59(s, 3H, NCH$_3$),<br>6.55(s, 1H, H-4),<br>7.33(d, J=8.7 Hz, 2H, CH$_{ar}$),<br>7.65(d, J=8.4 Hz, 2H, CH$_{ar}$),<br>9.86(s, 1H, NH) | +++ |
| 17 | | D | 286[M + H]⁺<br>284[M − H]⁻ | δ(CD$_3$OD) =<br>0.80(t, J=6.6 Hz, 3H, CH$_3$),<br>1.21-1.34(m, 6H, (CH$_2$)$_3$),<br>1.59(quint., J=7.8 Hz, 2H, CH$_2$),<br>2.31(t, J=7.5 Hz, 2H, CH$_2$),<br>3.64(s, 3H, NCH$_3$),<br>6.47(s, 1H, H-4),<br>7.15-7.29(m, 3H, CH$_{ar}$),<br>7.62(d, J=6.9 Hz, 2H, CH$_{ar}$) | +++ |

TABLE 2-continued

Structure and biosensor assay results of the tested compounds.

| # | Compound | Synthesis method/ supplier | HPLC/ MS (ESI) | ¹H-NMR (300 MHz) | IC₅₀* |
|---|---|---|---|---|---|
| 18 | (phenyl-pyrazole-N-methyl, N-acyl chain with Br) | D | 350[M + H]⁺ | δ(DMSO-d₆) = 1.41(m_c, 2H, CH₂), 1.55(m_c, 2H, CH₂), 1.82(m_c, 2H, CH₂), 2.31(t, J=6.9 Hz, 2H, CH₂), 3.51(t, J=6.6 Hz, 2H, CH₂), 3.70(s, 3H, NCH₃), 6.62(s, 1H, H-4), 7.28(t, J=7.5 Hz, 1H, CH_ar), 7.38(t, J=8.4 Hz, 2H, CH_ar), 7.74(t, J=6.9 Hz, 2H, CH_ar), 9.95(s, 1H, NH) | +++ |
| 19 | (thienyl-pyrazole-N-methyl, N-hexanoyl) | D | 292[M + H]⁺ 290[M − H]⁻ | δ(CD₃OD) = 0.81(t, J=6.6 Hz, 3H, CH₃), 1.22-1.33(m, 6H, (CH₂)₃), 1.61(quint., J=7.8 Hz, 2H, CH₂), 2.33(t, J=7.5 Hz, 2H, CH₂), 3.61(s, 3H, NCH₃), 6.38(s, 1H, H-4), 6.93(t, J=4.5 Hz, 1H, H-4'), 7.20(d, J=4.5 Hz, 2H, H-3' and H-5') | +++ |
| 20 | (thienyl-pyrazole-N-methyl, N-acyl with Br) | D | 356[M + H]⁺ 354[M − H]⁻ | δ(CD₃OD) = 1.44(m_c, 2H, CH₂), 1.64(m_c, 2H, CH₂), 1.80(m_c, 2H, CH₂), 2.36(t, J=7.2 Hz, 2H, CH₂), 3.37(t, J=6.6 Hz, 2H, CH₂), 3.62(s, 3H, NCH₃), 6.39(s, 1H, H-4), 6.93(t, J=4.5 Hz, 1H, H-4'), 7.21(d, J=4.5 Hz, 2H, H-3' and H-5') | +++ |
| 21 | (4-bromo-pyrazole-N-methyl, N-hexanoyl) | D | 288[M + H]⁺ 286[M − H]⁻ | δ(CD₃OD) = 0.92(t, J=7.2 Hz, 3H, CH₃), 1.38(m_c, 6H, (CH₂)₃), 1.71(quint., J=7.5 Hz, 2H, CH₂), 2.43(t, J=7.5 Hz, 2H, CH₂), 3.68(s, 3H, NCH₃), 7.45(s, 1H, H-3) | +++ |
| 22 | (pyrazole-N-methyl, N-acyl with Br) | D | 274[M + H]⁺ | δ(CD₃OD) = 1.46(m_c, 2H, CH₂), 1.63(m_c, 2H, CH₂), 1.80(m_c, 2H, CH₂), 2.34(t, J=7.2 Hz, 2H, CH₂), 3.37(t, J=6.6 Hz, 2H, CH₂), 3.61(s, 3H, NCH₃), 6.11(d, J=2.1 Hz, 1H, H-4), 7.29(d, J=2.1 Hz, 1H, H-3) | +++ |
| 23 | (4-bromo-pyrazole-N-methyl, N-acyl with Br) | D | 352[M + H]⁺ | δ(CD₃OD) = 1.50(m_c, 2H, CH₂), 1.66(m_c, 2H, CH₂), 1.79(m_c, 2H, CH₂), 2.37(t, J=7.2 Hz, 2H, CH₂), 3.37(t, J=6.6 Hz, 2H, CH₂), 3.60(s, 3H, NCH₃), 7.36(s, 1H, H-3) | +++ |
| 24 | (pyrazole-N-methyl, N-hexanoyl) | D | 210[M + H]⁺ 208[M − H]⁻ | δ(CD₃OD) = 0.92(t, J=6.6 Hz, 3H, CH₃), 1.34-1.46(m, 6H, (CH₂)₃), 1.72(quint., J=7.8 Hz, 2H, CH₂), 2.42(t, J=7.8 Hz, 2H, CH₂), 3.72(s, 3H, NCH₃), 6.22(d, J=2.1 Hz, 1H, H-4), 7.39(d, J=2.1 Hz, 1H, H-3) | +++ |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 25 | | G | 289[M + H]$^+$ 287[M − H]$^−$ | δ(DMSO-d$_6$) = 7.33-7.37(m, 2H, CH$_{ar}$), 7.80(dd, J=3.6, 5.4 Hz, 2H, CH$_{ar}$), 8.87(d, J=4.8 Hz, 1H, CH$_{ar}$), 9.89(s, 1H, NH), 10.71(s, 1H, NH) | +++ |
| 26 | | G | 301[M + H]$^+$ 299[M − H]$^−$ | δ(DMSO-d$_6$) = 2.19(s, 3H, CH$_3$), 3.95(s, 3H, NCH$_3$), 6.73(s, 1H, H-4), 7.23(d, J=4.8 Hz, 1H, CH$_{ar}$), 8.74(d, J=4.8 Hz, 1H, CH$_{ar}$), 9.76(s, 1H, NH), 10.46(s, 1H, NH) | +++ |
| 27 | | Maybridge | — | — | +++ |
| 28 | | Maybridge | — | — | ++ |
| 29 | | A | 331[M + H]$^+$ 329[M − H]$^−$ | δ(DMSO-d$_6$) = 7.21(t, J=4.5 Hz, 1H, H-4), 7.52(d, J=8.7 Hz, 2H, CH$_{ar}$), 7.85(d, J=4.8 Hz, 1H, H-3), 7.88(d, J=3.6 Hz, 1H, H-5), 8.03(d, J=8.7 Hz, 2H, CH$_{ar}$), 10.57(s, 1H, NH), 10.62(s, 1H, NH) | + |
| 30 | | Maybridge | — | — | + |
| 31 | | Maybridge | — | — | ++ |
| 32 | | Maybridge | — | — | ++ |

TABLE 2-continued

Structure and biosensor assay results of the tested compounds.

| # | Compound | Synthesis method/ supplier | HPLC/ MS (ESI) | ¹H-NMR (300 MHz) | IC₅₀* |
|---|---|---|---|---|---|
| 33 | | B | 415[M + H]⁺<br>413[M − H]⁻ | δ(CD₃OD) =<br>7.15(d, J=5.3 Hz, 1H, H-4),<br>7.53-7.55(m, 2H, CH$_{ar}$),<br>7.61-7.63(m, 3H, CH$_{ar}$),<br>7.80(d, J=5.3 Hz, 1H, H-5),<br>8.19(s, 1H, H-3') | + |
| 34 | | A | 415[M + H]⁺<br>413[M − H]⁻ | δ(CD₃OD) =<br>7.05(t, J=5.1 Hz, 1H, H-4),<br>7.38(d, J=9.0 Hz, 2H, CH$_{ar}$),<br>7.47(d, J=9.0 Hz, 2H, CH$_{ar}$),<br>7.62(dd, J=5.1, 1.2 Hz, 1H, H-3),<br>7.70(dd, J=4.2, 1.5 Hz, 1H, H-5),<br>8.05(s, 1H, H-3') | ++ |
| 35 | | TimTec | 237[M + H]⁺<br>235[M − H]⁻ | δ(DMSO-d₆) =<br>3.45(dd, J=1.8, 3.3 Hz, 1H, CH$_{ar}$),<br>7.23(dd, J=3.6, 4.8 Hz, 1H, CH$_{ar}$),<br>7.29(d, J=3.6 Hz, 1H, CH$_{ar}$),<br>7.87-7.95(m, 3H, CH$_{ar}$),<br>10.44(s, 1H, NH), 10.52(s, 1H, NH) | ++ |
| 36 | | May-bridge | — | — | ++ |
| 37 | | May-bridge | — | — | ++ |
| 38 | | A | 301[M + H]⁺<br>299[M − H]⁻ | δ(DMSO-d₆) = 3.89(s, 3H, OCH₃),<br>6.67(dd, J=1.5, 3.3 Hz, 1H, H-4),<br>7.26(d, J=3.6 Hz, 1H, H-3),<br>7.24(d, J=3.3 Hz, 1H, H-3),<br>7.91(d, J=1.5 Hz, 1H, H-5),<br>7.94(s, 1H, H-3'),<br>10.12(br.s, 1H, NH),<br>10.36(br.s, 1H, NH) | +++ |
| 39 | | A | 315[M + H]⁺<br>313[M − H]⁻ | δ(DMSO-d₆) =<br>6.66(dd, J=1.8, 3.3 Hz, 1H, H-4),<br>7.22(d, J=5.1 Hz, 1H, H-4'),<br>7.24(d, J=3.3 Hz, 1H, H-3),<br>7.58(d, J=5.1 Hz, 1H, H-5'),<br>7.90(d, J=1.8 Hz, 1H, H-5),<br>10.37(br.s, 2H, NH) | +++ |

TABLE 2-continued

Structure and biosensor assay results of the tested compounds.

| # | Compound | Synthesis method/ supplier | HPLC/ MS (ESI) | ¹H-NMR (300 MHz) | IC$_{50}$* |
|---|---|---|---|---|---|
| 40 | | A | 305[M + H]$^+$ 303[M − H]$^-$ | δ(DMSO-d$_6$) = 6.59(dd, J=1.8, 3.3 Hz, 1H, H-4), 7.17(d, J=3.6 Hz, 1H, H-3), 7.39(s, 1H, H-4'), 7.83(d, J=1.8 Hz, 1H, H-5), 10.25(s, 1H, NH), 10.38(s, 1H, NH) | +++ |
| 41 | | TimTec | 321[M + H]$^+$ 319[M − H]$^-$ | δ(DMSO-d$_6$) = 6.52(dd, J=1.8, 3.6 Hz, 1H, H-4), 7.13(dd, J=1.8, 3.6 Hz, 1H, H-3), 7.44-7.47(m, 2H, CH$_{ar}$), 7.76-7.79(m, 2H, CH$_{ar}$), 7.99(m$_c$, 1H, H-5), 10.35(s, 1H, NH), 10.42(s, 1H, NH) | +++ |
| 42 | | May-bridge | — | — | +++ |
| 43 | | May-bridge | — | — | +++ |
| 44 | | B | 331[M + H]$^+$ 329[M − H]$^-$ | δ(CDCl$_3$) = 1.51(t, J=7.0 Hz, 3H, OCH$_2$CH$_3$), 4.24(q, J=7.1 Hz, 2H, OCH$_2$CH$_3$), 6.80(d, J=5.4 Hz, 1H, H-4), 6.96(d, J=5.3 Hz, 1H, H-4'), 7.41(d, J=5.4 Hz, 1H, H-5), 7.46(d, J=5.3 Hz, 1H, H-5'), 9.97(d, J=7.3 Hz, 1H, NH), 10.15(d, J=7.3 Hz, 1H, NH) | + |
| 45 | | B | 297[M + H]$^+$ 295[M − H]$^-$ | δ(CDCl$_3$) = 1.50(t, J=7.0 Hz, 3H, OCH$_2$CH$_3$), 4.25(q, J=7.0 Hz, 2H, OCH$_2$CH$_3$), 6.80(d, J=5.5 Hz, 1H, H-4), 7.01(dd, J=6.0, 3.8 Hz, 1H, H-4'), 7.40(d, J=5.4 Hz, 1H, H-5), 7.43(d, J=3.9 Hz, 1H, H-3'), 7.62(d, J=3.9 Hz, 1H, H-5'), 9.50(br.s, 1H, NH), 9.90(d, J=5.3 Hz, 1H, NH) | +++ |
| 46 | | AsInEx | — | — | ++ |
| 47 | | A | 253[M + H]$^+$ 251[M − H]$^-$ | δ(CD$_3$OD) = 7.06(t, J=3.9 Hz, 1H, H-4), 7.41-7.48(m, 2H, H-4' and H-5'), 7.63(d, J=4.8 Hz, 1H, H-3), 7.72(d, J=4.8 Hz, 1H, H-5), 8.08(s, 1H, H-2') | +++ |

TABLE 2-continued

Structure and biosensor assay results of the tested compounds.

| # | Compound | Synthesis method/ supplier | HPLC/ MS (ESI) | ¹H-NMR (300 MHz) | IC$_{50}$* |
|---|---|---|---|---|---|
| 48 | | A | 365[M + H]⁺ 363[M − H]⁻ | δ(CDCl$_3$) = 6.87(d, J=4.1 Hz, 1H, H-2'), 7.03(d, J=5.2 Hz, 1H, H-1), 7.47(d, J=5.2 Hz, 1H, H-2), 7.49(d, J=4.1 Hz, 1H, H-1') | ++ |
| 49 | | A | 319[M − H]⁻ | δ(CD$_3$OD) = 7.21(d, J=5.4 Hz, 2H, H-4 and H-4'), 7.84(d, J=5.4 Hz, 2H, H-5 and H-5') | ++ |
| 50 | | B | 315[M − H]⁻ | δ(CD$_3$OD) = 4.05(s, 3H, OCH$_3$), 7.16(dd, J=5.1, 3.9 Hz, 1H, H-4'), 7.72(dd, J=5.1, 1.2 Hz, 1H, H-3'), 7.81(dd, J=3.9, 1.2 Hz, 1H, H-5'), 7.96(s, 1H, H-5) | ++ |
| 51 | | SPECS and Bio-SPECS | — | — | ++ |
| 52 | | A | 285[M − H]⁻ | δ(DMSO-d$_6$) = 7.08(d, J=3.9 Hz, 1H, H-4'), 7.13(d, J=4.2 Hz, 1H, H-4), 7.68(d, J=3.9 Hz, 1H, H-3), 7.74(d, J=3.9 Hz, 1H, H-3'), 7.78(d, J=3.2 Hz, 1H, H-5'), 10.55(s, 2H, NH) | ++ |
| 53 | | A | 375[M + H]⁺ 373[M − H]⁻ | δ(CD$_3$OD) = 2.44(s, 3H, CH$_3$), 3.93(s, 3H, OCH$_3$), 6.75(dd, J=1.2, 3.9 Hz, 1H, H-4), 7.52(d, J=3.6 Hz, 1H, H-3), 8.01(s, 1H, H-5') | +++ |
| 54 | | A | 267[M + H]⁺ 265[M − H]⁻ | δ(CD$_3$OD) = 2.52(s, 3H, CH$_3$), 6.84(d, J=3.3 Hz, 1H, H-4'), 7.16(t, J=4.8 Hz, 1H, H-4), 7.61(d, J=3.6 Hz, 1H, H-3'), 7.72(d, J=4.8 Hz, 1H, H-3), 7.80(d, J=4.2 Hz, 1H, H-5) | +++ |
| 55 | | A | 331[M + H]⁺ 329[M − H]⁻ | δ(CD$_3$OD) = 7.04-7.08(m, 2H, H-4 and H-4'), 7.58-7.65(m, 2H, H-5 and H-3'), 7.70(d, J=3.6 Hz, 1H, H-5') | +++ |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 56 | | B | 375[M + H]$^+$<br>373[M − H]$^−$ | δ(CD$_3$OD) =<br>1.41(t, J=6.9 Hz, 3H, CH$_3$),<br>4.27(q, J=6.9 Hz, 2H, OCH$_2$),<br>6.98(d, J=5.4 Hz, 1H, CH$_{ar}$),<br>7.07(d, J=5.4 Hz, 1H, CH$_{ar}$),<br>7.59(d, J=5.7 Hz, 1H, CH$_{ar}$),<br>7.63(d, J=5.4 Hz, 1H, CH$_{ar}$) | +++ |
| 57 | | A | 345[M + H]$^+$<br>343[M − H]$^−$ | δ(CD$_3$OD) = 2.64(s, 3H, CH$_3$),<br>6.96(dd, J=0.9, 3.6 Hz, 1H, CH$_{ar}$),<br>7.26(d, J=5.1 Hz, 1H, CH$_{ar}$),<br>7.72(d, J=3.6 Hz, 1H, CH$_{ar}$),<br>7.82(d, J=5.1 Hz, 1H, CH$_{ar}$) | +++ |
| 58 | | A | 319[M − H]$^−$ | δ(DMSO-d$_6$) =<br>7.10(d, J=5.1 Hz, 1H, H-4),<br>7.13(d, J=4.2 Hz, 1H, H-4'),<br>7.60(d, J=3.9 Hz, 1H, H-3'),<br>7.80(d, J=5.1 Hz, 1H, H-5) | ++ |
| 59 | | TimTec | — | — | +++ |
| 60 | | TimTec | — | — | +++ |
| 61 | | B | 415[M + H]$^+$<br>413[M − H]$^−$ | δ(CD$_3$OD) =<br>7.01(d, J=5.4 Hz, 1H, H-4'),<br>7.39-7.43(m, 2H, CH$_{ar}$),<br>7.56(d, J=5.1 Hz, 1H, H-5'),<br>7.78-7.82(m, 2H, CH$_{ar}$) | ++ |
| 62 | | B | 413[M − H]$^−$ | δ(CDCl$_3$) =<br>7.03(d, J=3.7 Hz, 1H, H-4),<br>7.40(d, J=3.2 Hz, 1H, H-3),<br>7.45-7.48(m, 2H, CH$_{ar}$),<br>7.77-7.87(m, 2H, CH$_{ar}$),<br>9.14(s, 1H, NH), 9.79(s, 1H, NH) | ++ |
| 63 | | B | 350[M + H]$^+$<br>348[M − H]$^−$ | δ(CD$_3$OD) =<br>2.73(s, 3H, CH$_3$),<br>4.05(s, 3H, NCH$_3$),<br>7.18(dd, J=5.1, 3.6 Hz, 1H, H-4'),<br>7.75(dd, J=5.1, 1.2 Hz, 1H, H-3'),<br>7.83(dd, J=3.6, 1.2 Hz, 1H, H-5'),<br>8.68(s, 1H, H-6) | + |

TABLE 2-continued

Structure and biosensor assay results of the tested compounds.

| # | Compound | Synthesis method/ supplier | HPLC/ MS (ESI) | ¹H-NMR (300 MHz) | IC₅₀* |
|---|---|---|---|---|---|
| 64 | | B | 347[M − H]⁻ | δ(CD₃OD) = 2.28(s, 3H, CH₃), 4.08(s, 3H, NCH₃), 6.70(s, 1H, H-4), 7.57-7.62(m, 2H, CH_ar), 7.96-8.01(m, 2H, CH_ar) | + |
| 65 | | May-bridge | — | — | +++ |
| 66 | | B | 265[M + H]⁺ 263[M − H]⁻ | δ(CD₃OD) = 2.25(s, 3H, CH₃), 4.04(s, 3H, NCH₃), 6.65(s, 1H, H-4), 7.17(dd, J=5.1, 3.9 Hz, 1H, H-4'), 7.73(dd, J=5.1, 0.9 Hz, 1H, H-3'), 7.79(d, J=3.9 Hz, 1H, H-5') | + |
| 67 | | A | 391[M + H]⁺ 389[M − H]⁻ | δ(CDCl₃) = 1.33(t, J=7.1 Hz, 3H, NCH₂CH₃), 1.83(s, 3H, CH₃), 4.42(dd, J=14.3, 7.2 Hz, 2H, NCH₂CH₃), 6.85(d, J=4.1 Hz, 1H, H-4), 7.44(d, J=4.1 Hz, 1H, H-3) | + |
| 68 | | A | 305[M − H]⁻ | δ(CD₃OD) = 1.68(s, 9H, —C(CH₃)₃), 2.86(s, 3H, CH₃), 6.47(s, 1H, H-4'), 7.17(t, J=3.9 Hz, 1H, H-4), 7.74(dd, J=4.2, 0.9 Hz, 1H, H-3), 7.82(dd, J=3.6, 0.9 Hz, 1H, H-5) | + |
| 69 | | B | 341[M + H]⁺ 339[M − H]⁻ | δ(CDCl₃) = 1.22(s, 9H, tBu), 4.00(s, 3H, NCH₃), 6.58(s, 1H, H-4'), 6.81(d, J=3.9 Hz, 1H, H-4), 7.44(d, J=3.9 Hz, 1H, H-2) | +++ |
| 70 | | A | 307[M + H]⁺ 305[M − H]⁻ | δ(CD₃OD) = 1.33(s, 9H, —C(CH₃)₃), 4.08(s, 3H, NCH₃), 6.80(s, 1H, H-4'), 7.18(t, J=3.6 Hz, 1H, H-4), 7.75(dd, J=5.1, 1.2 Hz, 1H, H-3), 7.82(d, J=3.6 Hz, 1H, H-5) | + |

TABLE 2-continued

Structure and biosensor assay results of the tested compounds.

| # | Compound | Synthesis method/ supplier | HPLC/ MS (ESI) | ¹H-NMR (300 MHz) | IC$_{50}$* |
|---|---|---|---|---|---|
| 71 | (structure) | A | 435[M + H]⁺ 433[M − H]⁻ | δ(CD$_3$OD) = 1.31(t, J=7.5 Hz, 3H, NCH$_2$CH$_3$), 2.13(s, 3H, CH$_3$), 4.23(q, J=7.2 Hz, 2H, NCH$_2$CH$_3$), 7.10(d, J=4.2 Hz, 1H, H-4), 7.48(d, J=3.9 Hz, 1H, H-3) | +++ |
| 72 | (structure) | A | 405[M + H]⁺ 403[M − H]⁻ | δ(CD$_3$OD) = 1.29(t, J=6.9 Hz, 3H, NCH$_2$CH$_3$), 2.12(s, 3H, CH$_3$), 2.13(s, 3H, CH$_3$), 4.23(q, J=7.2 Hz, 2H, NCH$_2$CH$_3$), 7.36(s, 1H, H-5) | + |
| 73 | (structure) | A | 391[M + H]⁺ 389[M − H]⁻ | δ(CD$_3$OD) = 1.28(t, J=7.2 Hz, 3H, NCH$_3$CH$_3$), 2.10(s, 3H, CH$_3$), 4.20(q, J=6.9 Hz, 2H, NCH$_2$CH$_3$), 6.94(d, J=4.2 Hz, 1H, H-4), 7.50(d, J=4.2 Hz, 1H, H-3) | +++ |
| 74 | (structure) | A | 513[M + H]⁺ 511[M − H]⁻ | δ(DMSO-d$_6$) = 1.37(t, J=7.2 Hz, 3H, NCH$_2$CH$_3$), 2.23(s, 3H, CH$_3$), 4.28(q, J=7.2 Hz, 2H, NCH$_2$CH$_3$), 7.94(s, 1H, H-3), 10.75(s, 1H, NH), 11.09(s, 1H, NH) | + |
| 75 | (structure) | TimTec | 213[M + H]⁺ 211[M − H]⁻ | δ(CD$_3$OD) = 0.90(t, J=7.5 Hz, 3H, CH$_3$), 1.60(sext., J=7.5 Hz, 2H, CH$_2$), 2.18(t, J=7.2 Hz, 2H, CH$_2$), 7.04(dd, J=3.9, 5.1 Hz, 1H, H-4), 7.60(dd, J=3.9, 5.1 Hz, 1H, H-3), 7.65(dd, J=3.9, 5.1 Hz, 1H, H-5) | +++ |
| 76 | (structure) | A | 227[M + H]⁺ 225[M − H]⁻ | δ(CD$_3$OD) = 1.01(t, J=7.5 Hz, 3H, CH$_3$), 1.71(sext., J=7.5 Hz, 2H, CH$_2$), 2.28(t, J=7.5 Hz, 2H, CH$_2$), 2.52(s, 3H, CH$_3$), 6.82(d, J=3.9 Hz, 1H, H-4), 7.57(d, J=3.6 Hz, 1H, H-3) | ++ |
| 77 | (structure) | A | 291[M + H]⁺ 289[M − H]⁻ | δ(CD$_3$OD) = 0.90(t, J=7.5 Hz, 3H, CH$_3$), 1.59(sext., J=7.8 Hz, 2H, CH$_2$), 2.17(t, J=7.5 Hz, 2H, CH$_2$), 7.05(d, J=3.9 Hz, 1H, H-4), 7.43(d, J=4.2 Hz, 1H, H-3) | +++ |

TABLE 2-continued

Structure and biosensor assay results of the tested compounds.

| # | Compound | Synthesis method/ supplier | HPLC/ MS (ESI) | ¹H-NMR (300 MHz) | $IC_{50}$* |
|---|---|---|---|---|---|
| 78 | 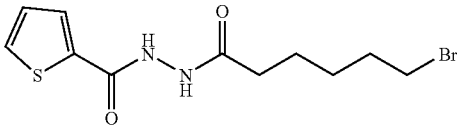 | A | 319[M + H]⁺ | δ(DMSO-$d_6$) = 1.41($m_c$, 2H, H-3'), 1.56($m_c$, 2H, H-2'), 1.81($m_c$, 2H, H-4'), 2.17(t, J=7.2 Hz, 2H, H-1'), 3.52(t, J=6.6 Hz, 2H, H-5'), 7.16(t, J=4.5 Hz, 1H, H-4), 7.81(d, J=4.2 Hz, 2H, H-312 and H-5), 9.82(s, 1H, NH), 10.28(S, 1H, NH) | +++ |
| 79 | 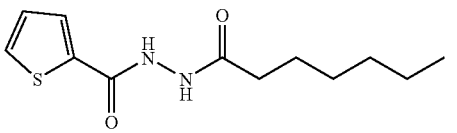 | A | 255[M + H]⁺ 253[M − H]⁻ | δ(DMSO-$d_6$) = 0.86(t, J =6.9 Hz, 2H, H-6'), 1.20-1.36(m, 6H, H-3', H-4' and H-5'), 1.53($m_c$, 2H, H-2'), 2.17(t, J=7.2 Hz, 2H, H-1'), 7.16(t, J=4.5 Hz, 1H, H-4), 7.80-7.84(m, 2H, H-3 and H-5), 9.79(s, 1H, NH), 10.27(s, 1H, NH) | +++ |
| 80 | 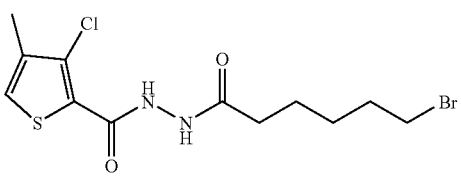 | C | 367[M + H]⁺ 365[M − H]⁻ | δ(CDCl₃) = 1.45($m_c$, 1H, H-3'), 1.68($m_c$, 1H, H-2'), 1.80($m_c$, 1H, H-4'), 2.17(s, 3H, CH₃), 2.35(t, J=7.4 Hz, 1H, H-1'), 3.33(t, J=6.7 Hz, 1H, H-5'), 7.19(s, 1H, H-5), 9.66(d, J=6.4 Hz, 1H, NH), 9.82(d, J=6.3 Hz, 1H, NH) | +++ |
| 81 | 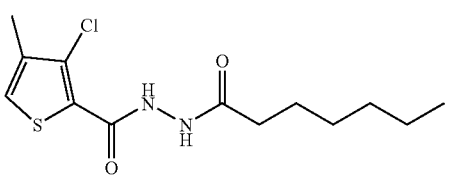 | C | 303[M + H]⁺ 301[M − H]⁻ | δ(CDCl₃) = 0.80(t, J=6.7 Hz, 1H, H-6'), 1.18-1.28(m, 3H, H-3', H-4' and H-5'), 1.62($m_c$, 1H, H-2'), 2.16(s, 3H, CH₃), 2.31(t, J=7.4 Hz, 1H, H-1'), 7.19(s, 1H, H-5), 9.60(d, J=6.5 Hz, 1H, NH), 9.84(d, J=6.4 Hz, 1H, NH) | +++ |
| 82 | 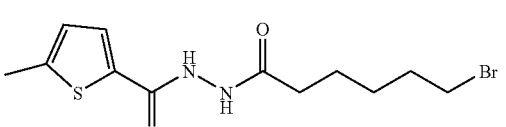 | A | 333[M + H]⁺ | δ(DMSO-$d_6$) = 1.41($m_c$, 2H, CH₂), 1.53($m_c$, 2H, CH₂), 1.79(quint., J= 7.2 Hz, 2H, CH₂), 2.16(t, J=7.2 Hz, 2H, CH₂), 2.46(s, 3H, CH₃), 3.52(t, J=6.9 Hz, 2H, CH₂), 6.85(dd, J=0.9, 4.8 Hz, 1H, H-4), 7.61(d, J=3.9 Hz, 1H, H-3), 9.77(s, 1H, NH), 10.16(s, 1H, NH) | +++ |
| 83 | 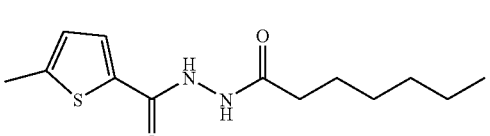 | A | 269[M + H]⁺ 267[M − H]⁻ | δ(DMSO-$d_6$) = 0.84(t, J=4.2 Hz, 3H, CH₃), 1.24($m_c$, 6H, (CH₂)₃), 1.48(quint., J=7.2 Hz, 2H, CH₂), 2.18(t, J=7.5 Hz, 2H, CH₂), 2.46(s, 3H, CH₃), 6.85(d, J=3.9 Hz, 1H, H-4), 7.60(d, J=3.3 Hz, 1H, H-3), 9.74(s, 1H, NH), 10.14(s, 1H, NH) | +++ |
| 84 | 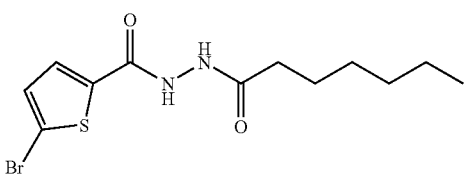 | A | 333[M + H]⁺ 331[M − H]⁻ | δ(CD₃OD) = 0.82(t, J=6.9 Hz, 3H, CH₃), 1.19-1.34(m, 6H, (CH₂)₃), 1.56(quint., J= 7.2 Hz, 2H, CH₂), 2.19(t, J=7.5 Hz, 2H, CH₂), 7.05(d, J=4.2 Hz, 1H, H-4), 7.43(d, J=4.2 Hz, 1H, H-3) | +++ |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 85 | (3-bromothiophene-2-carbonyl hydrazide with heptanoyl) | A | 347[M + H]$^+$ 345[M − H]$^-$ | δ(DMSO-d$_6$) = 0.89(t, J=6.9 Hz, 3H, CH$_3$), 1.30-1.37(m, 8H, (CH$_2$)$_4$), 1.57(quint., J=6.6 Hz, 2H, CH$_2$), 2.19(t, J=7.5 Hz, 2H, CH$_2$), 7.24(d, J=5.1 Hz, 1H, H-4), 7.87(d, J=5.1 Hz, 1H, H-5), 9.95-10.16(br.s, 2H, NH) | +++ |
| 86 | (thiophene-2-carbonyl hydrazide with (CH$_2$)$_{10}$—CH$_3$) | A | 325[M + H]$^+$ 323[M − H]$^-$ | δ(CD$_3$OD) = 0.80(t, J=6.9 Hz, 3H, CH$_3$), 1.14-1.32(m, 16H, (CH$_2$)$_8$), 1.57(quint., J=7.5 Hz, 2H, CH$_2$), 2.20(t, J=7.5 Hz, 2H, CH$_2$), 7.04(dd, J=3.9, 4.8 Hz, 1H, H-4), 7.60(dd, J=0.9, 4.8 Hz, 1H, H-3), 7.65(dd, J=1.2, 4.2 Hz, 1H, H-5) | +++ |
| 87 | (5-methylthiophene-2-carbonyl hydrazide with cyclopentylpropanoyl) | A | 281[M + H]$^+$ 279[M − H]$^-$ | δ(DMSO-d$_6$) = 1.06(m$_c$, 2H, CH$_2$), 1.50(m$_c$, 6H, (CH$_2$)$_3$), 1.72(m$_c$, 3H, CH and CH$_2$), 2.16(t, J=7.8 Hz, 2H, CH$_2$), 2.46(s, 3H, CH$_3$), 6.65(dd, J=0.9, 3.9 Hz, 1H, H-4), 7.61(d, J=3.6 Hz, 1H, H-3), 9.75(s, 1H, NH), 10.14(s, 1H, NH) | +++ |
| 88 | (5-methylthiophene-2-carbonyl hydrazide with methyl glutaryl) | A | 285[M + H]$^+$ 283[M − H]$^-$ | δ(CD$_3$OD) = 1.96(t, J=7.2 Hz, 2H, CH$_2$), 2.36(t, J=7.5 Hz, 2H, CH$_2$), 2.44(t, J=7.5 Hz, 2H, CH$_2$), 2.51(s, 3H, CH$_3$), 3.67(s, 3H, OCH$_3$), 6.82(d, J=3.9 Hz, 1H, H-4), 7.57(d, J=3.6 Hz, 1H, H-3) | + |
| 89 | (furan-2-carbonyl hydrazide with heptanoyl) | A | 239[M + H]$^+$ 237[M − H]$^-$ | δ(CD$_3$OD) = 1.11(t, J=6.6 Hz, 3H, CH$_3$), 1.47-1.63(m, 6H, (CH$_2$)$_3$), 1.86(quint., J=7.2 Hz, 2H, CH$_2$), 2.48(t, J=7.5 Hz, 2H, CH$_2$), 6.79(br.s, 1H, H-4), 7.39(d, J=3.6 Hz, 1H, H-3), 7.88(br.s, 1H, H-5) | +++ |
| 90 | (furan-2-carbonyl hydrazide with cyclopentylpropanoyl) | A | 251[M + H]$^+$ 249[M − H]$^-$ | δ(DMSO-d$_6$) = 1.14(m$_c$, 2H, CH$_2$), 1.60(m$_c$, 6H, (CH$_2$)$_3$), 1.80(m$_c$, 3H, CH and CH$_2$), 2.23(t, J=7.2 Hz, 2H, CH$_2$), 6.70(dd, J=1.8, 3.6 Hz, 1H, H-4), 7.62(d, J=3.6 Hz, 1H, H-3), 7.94(d, J=2.7 Hz, 1H, H-5), 9.82(s, 1H, NH), 10.19(s, 1H, NH) | +++ |
| 91 | (3,5-dimethylisoxazole-4-carbonyl hydrazide with octanoyl) | A | 282[M + H]$^+$ 280[M − H]$^-$ | δ(DMSO-d$_6$) = 0.75(t, J=6.9 Hz, 3H, CH$_3$), 1.15-1.23(m, 8H, (CH$_2$)$_4$), 1.43(quint., J=6.9 Hz, 2H, CH$_2$), 2.05(t, J=7.8 Hz, 2H, CH$_2$), 2.17(s, 3H, CH$_3$), 2.42(s, 3H, CH$_3$), 9.71(s, 1H, NH), 9.76(s, 1H, NH) | +++ |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 92 | (structure) | A | 373[M + H]$^+$ 371[M − H]$^-$ | δ(DMSO-d$_6$) = 0.65(t, J=6.6 Hz, 3H, CH$_3$), 0.97-1.12(m, 11H, NCH$_2$CH$_3$ and (CH$_2$)$_4$), 1.33(quint., J=6.9 Hz, 2H, CH$_2$), 1.92-1.97(m, 5H, CH$_3$-3 and CH$_2$), 3.98(q, J=7.5 Hz, 2H, NCH$_2$), 9.79(s, 1H, NH), 10.09(s, 1H, NH) | ++ |
| 93 | (structure) | A | 298[M + H]$^+$ 296[M − H]$^-$ | δ(DMSO-d$_6$) = 0.81(t, J=7.2 Hz, 3H, CH$_3$), 1.16-1.27(m, 8H, (CH$_2$)$_4$), 1.48(m$_c$, 2H, CH$_2$), 2.12(t, J=7.5 Hz, 2H, CH$_2$), 7.71(dd, J=1.5, 5.1 Hz, 1H, H-5), 7.80(br.s, 1H, H-3), 8.54(d, J=5.1 Hz, 1H, H-6), 9.94(s, 1H, NH), 10.62(s, 1H, NH) | +++ |
| 94 | (structure) | A | 298[M + H]$^+$ 296[M − H]$^-$ | δ(DMSO-d$_6$) = 0.94(t, J=7.2 Hz, 3H, CH$_3$), 1.34-1.39(m, 8H, (CH$_2$)$_4$), 1.62(quint., J=6.9 Hz, 2H, CH$_2$), 2.25(t, J=7.2 Hz, 2H, CH$_2$), 7.61(dd, J=5.1, 7.8 Hz, 1H, H-5), 7.98(dd, J=1.8, 7.5 Hz, 1H, H-4), 8.59(dd, J=1.8, 4.5 Hz, 1H, H-6), 10.12(s, 1H, NH), 10.47(s, 1H, NH) | +++ |
| 95 | (structure) | A | 335[M + H]$^+$ 333[M − H]$^-$ | δ(DMSO-d$_6$) = 0.96(t, J=7.2 Hz, 3H, CH$_3$), 3.09(s, 2H, CH$_2$), 3.86(q, J=7.2 Hz, 2H, OCH$_2$), 6.97(d, J=5.4 Hz, 1H, H-4), 7.60(d, J=5.1 Hz, 1H, H-5), 10.05(s, 2H, NH) | +++ |
| 96 | (structure) | A | 307[M + H]$^+$ 305[M − H]$^-$ | δ(DMSO-d$_6$) = 1.33(t, J=7.2 Hz, 3H, CH$_3$), 3.49(s, 2H, CH$_2$), 4.24(q, J=7.2 Hz, 2H, OCH$_2$), 7.55-7.64(m, 2H, CH$_{ar}$), 8.10(d, J=6.8 Hz, 1H, CH$_{ar}$), 8.17(d, J=6.9 Hz, 1H, CH$_{ar}$), 8.30(s, 1H, H-3), 10.39(s, 1H, NH), 10.92(s, 1H, NH) | ++ |
| 97 | (structure) | A | 323[M + H]$^+$ 321[M − H]$^-$ | δ(CD$_3$OD) = 6.92(d, J=4.2 Hz, 1H, CH$_{ar}$), 7.03(d, J=4.5 Hz, 1H, CH$_{ar}$), 7.37(d, J=3.9 Hz, 1H, CH$_{ar}$), 7.60(d, J=4.5 Hz, 2H, CH$_{ar}$) | +++ |
| 98 | (structure) | A | 283[M + H]$^+$ 281[M − H]$^-$ | δ(CD$_3$OD) = 0.78(t, J=7.5 Hz, 3H, CH$_3$), 1.44(sext., J=7.5 Hz, 2H, CH$_2$), 1.98(t, J=7.5 Hz, 2H, CH$_2$), 6.96(d, J=3.9 Hz, 1H, H-4), 7.37(d, J=4.2 Hz, 1H, H-3) | ++ |
| 99 | (structure) | A | 325[M + H]$^+$ 323[M − H]$^-$ | δ(CD$_3$OD) = 0.80(t, J=6.9 Hz, 3H, CH$_3$), 1.12-1.25(m, 6H, (CH$_2$)$_3$), 1.40(quint, J=7.2 Hz, 2H, CH$_2$), 2.02(t, J=7.5 Hz, 2H, CH$_2$), 6.96(d, J=4.2 Hz, 1H, H-4), 7.37(d, J=4.2 Hz, 1H, H-3) | + |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 100 | (thiophene-2-carbonyl-thiosemicarbazide N-butyl) | F | 258[M + H]$^+$ 256[M − H]$^−$ | δ(CD$_3$OD) = 0.82(t, J=7.5 Hz, 3H, CH$_3$), 1.25(sext, J=7.5 Hz, 2H, CH$_2$), 1.48(quint., J=7.5 Hz, 2H, CH$_2$), 3.45(t, J=7.2 Hz, 2H, CH$_2$), 7.06(dd, J=3.9, 3.9 Hz, 1H, H-4), 7.63(dd, J=1.2, 4.8 Hz, 1H, H-3), 7.69(d, J=3.6 Hz, 1H, H-5) | +++ |
| 101 | (4,5-dibromothiophene-2-carbonyl-semicarbazide N-pentyl) | F | 412[M + H]$^+$ 410[M − H]$^−$ | δ(DMSO-d$_6$) = 1.04(t, J=7.2 Hz, 3H, CH$_3$), 1.33-1.61(m, 6H, CH$_2$), 3.17(q, J=6.3 Hz, 2H, CH$_2$), 6.71(s, 1H, H-3), 7.97(s, 1H, NH), 8.08(s, 1H, NH), 10.44(s, 1H, NH) | + |
| 102 | (5-bromothiophene semicarbazide 4-F-2-CF$_3$-phenyl) | F | 426[M + H]$^+$ 424[M − H]$^−$ | δ(DMSO-d$_6$) = 7.32(d, J=3.9 Hz, 1H, H-4), 7.49-7.59(m, 2H, H-5' and H-6'), 7.66(d, J=4.2 Hz, 1H, H-3), 8.21(s, 1H, NH), 8.73(s, 1H, NH), 10.47(s, 1H, NH) | + |
| 103 | (4,5-dibromothiophene semicarbazide 4-Cl-3-CF$_3$-phenyl) | F | 520[M + H]$^+$ 518[M − H]$^−$ | δ(DMSO-d$_6$) = 7.65(d, J=8.7 Hz, 1H, CH$_{ar}$), 7.85(d, J=8.7 Hz, 1H, CH$_{ar}$), 7.89(s, 1H, CH$_{ar}$), 8.13(s, 1H, H-3), 8.71(s, 1H, NH), 9.43(s, 1H, NH), 10.61(s, 1H, NH) | ++ |
| 104 | (4,5-dibromothiophene semicarbazide 3-CF$_3$-phenyl) | F | 486[M + H]$^+$ 484[M − H]$^−$ | δ(DMSO-d$_6$) = 7.47(d, J=7.8 Hz, 1H, CH$_{ar}$), 7.59(t, J=7.8 Hz, 1H, CH$_{ar}$), 7.82(d, J=7.8 Hz, 1H, CH$_{ar}$), 7.85(s, 1H, NH), 7.98-8.00(br.s, 2H, CH$_{ar}$ and NH), 8.01(s, 1H, H-3), 10.58(s, 1H, NH) | +++ |
| 105 | (3-Cl-4-methylthiophene semicarbazide 4-SMe-phenyl) | F | 356[M + H]$^+$ 354[M − H]$^−$ | δ(DMSO-d$_6$) = 2.28(s, 3H, CH$_3$), 2.52(s, 3H, SCH$_3$), 7.29(d, J=8.7 Hz, 2H, CH$_{ar}$), 7.52(d, J=8.7 Hz, 2H, CH$_{ar}$), 7.69(s, 1H, H-5), 8.37(s, 1H, NH), 8.94(s, 1H, NH), 9.96(s, 1H, NH) | +++ |
| 106 | (3-Cl-4-methylthiophene semicarbazide 4-Br-phenyl) | F | 388[M + H]$^+$ 386[M − H]$^−$ | δ(DMSO-d$_6$) = 2.24(s, 3H, CH$_3$), 7.48-7.53(m, 4H, CH$_{ar}$), 7.62(s, 1H, H-5), 8.54(s, 1H, NH), 9.19(s, 1H, NH), 9.97(s, 1H, NH) | +++ |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 107 | | F | 388[M + H]$^+$ 386[M − H]$^−$ | δ(DMSO-d$_6$) = 4.77(s, 2H, CH$_2$), 7.08(t, J=7.5 Hz, 1H, CH$_{ar}$), 7.29(d, J=7.5 Hz, 1H, CH$_{ar}$), 7.33(d, J=3.9 Hz, 1H, H-4), 7.42(d, J=7.5 Hz, 1H, CH$_{ar}$), 7.65-7.70(m, 2H, H-3 and CH$_{ar}$), 8.31(s, 1H, NH), 8.61 (s, 1H, NH), 10.48(s, 1H, NH) | +++ |
| 108 | | F | 344[M + H]$^+$ 342[M − H]$^−$ | δ(DMSO-d$_6$) = 4.82(s, 2H, CH$_2$), 7.13(t, J=6.9 Hz, 1H, CH$_{ar}$), 7.28(d, J=4.2 Hz, 1H, H-4), 7.36(d, J=7.5 Hz, 1H, CH$_{ar}$), 7.46(d, J=7.5 Hz, 1H, CH$_{ar}$), 7.71(d, J=8.4 Hz, 1H, CH$_{ar}$), 7.79(d, J=3.9 Hz, 1H, H-3), 8.38(s, 1H, NH), 8.68(s, 1H, NH), 10.55(s, 1H, NH) | +++ |
| 109 | | F | 370[M + H]$^+$ 368[M − H]$^−$ | δ(DMSO-d$_6$) = 3.55(s, 3H, OCH$_3$), 6.69(d, J=7.5 Hz, 2H, CH$_{ar}$), 7.17-7.24(m, 3H, CH$_{ar}$), 7.53(br.s, 1H, CH$_{ar}$), 7.97(s, 1H, NH), 8.53(s, 1H, NH), 10.19(s, 1H, NH) | + |
| 110 | | F | 376[M + H]$^+$ 374[M − H]$^−$ | δ(DMSO-d$_6$) = 7.15-7.20(m, 2H, CH$_{ar}$), 7.33-7.41(m, 2H, CH$_{ar}$), 7.69(br.s, 1H, CH$_{ar}$), 8.47(s, 1H, NH), 8.59(s, 1H, NH), 10.52(s, 1H, NH) | + |
| 111 | | F | 415[M + H]$^+$ 413[M − H]$^−$ | δ(DMSO-d$_6$) = 7.71-7.75(m, 4H, CH$_{ar}$), 8.02(t, J=4.2 Hz, 1H, CH$_{ar}$), 8.24(t, J=5.1 Hz, 1H, CH$_{ar}$), 9.23(br.s, 1H, NH), 9.97(br.s, 1H, NH), 10.46(br.s, 1H, NH) | + |
| 112 | | F | 360[M + H]$^+$ 358[M − H]$^−$ | δ(DMSO-d$_6$) = 2.19(s, 3H, CH$_3$), 6.88(t, J=8.7 Hz, 1H, CH$_{ar}$), 7.05-7.13(m, 2H, CH$_{ar}$), 7.49-7.54(m, 2H, CH$_{ar}$), 7.72(d, J=6.3 Hz, 1H, CH$_{ar}$), 7.82(d, J=6.3 Hz, 1H, CH$_{ar}$), 8.03(d, J=6.9 Hz, 1H, CH$_{ar}$), 8.10(s, 1H, NH), 8.50(s, 1H, NH), 10.26(s, 1H, NH) | + |
| 113 | | H | 238[M + H]$^+$ 236[M − H]$^−$ | δ(CDCl$_3$) = 0.86(ψ-t, J≈7 Hz, 1H, 9-H), 1.21-1.38(m, 6H, 6-H, 7-H, 8-H), 1.59(ψ-quint, J=7.3 Hz, 2H, 5-H), 2.63(t, J=7.4 Hz, 2H, 4-H), 3.60(s, 2H, 2-H), 6.61(s, br., 1H, ring-H), 7.46(s, br., 1H, ring-H), 10.61(s, br., 1H, NH). | + |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 114 | | H | 252[M + H]$^+$ 250[M − H]$^-$ | δ(CDCl$_3$) = 0.89(ψ-t, J≈7 Hz, 1H, 9-H), 1.23-1.37(m, 6H, 6-H, 7-H, 8-H), 1.63(ψ-quint, J=7.3 Hz, 2H, 5-H), 2.58(t, J=7.3 Hz, 2H, 4-H), 3.66(s, 2H, 2-H), 3.87(s, 2H, NCH$_3$), 6.44(d, J=2.1 Hz, 1H, ring-H), 7.47(d, J=2.1 Hz, 1H, ring-H), 9.85(s, br., 1H, NH). | + |
| 115 | | H | 294[M + H]$^+$ 292[M − H]$^-$ | δ(CDCl$_3$) = 0.87(ψ-t, J≈7 Hz, 1H, 12-H), 1.19-1.37(m, 12H, 6-H, 7-H, 8-H, 9-H, 10-H, 11-H), 1.61(ψ-quint, J=7.3 Hz, 2H, 5-H), 2.53(t, J=7.3 Hz, 2H, 4-H), 3.57(s, 2H, 2-H), 3.75(s, 2H, NCH$_3$), 6.30(d, J=1.8 Hz, 1H, ring-H), 7.38(d, J=1.8 Hz, 1H, ring-H), 9.55(s, br., 1H, NH). | + |
| 116 | | H | 266[M + H]$^+$ 264[M − H]$^-$ | δ(CDCl$_3$) = 0.89(ψ-t, J≈7 Hz, 1H, 9-H), 1.24-1.36(m, 6H, 6-H, 7-H, 8-H), 1.46(t, J=7.2 Hz, 3H, NCH$_2$CH$_3$), 1.63(ψ-quint, J=7.3 Hz, 2H, 5-H), 2.58(t, J=7.3 Hz, 2H, 4-H), 3.66(s, 2H, 2-H), 4.21(q, J=7.3 Hz, 2H, NCH$_2$CH$_3$), 6.46(d, J=2.1 Hz, 1H, ring-H), 7.49(d, J=2.1 Hz, 1H, ring-H), 9.85(s, br., 1H, NH). | + |
| 117 | | H | 308[M + H]$^+$ 306[M − H]$^-$ | δ(CDCl$_3$) = 0.88(ψ-t, J≈7 Hz, 1H, 12-H), 1.22-1.37(m, 12H, 6-H, 7-H, 8-H, 9-H, 10-H, 11-H), 1.46(t, J=7.3 Hz, 3H, NCH$_2$CH$_3$), 1.64(ψ-quint, J=7.3 Hz, 2H, 5-H), 2.58(t, J=7.3 Hz, 2H, 4-H), 3.61(s, 2H, 2-H), 4.10(q, J=7.3 Hz, 2H, NCH$_2$CH$_3$), 6.37(d, J=1.8 Hz, 1H, ring-H), 7.43(d, J=1.8 Hz, 1H, ring-H), 9.56(s, br., 1H, NH). | + |
| 118 | | H | 266[M + H]$^+$ 264[M − H]$^-$ | δ(CDCl$_3$) = 0.88(ψ-t, J≈7 Hz, 1H, 9-H), 1.23-1.36(m, 6H, 6-H, 7-H, 8-H), 1.61(ψ-quint, J=7.3 Hz, 2H, 5-H), 2.22(s, 3H, ring-CH$_3$), 2.57(t, J=7.3 Hz, 2H, 4-H), 3.60(s, 2H, 2-H), 3.72(s, 3H, NCH$_3$), 6.15(s, 1H, ring-H), 9.58(s, br., 1H, NH). | + |
| 119 | | H | 308[M + H]$^+$ 306[M − H]$^-$ | δ(CDCl$_3$) = 0.88(ψ-t, J≈7 Hz, 1H, 12-H), 1.21-1.36(m, 12H, 6-H, 7-H, 8-H, 9-H, 10-H, 11-H), 1.63(ψ-quint, J=7.3 Hz, 2H, 5-H), 2.22(s, 3H, ring-CH$_3$), 2.57(t, J=7.3 Hz, 2H, 4-H), 3.60(s, 2H, 2-H), 3.72(s, 3H, NCH$_3$), 6.14(s, 1H, ring-H), 9.44(s, br., 1H, NH). | + |

TABLE 2-continued

Structure and biosensor assay results of the tested compounds.

| # | Compound | Synthesis method/ supplier | HPLC/ MS (ESI) | ¹H-NMR (300 MHz) | IC₅₀* |
|---|---|---|---|---|---|
| 120 | 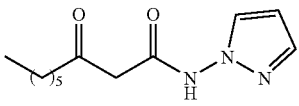 | H | 238[M + H]⁺ 236[M − H]⁻ | δ(CDCl₃) = 0.88(ψ-t, J≈7 Hz, 1H, 9-H), 1.17-1.34(m, 6H, 6-H, 7-H, 8-H), 1.59(ψ-quint, J=7.3 Hz, 2H, 5-H), 2.56(t, J=7.3 Hz, 2H, 4-H), 3.59(s, 2H, 2-H), 6.31(ψ-t, J=2.3 Hz, 1H, ring-H), 7.44(dd, J=2.3 Hz, J=0.6 Hz, 1H, ring-H), 7.49(d, J≈2 Hz, 1H, ring-H), 10.64(s, br., 1H, NH). | + |
| 121 | 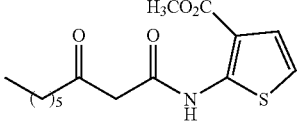 | H | 312[M + H]⁺ 310[M − H]⁻ | δ(CDCl₃) = 0.88(ψ-t, J≈7 Hz, 1H, 9-H), 1.21-1.36(m, 6H, 6-H, 7-H, 8-H), 1.65(ψ-quint, J=7.3 Hz, 2H, 5-H), 2.59(t, J=7.3 Hz, 2H, 4-H), 3.66(s, 2H, 2-H), 3.94(s, 3H, CO₂CH₃), 6.75(dd, J=5.8 Hz, J=0.8 Hz, 1H, ring-H), 7.23(d, J=5.8 Hz, 1H, ring-H), 11.88(s, br., 1H, NH) | + |
| 122 | 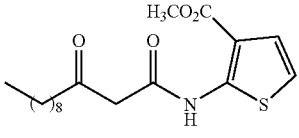 | H | 354[M + H]⁺ 352[M − H]⁻ | δ(CDCl₃) = 0.88(ψ-t, J≈7 Hz, 1H, 12-H), 1.21-1.36(m, 12H, 6-H, 7-H, 8-H, 9-H, 10-H, 11-H), 1.65(ψ-quint, J=7.3 Hz, 2H, 5-H), 2.58(t, J=7.3 Hz, 2H, 4-H), 3.66(s, 2H, 2-H), 3.93(s, 3H, CO₂CH₃), 6.74(dd, J=5.8 Hz, J=0.8 Hz, 1H, ring-H), 7.22(d, J=5.8 Hz, 1H, ring-H), 11.88(s, br., 1H, NH). | + |
| 123 | 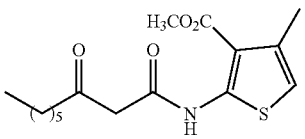 | H | 340[M + H]⁺ 338[M − H]⁻ | δ(CDCl₃) = 0.88(ψ-t, J≈7 Hz, 1H, 9-H), 1.24-1.35(m, 6H, 6-H, 7-H, 8-H), 1.41(t, J=7.1 Hz, 3H, CO₂CH₂CH₃), 1.63(ψ-quint, J=7.4 Hz, 2H, 5-H), 2.38(d, J=1.1 Hz, 3H, ring-CH₃, 2.58(t, J=7.3 Hz, 2H, 4-H), 3.63(s, 2H, 2-H), 4.42(q, J=7.1 Hz, 2H, CO₂CH₂CH₃), 6.39-6.41(m, 1H, ring-H), 11.97(s, br., 1H, NH). | + |
| 124 | 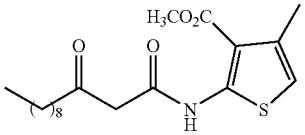 | H | 382[M + H]⁺ 380[M − H]⁻ | δ(CDCl₃) = 0.88(ψ-t, J≈7 Hz, 1H, 12-H), 1.21-1.36(m, 12H, 6-H, 7-H, 8-H, 9-H, 10-H, 11-H), 1.41(t, J=7.1 Hz, 3H, CO₂CH₂CH₃), 1.63(ψ-quint, J=7.4 Hz, 2H, 5-H), 2.38(d, J=1.1 Hz, 3H, ring-CH₃), 2.58(t, J=7.3 Hz, 2H, 4-H), 3.63(s, 2H, 2-H), 4.42(q, J=7.1 Hz, 2H, CO₂CH₂CH₃), 6.39-6.41(m, 1H, ring-H), 11.97(s, br., 1H, NH). | + |
| 125 | 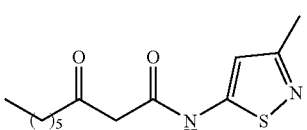 | H | 269[M + H]⁺ 267[M − H]⁻ | δ(CDCl₃) = 0.88(ψ-t, J≈7 Hz, 1H, 9-H), 1.23-1.37(m, 6H, 6-H, 7-H, 8-H), 1.61(ψ-quint, J=7.3 Hz, 2H, 5-H), 2.55(s, 3H, ring-CH₃), 2.60(t, J=7.3 Hz, 2H, 4-H), 3.84(s, 2H, 2-H), 6.91(s, 1H, ring-H). | + |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 126 | | H | 311[M + H]$^+$ 309[M − H]$^−$ | δ(CDCl$_3$) = 0.88(ψ-t, J≈7 Hz, 1H, 12-H), 1.22-1.37(m, 12H, 6-H, 7-H, 8-H, 9-H, 10-H, 11-H), 1.63(ψ-quint, J=7.3 Hz, 2H, 5-H), 2.42(s, 3H, ring-CH$_3$), 2.58(t, J=7.3 Hz, 2H, 4-H), 3.66(s, 2H, 2-H), 6.66(s, 1H, ring-H), 10.51(s, br., 1H, NH). | + |
| 127 | | H | 255[M + H]$^+$ 253[M − H]$^−$ | δ(CDCl$_3$) = 0.88(ψ-t, J≈7 Hz, 1H, 9-H), 1.24-1.37(m, 6H, 6-H, 7-H, 8-H), 1.62(ψ-quint, J=7.3 Hz, 2H, 5-H), 2.59(t, J=7.3 Hz, 2H, 4-H), 3.71(s, 2H, 2-H), 7.00(d, J=3.7 Hz, 1H, ring-H), 7.47(d, J=3.7 Hz, 1H, ring-H), [NH proton not visible]. | + |
| 128 | | H | 297[M + H]$^+$ 295[M − H]$^−$ | δ(CDCl$_3$) = 0.88(ψ-t, J≈7 Hz, 1H, 12-H), 1.21-1.37(m, 12H, 6-H, 7-H, 8-H, 9-H, 10-H, 11-H), 1.62(ψ-quint, J=7.3 Hz, 2H, 5-H), 2.61(t, J=7.3 Hz, 2H, 4-H), 3.66(s, 2H, 2-H), 7.00(d, J=3.6 Hz, 1H, ring-H), 7.49(d, J=3.6 Hz, 1H, ring-H), 11.54(s, br., 1H, NH). | + |
| 129 | | H | 343[M + H]$^+$ 341[M − H]$^−$ | δ(CDCl$_3$) = 0.85(ψ-t, J≈7 Hz, 1H, 9-H), 1.21-1.37(m, 6H, 6-H, 7-H, 8-H), 1.59(ψ-quint, J=7.3 Hz, 2H, 5-H), 2.38(s, 3H, SCH$_3$*), 2.56(t, J=7.3 Hz, 2H, 4-H), 2.68(s, 3H, COCH$_3$*), 3.87(s, br., 2H, 2-H), 10.88(s, br., 1H, NH). | + |
| 130 | | H | 239[M + H]$^+$ 237[M − H]$^−$ | δ(CDCl$_3$) = 0.89(ψ-t, J≈7 Hz, 1H, 9-H), 1.23-1.36(m, 6H, 6-H, 7-H, 8-H), 1.62(ψ-quint, J=7.3 Hz, 2H, 5-H), 2.57(t, J=7.3 Hz, 2H, 4-H), 3.60(s, 2H, 2-H), 7.01(d, J=1.7 Hz, 1H, ring-H), 8.28(dd, J=1.7 Hz, J=0.5 Hz, 1H, ring-H), 9.90(s, br., 1H, NH). | + |
| 131 | | H | 281[M + H]$^+$ 279[M − H]$^−$ | δ(CDCl$_3$) = 0.88(ψ-t, J≈7 Hz, 1H, 12-H), 1.22-1.36(m, 12H, 6-H, 7-H, 8-H, 9-H, 10-H, 11-H), 1.62(t-quint, J=7.3 Hz, 2H, 5-H), 2.57(t, J=7.3 Hz, 2H, 4-H), 3.60(s, 2H, 2-H), 7.00(d, J=1.7 Hz, 1H, ring-H), 8.28(dd, J=1.7 Hz, J=0.5 Hz, 1H, ring-H), 9.88(s, br., 1H, NH). | + |
| 132 | | H | 253[M + H]$^+$ 251[M − H]$^−$ | δ(CDCl$_3$) = 0.89(ψ-t, J≈7 Hz, 1H, 9-H), 1.25-1.37(m, 6H, 6-H, 7-H, 8-H), 1.63(ψ-quint, J=7.3 Hz, 2H, 5-H), 2.27(s, 3H, ring-CH$_3$), 2.56(t, J=7.3 Hz, 2H, 4-H), 3.60(s, 2H, 2-H), 6.20(s, 1H, ring-H), 10.17(s, br., 1H, NH). | + |

TABLE 2-continued

Structure and biosensor assay results of the tested compounds.

| # | Compound | Synthesis method/ supplier | HPLC/ MS (ESI) | $^1$H-NMR (300 MHz) | IC$_{50}$* |
|---|---|---|---|---|---|
| 133 | [structure: CH$_3$-(CH$_2$)$_8$-C(O)-CH$_2$-C(O)-NH-(3-methylisoxazol-5-yl)] | H | 295[M + H]$^+$<br>293[M − H]$^−$ | δ(CDCl$_3$) =<br>0.88(ψ-t, J≈7 Hz, 1H, 12-H),<br>1.20-1.37(m, 12H, 6-H, 7-H, 8-H, 9-H, 10-H, 11-H),<br>1.63(ψ-quint, J=7.3 Hz, 2H, 5-H),<br>2.26(s, 3H, ring-CH$_3$),<br>2.56(t, J=7.3 Hz, 2H, 4-H),<br>3.60(s, 2H, 2-H),<br>6.20(s, 1H, ring-H),<br>10.16(s, br., 1H, NH). | + |
| 134 | [structure: CH$_3$-(CH$_2$)$_5$-C(O)-CH$_2$-C(O)-NH-(4-methyloxazol-2-yl)] | H | 253[M + H]$^+$<br>251[M − H]$^−$ | δ(CDCl$_3$) =<br>0.88(ψ-t, J≈7 Hz, 1H, 9-H),<br>1.25-1.38(m, 6H, 6-H, 7-H, 8-H),<br>1.61(ψ-quint, J=7.3 Hz, 2H, 5-H),<br>2.12(d, J=1.3 Hz, 1H, ring-CH$_3$),<br>2.57(t, J=7.3 Hz, 2H, 4-H),<br>3.68(s, br., 2H, 2-H),<br>7.12(q, J=1.3 Hz, 1H, ring-H),<br>[NH proton not visible]. | + |
| 135 | [structure: CH$_3$-(CH$_2$)$_5$-C(O)-CH$_2$-C(O)-NH-(4-cyano-2-methyloxazol-5-yl)] | H | 278[M + H]$^+$<br>276[M − H]$^−$ | δ(CDCl$_3$) =<br>0.87(ψ-t, J≈7 Hz, 1H, 9-H),<br>1.21-1.37(m, 6H, 6-H, 7-H, 8-H),<br>1.59(ψ-quint, J=7.3 Hz, 2H, 5-H),<br>2.41(s, 3H, ring-CH$_3$),<br>2.57(t, J=7.3 Hz, 2H, 4-H),<br>3.65(s, 2H, 2-H),<br>10.10(s, br., 1H, NH). | ++ |
| 136 | [structure: CH$_3$-(CH$_2$)$_5$-C(O)-CH$_2$-C(O)-NH-(3-cyano-4,5-dimethylfuran-2-yl)] | H | 291[M + H]$^+$<br>289[M − H]$^−$ | δ(CDCl$_3$) =<br>0.85(ψ-t, J≈7 Hz, 1H, 9-H),<br>1.21-1.34(m, 6H, 6-H, 7-H, 8-H),<br>1.57(ψ-quint, J=7.3 Hz, 2H, 5-H),<br>1.97(q, J=0.8 Hz, 3H, ring-CH$_3$),<br>2.13(q, J=0.9 Hz, 3H, ring-CH$_3$),<br>2.55(t, J=7.4 Hz, 2H, 4-H),<br>3.60(s, 2H, 2-H),<br>9.81(s, br., 1H, NH). | + |
| 137 | [structure: CH$_3$-(CH$_2$)$_8$-C(O)-CH$_2$-C(O)-NH-(3-cyano-4,5-dimethylfuran-2-yl)] | H | 333[M + H]$^+$<br>331[M − H]$^−$ | 0.88(ψ-t, J≈7 Hz, 1H, 12-H),<br>1.21-1.37(m, 12H, 6-H, 7-H, 8-H, 9-H, 10-H, 11-H),<br>1.62(ψ-quint, J=7.3 Hz, 2H, 5-H),<br>2.01(q, J=0.9 Hz, 3H, ring-CH$_3$),<br>2.17(q, J=0.9 Hz, 3H, ring-CH$_3$),<br>2.57(t, J=7.4 Hz, 2H, 4-H),<br>3.60(s, 2H, 2-H),<br>9.78(s, br., 1H, NH). | + |
| 138 | [structure: CH$_3$-(CH$_2$)$_5$-C(O)-CH$_2$-C(O)-NH-(5-methoxycarbonylfuran-2-yl)] | H | 296[M + H]$^+$<br>294[M − H]$^−$ | δ(CDCl$_3$) =<br>0.84(ψ-t, J≈7 Hz, 1H, 9-H),<br>1.17-1.35(m, 6H, 6-H, 7-H, 8-H),<br>1.57(ψ-quint, J=7.3 Hz, 2H, 5-H),<br>2.55(t, J=7.3 Hz, 2H, 4-H),<br>3.63(s, 2H, 2-H),<br>3.83(s, 3H, CO$_2$CH$_3$),<br>6.47(d, J=3.6 Hz, 1H, ring-H),<br>7.14(d, J=3.6 Hz, 1H, ring-H),<br>10.15(s, br., 1H, NH). | + |

*+++: 1-50 μM; ++: 50-100 μM; +: >100 μM; — not determined

2. Biosensor Assay

Quorum sensing inhibition of the compounds was investigated with the aid of the bioluminescent sensor strain *Escherichia coli* MT102 (pSB403) (Winson et at., *FEMS Microbiol. Lett.* 163:185-92, 1998). Plasmid pSB403 contains the *Photobacterium fischeri* luxR gene together with the tuxI promoter region as a transcriptional fusion to the bioluminescence genes luxCDABE of Photorhabdus luminescence. Although *E. coli* pSB403 exhibits the highest sensitivity for the *Photobacterium fischeri* quorum sensing signal N-(3-oxohexanoyl)homoserine lactone (3-oxo-C6-HSL), a wide range of other HSL molecules are detected by the sensor (Winson et al., *FEMS Microbiol. Lett.* 163:185-92, 1998; Geisenberger et al, *FEMS Microbiol. Lett.* 184: 273-8, 2000).

Inhibitory studies were conducted in a microtitre dish assay as follows: the *E. coli* sensor strain grown over night in LB medium (Sambrook et al., Molecular Cloning: A Laboratory Maual. 2$^{nd}$ Edn. Cold Spring Harbor Laboratory, New York, 1989) was diluted 1:4 and grown for another 1 hour at 30° C. After addition of 3oxo-C6-HSL (final concentration 100 nM) 100 µl of an exponential culture suspension were filled in the wells of a FluoroNunc Polysorp microtitre dish. The test compounds were added to the culture in different concentrations and bioluminescence was measured after 4 hours of incubation at 30° C. with a Lamda Fluoro 320 Plus reader (Bio-Tek Instruments). Inhibitor-mediated reduction of light emission was correlated with the value obtained without addition of the test compounds. $IC_{50}$ values (concentration of inhibitor required for 50% inhibition of the signal compared to the signal without inhibitor) were determined by using a fitting function after drawing a graph of the activities of eight different inhibitor concentrations. The determined $IC_{50}$ range of each compound is listed in Table 2.

Figure 2:
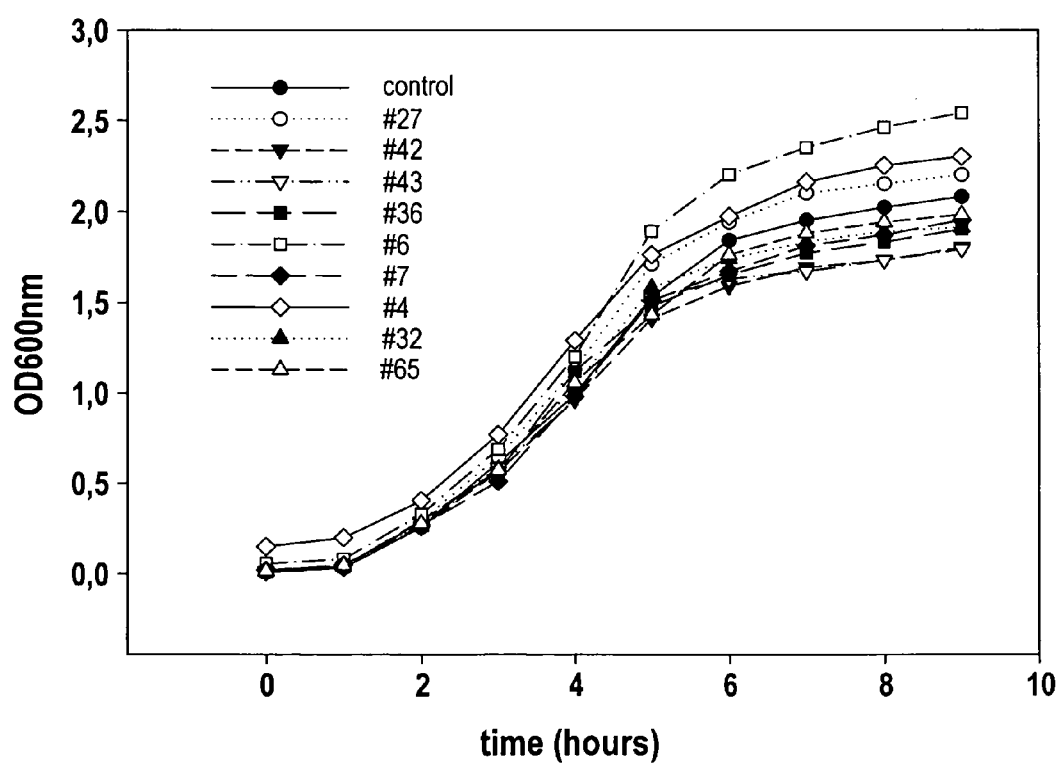
FIG. 2 illustrates the influence of representative compounds of the growth of *E. coli* MT102 (pSB403).

To exclude the possibility that the inhibitory effect is attributed to growth inhibition but not to a specific interaction of the test compound with the sensors quorum sensing system growth curves in the presence and absence of the test compounds were compared. *E. coli* MT102 (pSB403) was grown in LB medium at 37° C. in the presence of 0.4 mM test compound. Growth was measured as optical density at 600 nm. None of the compounds listed in Table 2 exhibit any growth inhibitory effects on the sensor strain *E. coli* MT102 (pSB403). FIG. 2 shows the growth curves of representative compounds indicating a specific inhibitory effect of the compounds on the quorum sensing system.

3. Inhibition of Protease Production

Figure 3:
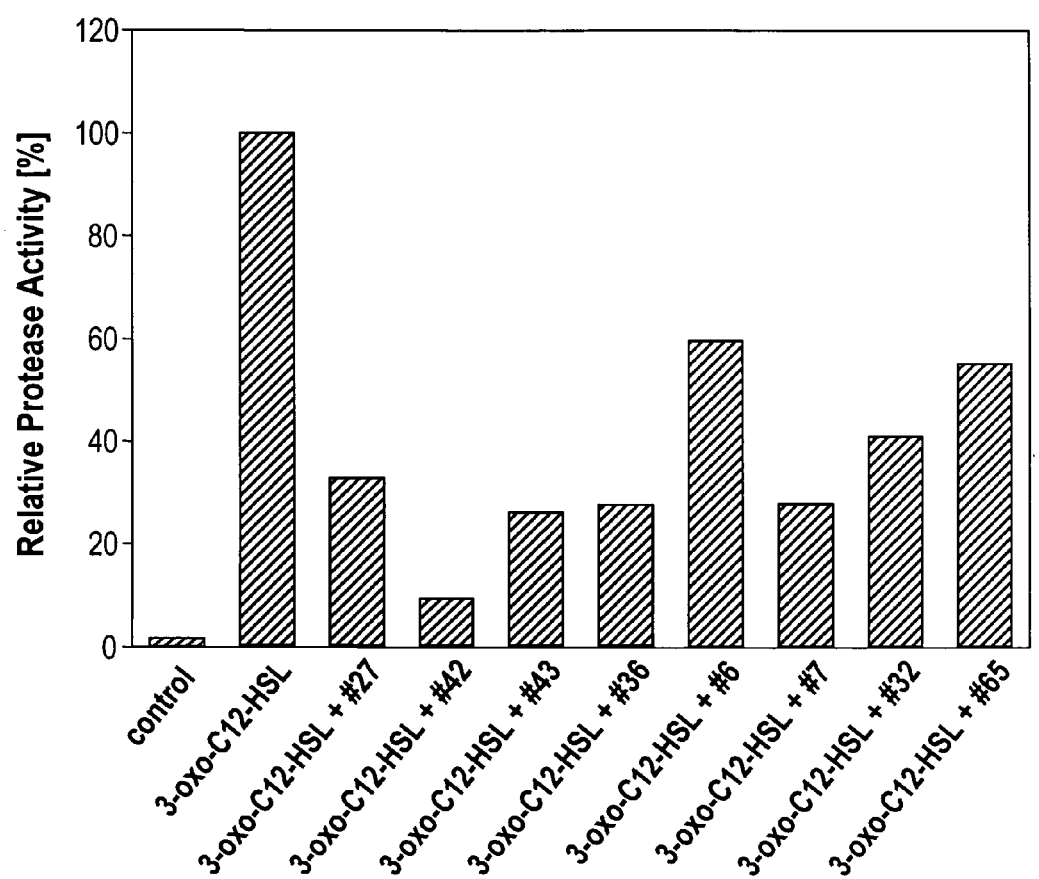
FIG. 3 illustrates the inhibitory effect of several compounds on the protease production of *P. aeruginosa* PAO1-JP2.

The inhibitory effect of the compounds on quorum sensing regulated virulence factors was demonstrated by investigating the expression of extracellular proteases by *Pseudomonas aeruginosa*. The *P. aeruginosa* mutant strain PAO-JP2 (Pearson et al., *J. Bacteriol*. 179:5756-67, 1997) carrying mutations in the quorum sensing genes lasI and rhlI is unable to produce extracellular proteolytic enzymes. Protease expression can be completely restored by external addition of 3-oxo-C12-HSL. The protease assay was performed according to Riedel et at. (*J. Bacteriol*. 183:1805-9, 2001) with few modifications. PAO-JP2 was grown in LB medium at 30° C. and shaking at 250 rpm to an OD600 nm of 0.5. The test compounds were added at a final concentration of 0.4 mM and the culture was incubated for further 30 min at 30° C. and shaking at 250 rpm. After addition of 3-oxo-C12-HSL at a final concentration of 0.3 µM the cultures were grown for an additional 6 hours at 30° C. and shaking at 250 rpm. The proteolytic activity was measured as described by Ayora & Götz (*Mol. Gen. Genet*. 242:421-30, 1994). 50 µl culture supernatant were incubated with Azocasein (250 µl 2%, Sigma, St Louis, Mo.) for 1 hour at 37° C. After precipitation of undigested substrate with trichloroacetic acid (1.2 ml 10%) for 20 minutes at room temperature, followed by 5 minutes centrifugation at 13000 rpm, NaOH (0.75 ml 1M) was added to the supernatant. The relative protease activity was measured as absorbance at 440 nm ($OD_{440nm}$) of the supernatant divided by the optical density of the culture ($OD_{600nm}$). FIG. 3 demonstrates the inhibitory effect of several compounds on protease production of *P. aeruginosa* PAO-JP2. The data presented are representative for at least three separate experiments.

Figure 4:
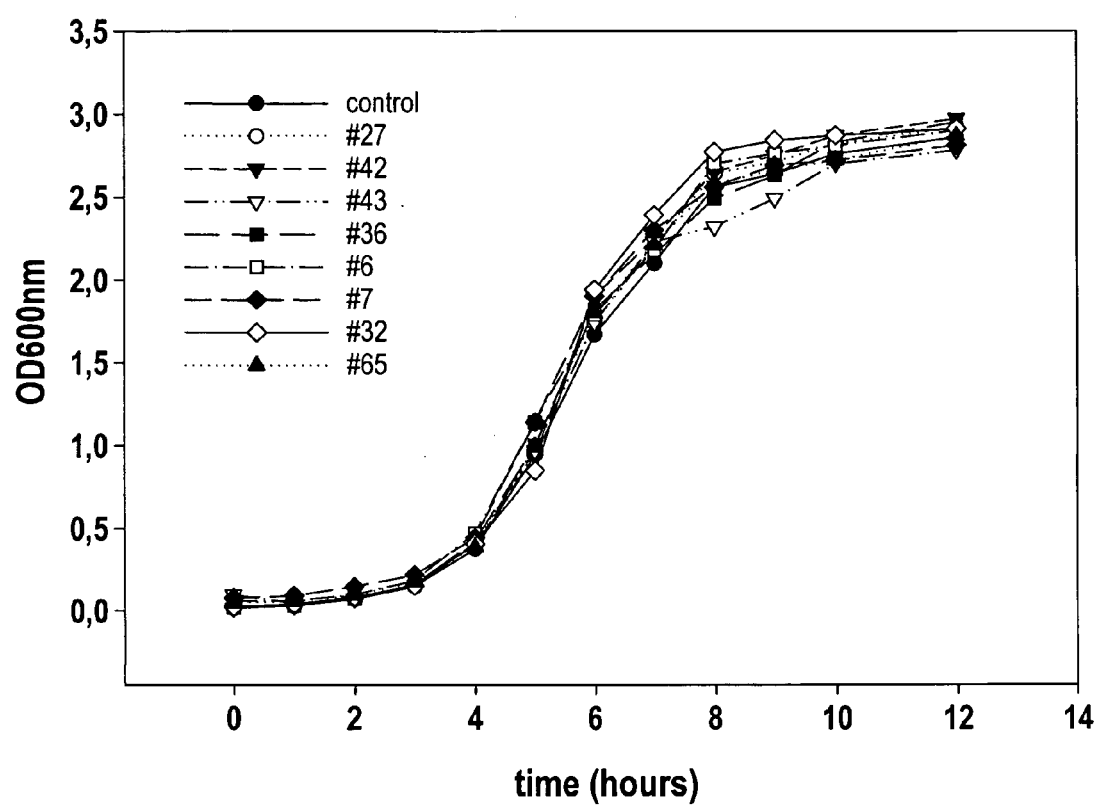
FIG. 4 illustrates the influence of the tested compounds on the growth of *P. aeruginosa* PAO-JP2.

To demonstrate that inhibition of protease production is due to a specific interference with the quorum sensing system growth curves in the presence and absence of the test compounds were compared. *P. aeruginosa* PAO-JP2 was grown in LB medium at 30° C. in the presence of 0.4 mM test compound. Growth was measured as optical density at 600 nm. None of the compounds listed in Table 2 exhibit any growth inhibitory effects on *P. aeruginosa* PAO-JP2. FIG. 4 shows the growth curves of representative compounds indicating a specific inhibitory effect of the compounds on the quorum sensing system.

4. Inhibition of Biofilm Formation

Figure 5:
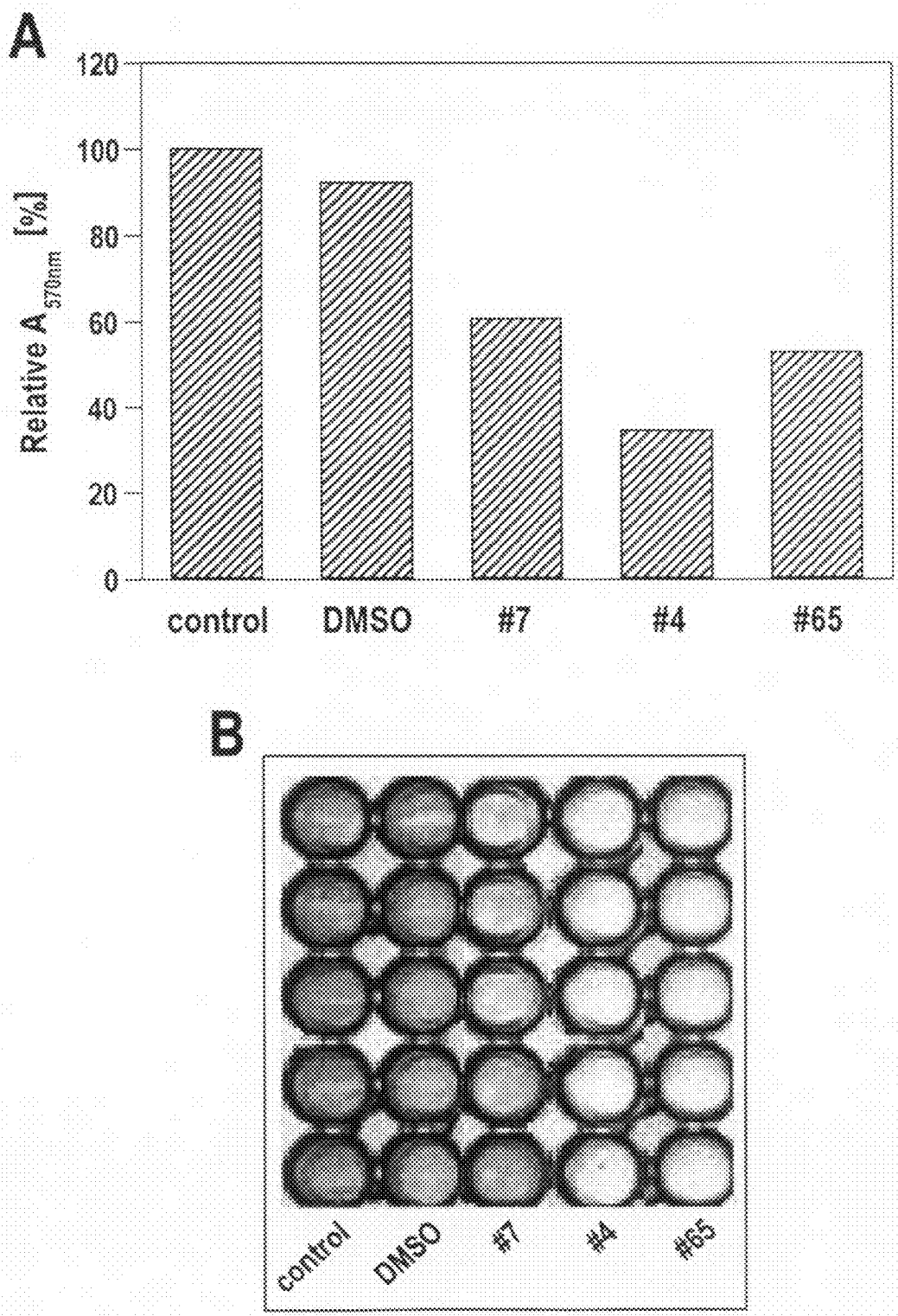
FIGS. 5A and 5B illustrate the inhibitory effect of several compounds on the biofilm formation of *Burkholderia cepacia* H111.

The bacterial biofilm formation assay was performed in polystyrene microtitre dishes (FluoroNunc Polysorp) according to the method described by O'Toole & Kolter (*Mol. Microbiol*. 28:449-61, 1998) and Pratt & Kolter (*Mol. Microbiol*. 4 30:285-93, 1998) with few modifications (Huber et al., *Microbiology*, 147:2517-28, 2001). Cells were grown in the wells of the microtitre dishes in 100 µl AB medium (Clark & Maaloe, *J. Mol. Biol*. 23:99-112, 1967) supplemented with 10 mM sodium citrate (Sigma). After addition of the test compound (0.4 mM) the cells were incubated for 48 hours at 30° C. The medium was then removed and 100 µl of a 1% (w/v) aqueous solution of crystal violet (Merck) was added. Following staining at room temperature for 20 minutes, the dye was removed and the wells were washed thoroughly with water. For quantification of attached cells, the crystal violet was solubilized in a 80:20 (v/v) mixture of ethanol and acetone and the absorbance was determined at 570 nm (Ultrospec Plus spectrometer, Pharmacia). FIGS. 5A and 5B demonstrate the inhibitory effect of several compounds on biofilm formation of *Burkholderia cepacia* H111 (Römling et al., *J. Infect. Dis*. 170:1616-21, 1994; Gotschlich et al., *Syst. Appl. Microbiol*. 24:1-14, 2001). The data presented are representative for at least five separate experiments.

Figure 6:
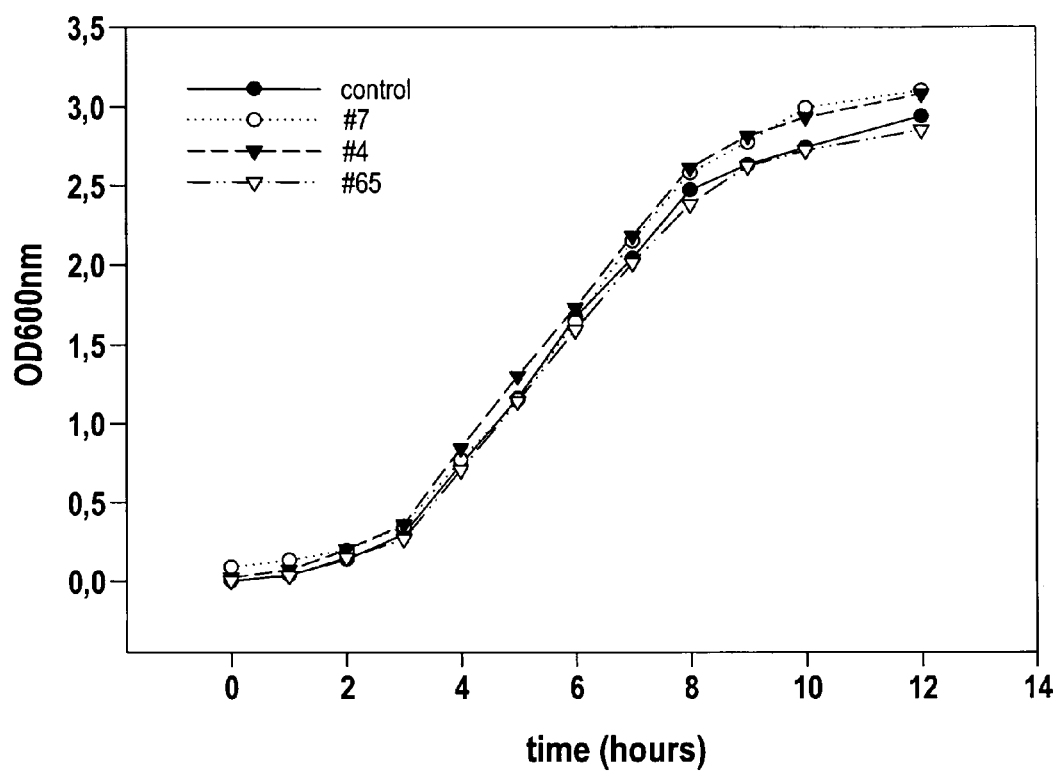
FIG. 6 illustrates the influence of the tested compounds on the growth of *Burkholderia cepacia* H111.

To exclude the possibility that biofilm inhibition is attributed to growth inhibition growth curves in the presence and absence of the test compounds were compared. *Burkholderia cepacia* H111 was grown in LB medium at 37° C. in the presence of 0.4 mM test compound. Growth was measured as optical density at 600 nm. None of the compounds listed in Table 2 exhibit any growth inhibitory effects on the sensor strain *Burkholderia cepacia* H111. FIG. 6 shows the growth curves of the tested compounds indicating a specific inhibitory effect of the compounds on the quorum sensing system.

The invention claimed is:
1. A composition for inhibiting bacterial quorum sensing, comprising a compound of Formula (I) or a pharmaceutically acceptable salt thereof and a carrier,

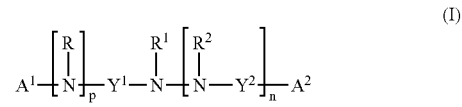

(I)

wherein in Formula (I),
R is H, alkyl, cycloalkyl, aryl or heteroaryl;
R1 and R2 is H;
Y1 is C=O;
Y2 is C=O;
A1 represents an optionally substituted 1,2-diazole ring, and A2 represents an optionally substituted alkyl group;
p is 1;
and n is 1.

2. A composition for inhibiting bacterial quorum sensing, comprising a compound or a pharmaceutically acceptable salt thereof and a carrier is

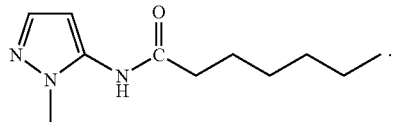

3. A composition of Formula (I) or a pharmaceutically acceptable salt thereof and a carrier,

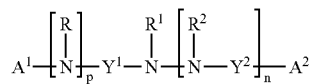

(I)

wherein in Formula (I),

R is H, alkyl, cycloalkyl, aryl or heteroaryl;

R1 and R2 is H;

Y1 is C=O;

Y2 is C=O;

A1 represents an optionally substituted 1,2-diazole ring, and A2 represents an optionally substituted alkyl group; and p=n=1.

4. The composition according to claim 3, further comprising at least one additional component selected from the group consisting of fillers, extenders, disintegrants, binders, glidants, wetting agents, stabilizers, emulsifiers, preservatives, sweetening agents, colorants, flavorings or aromatizers, buffer substances, solvents, solubilizers, salts for modifying osmotic pressure, coating agents and antioxidants.

* * * * *